US008980579B2

(12) United States Patent
Mauro et al.

(10) Patent No.: US 8,980,579 B2
(45) Date of Patent: Mar. 17, 2015

(54) CHROMOSOMAL LANDING PADS AND RELATED USES

(75) Inventors: Vincent P. Mauro, San Diego, CA (US); Wei Zhou, San Diego, CA (US); Bruce Cunningham, San Diego, CA (US); Gerald M. Edelman, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 320 days.

(21) Appl. No.: 13/440,661

(22) Filed: Apr. 5, 2012

(65) Prior Publication Data

US 2012/0258541 A1 Oct. 11, 2012

Related U.S. Application Data

(60) Provisional application No. 61/516,612, filed on Apr. 5, 2011.

(51) Int. Cl.

| | |
|---|---|
| ***C12P 21/06*** | (2006.01) |
| ***C12N 15/90*** | (2006.01) |
| *C12P 21/04* | (2006.01) |
| *C12N 5/07* | (2010.01) |
| *C12N 5/10* | (2006.01) |
| *C12N 15/00* | (2006.01) |
| *C12N 15/87* | (2006.01) |

(52) U.S. Cl.

CPC ........ *C12N 15/907* (2013.01); *C12N 2800/107* (2013.01); *C12N 2800/30* (2013.01)

USPC ........ 435/69.1; 435/70.1; 435/70.3; 435/325; 435/358; 435/455; 435/463

(58) Field of Classification Search

None

See application file for complete search history.

(56) References Cited

U.S. PATENT DOCUMENTS

| | | | |
|---|---|---|---|
| 4,945,050 | A | 7/1990 | Sanford et al. |
| 5,175,384 | A | 12/1992 | Krimpenfort et al. |
| 5,175,385 | A | 12/1992 | Wagner et al. |

OTHER PUBLICATIONS

Scotland et al., "Nervous System Defects of AnkyrinB (-/-) Mice Suggest Functional Overlap between the Cell Adhesion Molecule L1 and 440-kD AnkyrinB in Premyelinated Axons" 143(5) The Journal of Cell Biology (1998).*

Kuwayama, "Enhancement of Homologous Recombination Efficiency by Homologous Oligonucleotides" Intech, Chapter 9, 233-244 (2012).*

Ristevski, "Making Better Transgenic Models" 29 Molecular Biotechnology 153-163 (2005).*

Montoliu, "Gene Transfer Strategies in Animal Transgenesis" (4(1) Cloning and Stem Cells 39-46 (2002).*

Mortensen, "Overview of Gene Targeting by Homologous Recombination" (Supplement 40 Current Protocols in Neuroscience 4.29.1-4.29.13 (2007).*

Capecchi, "Altering the Genome by Homologous Recombination" 244 Science 1288-1292 (1989).*

Cameron, "Recent Advances in Transgenic Technology" 7 Molecular Biotechnology 253-265 (1997).*

Alonso et al., *Proc. Natl. Acad. Sci. USA* 84:1997-2001, 1987.

Benoist et al., *Nature* (London) 290:304-310, 1981.

Botstein et al., *Miami Wntr. Symp.* 19:265-274, 1982.

Brinster, et al., *Proc. Nat. Acad. Sci. USA* 82: 4438, 1985.

Broach, *Cell* 28:203-204, 1982.

Broach, *In: The Molecular Biology of the Yeast Saccharomyces: Life Cycle and Inheritance*, Cold Spring Harbor Laboratory, Cold Spring Harbor, N.Y., p. 445-470, 1981.

Chadwick et al., *Gene Therapy* 4:937-942, 1997.

Chappell et al., *PNAS* 103(25):9488-9493 (2006).

Christiansen et al., *J. Bacteriol.* 178:5164-5173, 1996.

Dilon et at., *J. Clin. Hematol. Oncol.* 10:39-48, 1980.

Enquist et al., *Cold Spring Harbor Symp. Quant. Biol.* 43:1115-1120, 1979.

Eulalio et al., *Cell* 132:9-14 (2008).

Fingl et al., 1975, in *The Pharmacological Basis of Therapeutics*, Ch. 1 p. 1.

Gao and Huang, *Gene Therapy* 2:710-722, 1995.

Genbank Database [online], Feb. 5, 2007, Rieder et al.: '*Homo sapiens* cleavage and polyadenylation specific factor 4, 30kDA (CPSF4) gene, complete cds.', [retrieved on Jul. 5, 2012], Accession No. EF191081.

Genbank Database [online], Jun. 14, 2012, TSE et al.: '*Homo sapiens* ankyrin 2, neuronal (ANK2), RefSeqGene (LRG_327) on chromosome 4', [retrieved on Jul. 5, 2012], Accession No. NG_009006.

Genbank Database [online], Oct. 27, 2011, '*Cricetulus griseus* unplaced genomic scaffold, CriGri_1.0 scaffold1969, whole genome shotgun sequence.' [retrieved on Jul. 5, 2012], Accession No. NW_003613665.1.

Genbank Database [online], Oct. 27, 2011, '*Cricetulus griseus* unplaced genomic scaffold, CriGri_1.0 scaffold831, whole genome shotgun sequence.' [retrieved on Jul. 5, 2012], Accession No. NW_003614125.1.

(Continued)

*Primary Examiner* — Celine Qian
*Assistant Examiner* — Nancy J Leith
(74) *Attorney, Agent, or Firm* — Cooley LLP; Ivor Elrifi; Christina K. Stock

(57) ABSTRACT

Provided herein are methods for stable integration and/or expression of one or more recombinant polynucleotides in a host cell. The recombinant polynucleotides are typically integrated into the host genome at some native chromosomal integration sites. The integration can be mediated by homologous recombination or by using a hybrid recombinase targeting the specific chromosomal locations. The native chromosomal integration sites in the host cells, which support stable integration and strong transcription activities of foreign genes, are present within or adjacent to specific genes in the CHO genome, the ankyrin 2 gene (Ank2), cleavage and polydenylation specific factor 4 gene (Cpsf4), C-Mos gene, and Nephrocystin-1/Mal gene. Also provided are methods and nucleic acid molecules for inserting site-specific recombination sequences (chromosomal landing pads) into these specific chromosomal locations, engineered host cells containing chromosomal landing pads, methods and compositions (e.g., kits) therefore.

14 Claims, 6 Drawing Sheets

(56) References Cited

OTHER PUBLICATIONS

Genbank Database [online], Oct. 27, 2011, '*Cricetulus griseus* unplaced genomic scaffold, CriGri_1.0 scaffold3898, whole genome shotgun sequence', [retrieved on Jul. 5, 2012], Accession No. NW_003614707.1.
Genbank Database [online], Oct. 27, 2011, '*Cricetulus griseus* unplaced genomic scaffold, CriGri_1.0 scaffold C41115684, whole genome shotgun sequence', [retrieved on Jul. 5, 2012], Accession No. NW_003635654.1.
Genbank Database [online], Oct. 27, 2011, '*Cricetulus griseus* unplaced genomic scaffold, CriGri_1.0 scaffold5419, whole genome shotgun sequence', [retrieved on Jul. 5, 2012], Accession No. NG_003615916.1.
Goddard, et al, *Gene Therapy*, 4:1231-1236, 1997.
Gokhale et al., *Gene Therapy* 4:1289-1299, 1997.
Gorman et al., *Gene Therapy* 4:983-992, 1997.
Gregory et al., *J. Bacteriol*., 185:5320-5323, 2003.
Groth and Calos, *J. Mol. Biol*. 335:667-678, 2004.
Groth et al., *Proc. Natl. Aacd. Sci. USA*97:5995-6000, 2000.
Hamer et al., *J. Mol. Appl. Gen*. 1:273-288, 1982.
Hammer et al., *Nature*, 315:680, 1985.
Henikoff & Henikoff, *Proc. Natl. Acad. Sci. USA* 89:10915 (1989).
Hollis et al., *Repr. Biol. Endocrin*. 1:79, 2003.
Houdebine and Chourrout, *Experientia* Sep. 15, 1991;47(9):891-897.
Hu et al., *PNAS USA* 96:1339-1344 (1999).
Jasny, Science 238:1653, 1987.
Johnston et al., *Proc. Natl. Acad. Sci*. (*USA*) 79:6971-6975, 1982.
Kahmann et al., *Cell* 41:771-780, 1985.
Kevarala et al., *Mol. Ther*. 17, 112-120, 2008.
Kozak, *J. Cell Biol*. 108:229-241 (1989).
Krasnow et al., *Cell* 32:1313-1324, 1983.
Krimpenfort et al., *Biotechnology* (*NY*). Sep. 1991;9(9):844-847.
Kuhstoss and Rao, *J. Mol. Biol*. 222, 897-908, 1991.
Lee et al., *J. Bacteriol*. 175:6836-6841, 1993.
Leong et al., *J. Biol. Chem*. 260:4468-4477, 1985.
Maniatis, In: *Cell Biology: A Comprehensive Treatise*, vol. 3, Gene Sequence Expression, Academic Press, NY, pp. 563-608, 1980.
Mauro et al., *JBC* 283(48):33087-33093 (2008).
McKnight, *Cell* 31:355-365, 1982.
Meijer et al., *JBC* 275(40):30787-30793 (2000).
Miller et al., *In: Genetic Engineering* (1986) Setlow, J. K., et al., eds., Plenum, vol. 8, pp. 277-298.
Monahan et al. *Gene Ther*. Jan. 1998;5(1):40-49.
Morris et al., *Hum. Genetics* 81:339-342, 1989.
Neel et al., *Proc. Natl. Acad. Sci. USA*, 79: 7842-6, 1982.
Olivares et al., *Gene* 278:167-176, 2001.
Onodera et al., *Blood* 91:30-36, 1998.
Owens et al., *PNAS* 98(4):1471-1476 (2001).
Palmiter et al., *Cell* 41:343, 1985.
Peabody, *JBC* 262(24):11847-11851 (1987).
Peabody, *JBC* 264(9):5031-5035 (1989).
Pursel, et al., *Science* 244:1281-1288, 1989.
Rancano et al., *J. Biol. Chem*. 269:8159-8164, 1994.
Rausch and Lehmann, *Nucleic Acids Research* 19, 5187-5189, 1991.
Reed et al., *Nature* 300:381-383, 1982.
Rubin, *Science* 240:1453-1459, 1988.
Sclimenti et al., *Nuc. Acid Res*. 29:5044-5051, 2001.
Shuman, *Experientia* Sep. 15, 1991;47(9):897-905.
Silver et al., *Proc. Natl. Acad. Sci*. (*USA*) 81:5951-5955,1984.
Simons, et al., *Bio/Technology* 6:179-183, 1988.
Siprashvili et al., *Mol. Ther*., 9:721-728, 2004.
Smith and Thorpe, *Mol Microbiol*. Apr. 2002;44(2):299-307.
Smith et al., Nuc. Acids Res. 32, 2607-2617, 2004.
Stoll et al., *J. Bacteriol*., 184:3657-3663, 2002.
Thyagarajan et al., *Mol. Cell Biol*. 21(12):3926-3934, 2001.
Waldman et al., *J. Bacteriol*. 165:297-300, 1986.
Weissbach & Weissbach, *Methods for Plant Molecular Biology*, Academic Press, NY, Section VIII, pp. 421-463, 1988.
Yagil et al., *J. Mol. Biol*. 207:695-717,1989.
Bertoni et al., "Enhanced Plasmid-Mediated Dystrophin Expression in the mdx Mouse Model for Duchenne Muscular Dystrophy by a PhiC31 Integrase Plasmid System", *Molecular Therapy*, vol. 11, Supplement 1, May 2005, p. S104.
Chalberg et al., "Integration Specificity of Phage ΦC31 Integrase in the Human Genome", *J. Mol. Biol*. (2006) 357, pp. 28-48.
Held et al., "In Vivo Correction of Murine Hereditary Tryosinemia Type I by ΦC31 Integrase-Mediated Gene Delivery", *Molecular Therapy*, vol. 11, No. 3, Mar. 2005, pp. 399-408.
Huang et al., "An efficient and targeted gene integration system for high-level antibody expression", *Journal of Immunological Methods* 322 (2007), pp. 28-39.
Keravala et al., "A diversity of serine phage integrases mediate site-specific recombination in mammalian cells", *Mol Gen Genomics* (2006) 276: pp. 135-146.
Lieu et al., "Generation of Site-Specific Retargeting Platform Cell Lines for Drug Discovery Using phiC31 and R4 Integrases", *Journal of Biomolecular Screening* 14(10); 2009, pp. 1207-1215.
Nishiumi et al., "Simultaneous Single Cell Stable Expression of 2-4 cDNAs in HeLaS3 Using ΦC31 Integrase System", *Cell Structure and Function* 34: 2009; pp. 47-59.
Olivares et al., "Site-specific genomic integration produces therapeutic Factor IX levels in mice", *Nature Biotechnology*, vol. 20, Nov. 2002; pp. 1124-1128.
Portlock et al., "Characteristics of Site-Specific Integration as Mediated by PhiC31 Integrase in the Human Genome", *Molecular Therapy*, vol. 11, Supplement 1, May 2005.
Sorrell et al., "Targeted modification of mammalian genomes", *Biotechnology Advances* 23 (2005); pp. 431-469.
Thyagarajan et al., "Site-Specific Integration for High-Level Level Protein Production in Mammalian Cells", *Methods in Molecular Biology*, vol. 308: Therapeutic Proteins: Methods and Protocols; pp. 99-106, 2005.
Thyagarajan et al., "Creation of Engineered Human Embryonic Stem Cell Lines Using phiC31 Integrase", *Stem Cells* 2008; 26: pp. 119-126.
Wiberg et al., "Production of Target-Specific Recombinant Human Polyclonal Antibodies in Mammalian Cells", *Biotechnology and Bioengineering*, vol. 94, No. 2, Jun. 5, 2006; pp. 396-405.
Wirth et al., "Road to precision: recombinase-based targeting technologies for genome engineering", *Current Opinion in Biotechnology* 2007, 18: pp. 411-419.

* cited by examiner attP: CCC CAA CTG GGG TAA CCT TTG AGT TCT CTC AGT TGG GGG (SEQ ID NO: 5)

GGGGTT GAC CCC ATT GGA AAC TCA AGAGAGTCA ACC CCC (SEQ ID NO: 6)

attB: G TGC CAG GGC GTG CCC TTG GGC TCC CCG GGC GCG (SEQ ID NO: 7)

C ACG GTC CCG CAC GGG AAC CCG AGG GGC CCG CGC (SEQ ID NO: 8)

*FIG. 3*

A native chromosomal insertion site in ankyrin 2 gene (Ank2)

(SEQ ID NO: 1)

```
5'- aaaatttctt gctttcttct aaaagcatta tctataaata tttgttgtct aaaactcatt        60
tttcccatgt ttagtgtgtg tgtttatgcg tgagtgcata ttgtcttggc taccatgaag       120
agaaatatta -Insertion- tttttccttc cagtgttctt gagtggcaaa ttacttttct gttgcagtgt       180
gacaacacca ggggcagaag gggcagagac tcaaaaagcc acagaagttc ctgactctct       240
ctgtaagact cctg -3'                                                     254
```

*FIG. 4*

A native chromosomal insertion site in cleavage and polyadenylation specific factor 4 gene (Cpsf4)

(SEQ ID NO: 2)

```
5'-ataaaatcaa aataatgcat cttttgaaga aagcataaaa accaatatac agaattgtga     60
tatgacccgg catccctttt gggacggcag tgactgcagg cgagaaggag gggatggcag     120
agagcagtgt gaagtgggga gggcagctaa gagacctgag ggggagccag gtcctaggcc     180
tctgccgccg ctgccatgca taaaatcatc gccagcgtgg accctatcaa gttcgacttg     240
gagatcgcca tggagcaaca gctccaggcc cttcccagga taagtcgggg gctgctgtct     300
gagaattcat tttgaaagct gcctgtggca aatgtggcat gtgtccattc cgccacatta     360
gtggtgagaa gacagttgtg tgcaaacact ggctaagagc actctgcaag aaaggggacc     420
agtgtgagtt cttacatgag tacgacatga ccaagatgcc cgagtactac ttttacccca     480
agttcgggaa atgcaacaac aaggagtgcc ccttcctgta catcgaccct gagtctaaga     540
ttaaggactg cccttggtat gaccacggct tctgtaagca tggccccctg tgcaggcatc     600
ggcacactcg gagagtcatt tgtgtgaat -Insertion- t acctggtagg attctgccct gaggaaccct     660
agggtagatt catgcaccct ccatttgaac tgcccatggg aaccactgag caacctccac     720
taccacaaca gatacagcct ccaacaaaga tcattgggtt catgcagagt caaaatagca     780
gtgcagggaa cctgggaccc tggacattgg agcaagtcac ttactataag tgtggtaaaa     840
aaggacacta tgccaacaga tgcaccaaag ggccaattgg catttctcag tggacagtga     900
caatagctgg gctctgtgga gcagcctaag agacctgctg ttggtaacaa gcacttagct     960
gctcaatgta gtgctggcag gactggctag agcctcaggc acacttgcca gggctcattt     1020
tgaggggcca tgtctgtcct atcattttgc tgtaatcttt tttctttaaa gaaggaacat     1080
gtgcttcagt tgggtccctt gagccagctt gcttggacat cagtgcctca tttttggac     1140
tatgtgct -3'                                                          1148
```

*FIG. 5*

A native chromosomal insertion site in C-Mos gene (SEQ ID NO: 3)

```
cagacatttg ttgaactact tgccagggtt attagatgca acctttgtaa gaattaacat        60
ctgtaacttt aatgtctttg atccaaatac aatcacttat agaagtcaga tcacatacct       120
tttacgttca tcagaaggga gcattctgac actgtatttg atttaaacag caagttaaga       180
ctctgtaaca taacaacaca gtgacctccc aatatccctt tccaaggcaa gttaagccac       240
cccatgagtg tgagtttgct tcaagacaga tt -Insertion– ctagactt cacagaaagc aagttcctgg
aatttaatgc agagttggag gaaggaagaa aggaacaaag gtgattgtga tgaccacggc       360
tgtaaatatc agcaagcgtg ggaaaacaga ggaaaagtca ggagaaatag acatggctca       420
gaatcactgg tacccatcta taatatggaa aagcagatgc tgaacacaaa ttcagggtct       480
ggccatcaaa ccacacattc ctcctttttt gttttataaa aatgcgctca gttttatgct       540
atatctctgg gagaatgggg aagagccttg ctctgtttat tcaaaaacgt ttctcaaagt       600
ggctaggagt tactcctctt agctgcttgg taaggtgttt tatgcataca ggtgataagt       660
gatcactttt catgtgacag ctgtgtccct ttgacttcag aatcacaggt tttgagaaga       720
caataaagga gagacatata aac   -3'                                             743
```

*FIG. 6*

A native chromosomal insertion site in Nephrocystin-1/Mal gene (SEQ ID NO: 4)

```
cctccagaaa gccttgcggg tcaactaaga attcggtcta acgactcacc aaccctcaac        60
actcctcatc cctcaggccc ttgtctaaac tagccagacc cacccagccc agcgcccctc       120
tcctttgaaa ttcatcactt tctcaaagtg taacaggtgt caacgtatag tcttaataaa       180
ctaaccaagg acagattagt aatttcagaa aagttaattt caaagatgat caaacacaa -insertion- a       240
agatcgtagc gattttaagt cataaccctc agtgctgagg aagactcgat gaaacaggcg       300
atgccctggt atatagtcta catttctgga cagcagtttg acaacatata gcgagcattg       360
atcctcctag gctggttgat tacattctca gcaatctccc acttacaata acttaaaagt       420
gtgacagaga tggatattta aatgtgttca ccacattttt tgcttataat agaaaagctg       480
aatatgaata aatgataggt attagtggga tggataaact aatccataga tggattaatg       540
ttatacaggg cttctcagtt cttcttttga gggaaaggat ttagtggcag gacacaaagc       600
ttaaacagaa gtttatat                                                     618
```

CHROMOSOMAL LANDING PADS AND RELATED USES

REFERENCE TO PRIORITY DOCUMENT

This application claims the benefit of priority under 35 U.S.C. §119(e) of U.S. Provisional Patent Application Ser. No. 61/516,612, filed Apr. 5, 2011. Priority of the aforementioned filing date is hereby claimed and the disclosure of the provisional patent application is hereby incorporated by reference in its entirety.

INCORPORATION OF SEQUENCE LISTING

This application contains an electronic equivalent paper copy of the sequence listing submitted herewith electronically via EFS web and a computer-readable form of the sequence listing submitted herewith electronically via EFS web and contains the file named "37651505001US SEQUENCE LISTING.txt," which is 208 kb in size and which was created on Apr. 5, 2012, and the contents of the text file named "37651505001USSEQUENCELISTING2.txt", which was created on May 18, 2012 and is 209 KB in size, are hereby incorporated by reference in their entirety.

BACKGROUND

Integration of heterologous polynucleotides into the genomes of mammalian cells is routinely practiced for therapeutic purposes (e.g., gene therapy) and in the production of useful proteins or polypeptides in vitro. Insertion at random locations in the genome by non-homologous recombination requires several rounds of selection and clonal expansion to produce an acceptable expression system. The approach also needs to be repeated every time an expression system for a new gene is sought. Due to the random nature of the integration event, some of the locations where recombinant genes are inserted are incapable of supporting transcriptional events at all. This is because expression levels are greatly influenced by the effects of the local genetic environment at the gene locus (position effects). In addition, expression from many chromosomal sites is decreased over time. In some cases, this instability is due to DNA methylation of the transgene. As a result, wide variations in the expression level of integrated genes can occur, depending on the site of integration. In addition, random integration of exogenous DNA into the genome can in some instances disrupt important cellular genes, resulting in an altered phenotype.

Other than random insertion, recombinase-mediated integration has been described for insertion of transgenes at defined sites in the genome. However, achieving stable, high-efficient expressions of integrated transgenes is still cumbersome and requires large numbers of screened clones in order to select desirable integrated cells.

There is a need in the art for means for achieving a stable integration and/or high level of gene expression of heterologous polynucleotide in mammalian cells. The present disclosure addresses this and other needs.

SUMMARY

In one aspect, provided are methods for stable integration and expression of a heterologous polynucleotide in a host cell. The methods involve inserting the heterologous polynucleotide into the genome of the host cell at a native chromosomal site located within or adjacent to a gene selected from the group consisting of ankyrin 2 gene (Ank2), cleavage and polyadenylation specific factor 4 gene (Cpsf4), C-Mos gene and Nephrocystin-1/Mal gene. In some methods, insertion of the heterologous polynucleotide into the host genome is mediated by homologous recombination or by a hybrid recombinase. In some methods, the host cell is a mammalian cell, e.g., a Chinese hamster ovary (CHO) cell. In some of these methods, the native chromosomal insertion site is at or close to positions 130-131 of SEQ ID NO:1 for the Ank2 gene, positions 629-630 of SEQ ID NO:2 for the Cpsf4 gene, positions 272-273 of SEQ ID NO:3 for the C-Mos gene, or positions 239-240 of SEQ ID NO:4 for the Nephrocystin-1/Mal gene. In some methods, the heterologous polynucleotide to be integrated into the host genome can encode a polypeptide, e.g., a therapeutic protein or an industrial protein.

In a related aspect, provided are recombinant or engineered polynucleotides for stably integrating a heterologous polynucleotide sequence into the genome of a mammalian cell. The recombinant polynucleotides typically contain a first homology arm, the heterologous polynucleotide sequence, and a second homology arm. The first and second homology arms are substantially identical to the 5'- and 3'-sequences, respectively, that flank a native chromosomal insertion site located within or adjacent to a gene selected from the group consisting of ankyrin 2 gene (Ank2), cleavage and polyadenylation specific factor 4 gene (Cpsf4), C-Mos gene and Nephrocystin-1/Mal gene. Typically, the native chromosomal insertion site is capable of supporting stable integration of a foreign gene. In some methods, the heterologous polynucleotide sequence encodes a polypeptide, e.g., a therapeutic protein or an industrial protein. In some other methods, the heterologous polynucleotide sequence comprises a site-specific recombination sequence (chromosomal landing pad). For example, the site-specific recombination sequence can be a recognition sequence recognized by a phage integrase, such as the attP site or the attB site recognized by phiC-31 phage integrase. In some methods, the host mammalian cell is a Chinese hamster ovary (CHO) cell. In these methods, the native chromosomal insertion site can be located at or close to positions 130-131 of SEQ ID NO:1 for the Ank2 gene, positions 629-630 of SEQ ID NO:2 for the Cpsf4 gene, positions 272-273 of SEQ ID NO:3 for the C-Mos gene, or positions 239-240 of SEQ ID NO:4 for the Nephrocystin-1/Mal gene. In related embodiments, vectors containing the recombinant or engineered polynucleotides are also provided in the invention.

In another aspect, provided are engineered mammalian cells. The cells harbor a heterologous polynucleotide that is stably integrated into its genome at one or more native chromosomal insertion sites located within or adjacent to a gene selected from the group consisting of ankyrin 2 gene (Ank2), cleavage and polyadenylation specific factor 4 gene (Cpsf4), C-Mos gene and Nephrocystin-1/Mal gene. Typically, the chosen native chromosomal insertion site supports stable integration of a foreign gene. In some of the methods, the heterologous polynucleotide encodes a polypeptide, e.g., a therapeutic protein or an industrial protein. In some other methods, the heterologous polynucleotide contains a site-specific recombination sequence (chromosomal landing pad). For example, the site-specific recombination sequence can be a recognition sequence recognized by a phage integrase, such as the attP site or the attB site recognized by phiC-31 phage integrase. Some preferred embodiments are directed to recombinant or engineered Chinese hamster ovary (CHO) cells. In these embodiments, the heterologous polynucleotide can be preferably integrated at or close to positions 130-131 of SEQ ID NO:1 for the Ank2 gene, positions 629-630 of SEQ ID NO:2 for the Cpsf4 gene, positions 272-273 of SEQ ID NO:3 for the C-Mos gene, or positions 239-240 of SEQ ID NO:4 for the Nephrocystin-1/Mal gene.

In still another related aspect, provided are methods for stably integrating a heterologous polynucleotide into the genome of a mammalian cell. These methods entail (a) inserting a site-specific recombination sequence into the genome of the cell, wherein the insertion is at a native chromosomal insertion site located within or adjacent to a gene selected from the group consisting of ankyrin 2 gene (Ank2), cleavage and polyadenylation specific factor 4 gene (Cpsf4), C-Mos gene and Nephrocystin-1/Mal gene; and (b) integrating by homologous recombination the heterologous polynucleotide into the genome of the cell at the inserted site-specific recombination sequence. The native chromosomal insertion site chosen for the methods typically supports stable integration of a foreign gene. In some methods, the site-specific recombination sequence is a first recognition sequence recognized by a phage integrase, e.g., the attP site or the attB site of phiC-31 phage integrase. In these methods, the heterologous polynucleotide is usually attached to a second recognition sequence of the phage integrase which is cognate to the first recognition sequence, e.g., the attB site or the attP site recognized by the phage integrase. In some methods, the employed mammalian host cell is a Chinese hamster ovary (CHO) cell. In these methods, the site-specific recombination sequence can be preferably inserted into the genome at or close to positions 130-131 of SEQ ID NO:1 for the Ank2 gene, positions 629-630 of SEQ ID NO:2 for the Cpsf4 gene, positions 272-273 of SEQ ID NO:3 for the C-Mos gene, or positions 239-240 of SEQ ID NO:4 for the Nephrocystin-1/Mal gene. In some methods, the heterologous polynucleotide contains a target polypeptide-encoding sequence that is operably linked to a promoter sequence. Typically, integration of the heterologous polynucleotide into the host genome occurs in the presence of the phage integrase. In some of these methods, the phage integrase can be expressed from a vector introduced into the cell.

A further understanding of the nature and advantages of the present invention may be realized by reference to the remaining portions of the specification and claims.

BRIEF DESCRIPTION OF THE DRAWINGS

FIG. 3 shows a native chromosomal insertion site and flanking sequences in the ankyrin 2 (Ank2) gene of CHO cell genome (SEQ ID NO:1).

FIG. 4 shows a native chromosomal insertion site and flanking sequences in the cleavage and polyadenylation specific factor 4 (Cpsf4) gene of CHO cell genome (SEQ ID NO:2).

FIG. 5 shows a native chromosomal insertion site and flanking sequences in the C-Mos gene of CHO cell genome (SEQ ID NO: 3).

FIG. 6 shows a native chromosomal insertion site and flanking sequences in the Nephrocystin-1/Mal gene of CHO cell genome (SEQ ID NO: 4).

DETAILED DESCRIPTION

I. Overview

Figure 1:
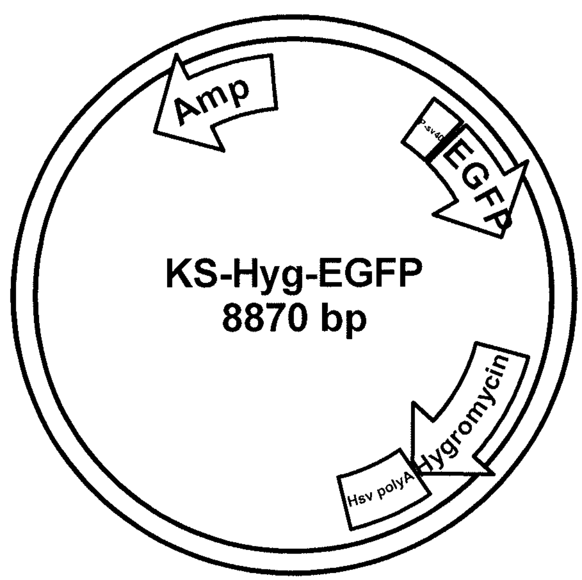
FIG. 1 is a diagram showing the structure of the plasmid used for random integration into CHO genome for identifying native chromosomal insertion sites that support strong transcription activities. The plasmid contains a sv40 promoter driven EGFP expression cassette. The BamHI site is between EGFP and Hygromycin resistance gene (for linearization before stable integration).

Disclosed herein are native chromosomal sites in mammalian cells that are capable of strong transcriptional activity of a recombinant gene and their use as "landing pads" for site-specific integration of recombinant constructs. Specifically, chromosomal locations in several genes in mammalian genomes (e.g., Chinese Hamster Ovary (CHO) genome) were identified that promote strong expression of integrated foreign genes. As described below, identification of these native chromosomal insertion sites involved random integration into the genome of plasmids containing genes for selection (e.g., hygromycin-resistance gene and gene encoding the Enhanced Green Fluorescent Protein, EGFP). Upon random integration, cells were selected for hygromycin-resistance and sorted for EGFP expression using Fluorescent Activated Cell Sorting (FACS) three weeks after initial transfection. Selected cells were allowed to recover and grown without selection for several more weeks. Cells were then FACS-sorted again. Cells with the highest EGFP levels were sorted into individual wells of 96-well plates. Clones were grown from single cells and cultured for several weeks. Cells were then retested for EGFP expression. Cells were further screened to identify those with growth rates that were comparable to or higher than the growth rate of the parental cell line. Sequences at the insertions sites in these genes were then analyzed. These studies resulted in the identification of several genes, ankyrin 2 gene (Ank2), cleavage and polyadenylation specific factor 4 gene (Cpsf4), C-Mos gene and Nephrocystin-1/Mal gene, which harbor native chromosomal sites that enable stable and strong transcription activities from a recombinant gene.

Also described herein is the indentification of native chromosomal sites as chromosomal landing pads for uniform integration of desired target polynucleotide sequences. To this end, the phage attachment site attP recognized by phage integrase is introduced into the native chromosomal sites through homologous recombination. With the site-specific recombination sequence (i.e., the attP site) inserted into the genome, recombinant genes can then be readily introduced into the cell using vectors containing the cognate recombination sequence (i.e., attB attachment site) that is recognized by the phage integrase (e.g., the phiC-31 phage integrase) in the presence of the phage integrase. The phage integrase allows the recombination of the two cognate recombination sequences (i.e., attB and attP sites), such that the entire attB-containing vector can be integrated into a single attP site in the chromosome.

Provided herein are methods for stable integration and/or expression of a heterologous polynucleotide in a host cell. Host cells containing a heterologous polynucleotide stably integrated in or near one or more of the identified genes (i.e., Cpsf4, Ank2, C-Mos, and Nephrocystin-1/Mal genes) are also provided. Further provided are polynucleotides and related vectors which are useful for inserting a heterologous polynucleotide, e.g., a site-specific recombination sequence (chromosomal landing pad), into the genome of a mammalian cell, in particular into one or more of the native chromosomal insertion sites disclosed herein. Additionally provided are engineered mammalian cells which have a heterologous site-specific recombination sequence that is stably integrated into its genome at one or more of the native chromosomal insertion sites disclosed herein. Moreover, provided are methods for stable integration at one or more inserted chromosomal landing pads and expression in a mammalian cell of a heterologous polynucleotide that encodes a target polypeptide of interest. Cells thus generated for expressing the heterologous polynucleotide is also provided herein.

The particular methodology, protocols, and reagents described here can vary. Unless otherwise indicated, conventional techniques of molecular biology (including recombinant techniques), microbiology, cell biology, biochemistry and immunology, which are within the skill of the art can be employed. Such techniques are explained fully in the literature. For example, exemplary methods are described in the following references, Sambrook et al., *Molecular Cloning: A Laboratory Manual*, Cold Spring Harbor Press (3rd ed., 2001); Brent et al., *Current Protocols in Molecular Biology*, John Wiley & Sons, Inc. (ringbou ed., 2003); Freshney, *Culture of Animal Cells: A Manual of Basic Technique*, Wiley-Liss, Inc. (4th ed., 2000); and Weissbach & Weissbach, *Methods for Plant Molecular Biology*, Academic Press, NY, Section VIII, pp. 42 1-463, 1988.

II. Definitions

Unless defined otherwise, all technical and scientific terms used herein have the same meaning as commonly understood by those of ordinary skill in the art to which this disclosure pertains. The following references provide one of skill with a general definition of many of the terms used in this disclosure: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3rd ed., 2002); *Dictionary of Chemistry*, Hunt (Ed.), Routledge (1st ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4[t1] ed., 2000). Further clarifications of some of these terms as they apply specifically to this disclosure are provided herein.

As used herein, the singular forms "a", "an", and "the" include plural reference unless the context clearly dictates otherwise. Thus, for example, reference to "a cell" includes a plurality of such cells, reference to "a protein" includes one or more proteins and equivalents thereof known to those skilled in the art, and so forth.

The term "agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "chromosomal landing pad" (or simply "landing pad") refers to a site-specific recognition sequence or a site-specific recombination site (e.g., an attP site) that is stably integrated into the genome of a host cell (e.g., a mammalian cell such as CHO cell). In particular, the site-specific recognition sequence or recombination site is inserted into the host genome at one or more native chromosome insertion sites present in several specific genes disclosed herein, i.e., ankyrin 2 gene (Ank2), cleavage and polyadenylation specific factor 4 gene (Cpsf4), C-Mos gene and Nephrocystin-1/Mal gene. Presence in the host genome of the heterologous site-specific recombination sequence allows a recombinase (e.g., phiC-31 integrase) to mediate site-specific insertion of a heterologous polynucleotide or a transgene into the host genome. Typically, in order to integrate into the landing pad, the heterologous polynucleotide or transgene is attached to a cognate recognition sequence or recombination site (e.g., an attB site if the inserted site-specific recombination site is an attP site) that is also recognized by the recombinase.

The phrase "polynucleotide of interest" (or "gene of interest" or "target gene") is intended to include a cistron, an open reading frame (ORF), or a polynucleotide sequence which codes for a polypeptide or protein product ("polypeptide of interest" or "target polypeptide"). For stable integration and expression in an engineered host cell bearing a chromosomal landing pad described herein, a polynucleotide of interest can additionally contain appropriate transcription regulatory elements (e.g., promoter sequences) operably linked to the coding sequence and also a cognate site-specific recombination sequence (e.g., attB or attP site). Various target polypeptides can be encoded by and expressed from a polynucleotide of interest, e.g., therapeutic proteins, nutritional proteins and industrial useful proteins.

The term "endogenous" as used herein refers to a nucleic acid or polypeptide that is normally found in the wild-type host, while the term "exogenous" refers to a nucleic acid or polypeptide that is not normally found in the wild-type host.

A "host cell" refers to a living cell into which a heterologous polynucleotide sequence is to be or has been introduced. The living cell includes both a cultured cell and a cell within a living organism. Means for introducing the heterologous polynucleotide sequence into the cell are well known, e.g., transfection, electroporation, calcium phosphate precipitation, microinjection, transformation, viral infection, and/or the like. Often, the heterologous polynucleotide sequence to be introduced into the cell is a replicable expression vector or cloning vector. In some embodiments, host cells can be engineered to incorporate a desired gene on its chromosome or in its genome. Many host cells (e.g., CHO cells) that can serve as hosts are known in the art. See, e.g., Sambrook et al., *Molecular Cloning: A Laboratory Manual*, Cold Spring Harbor Press (3rd ed., 2001); and Brent et al., *Current Protocols in Molecular Biology*, John Wiley & Sons, Inc. (ringbou ed., 2003). In some preferred embodiments, the host cell is a mammalian cell.

The term "nucleotide sequence," "nucleic acid sequence," "nucleic acid," or "polynucleotide sequence," refers to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Nucleic acid sequences can be, e.g., prokaryotic sequences, eukaryotic mRNA sequences, cDNA sequences from eukaryotic mRNA, genomic DNA sequences from eukaryotic DNA (e.g., mammalian DNA), and synthetic DNA or RNA sequences, but are not limited thereto.

The term "operably linked" or "operably associated" refers to functional linkage between genetic elements that are joined in a manner that enables them to carry out their normal functions. For example, a gene is operably linked to a promoter when its transcription is under the control of the promoter and the transcript produced is correctly translated into the protein normally encoded by the gene. Similarly, an enhancer element is operably associated with a gene of interest if it allows up-regulated transcription of the gene.

A "substantially identical" nucleic acid or amino acid sequence refers to a nucleic acid or amino acid sequence which comprises a sequence that has at least 75%, 80% or 90% sequence identity to a reference sequence as measured by one of the well known programs described herein (e.g., BLAST) using standard parameters. The sequence identity is preferably at least 95%, more preferably at least 98%, and most preferably at least 99%. In some embodiments, the subject sequence is of about the same length as compared to the reference sequence, i.e., consisting of about the same number of contiguous amino acid residues (for polypeptide sequences) or nucleotide residues (for polynucleotide sequences).

Sequence identity can be readily determined with various methods known in the art. For example, the BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad. Sci. USA 89:10915 (1989)). Percentage of sequence identity is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, unidirectional site-specific recombinases (or simply site-specific recombinases) refer to a group of recombinases from bacteria and unicellular yeasts. They encompass both tyrosine recombinases and the resolvase/invertase or serine recombinase family (e.g., phage integrases such as integrases from phages phiC31, R4, and TP-901). Tyrosine recombinases include tyrosine integrases (e.g., integrases from λ, HK022, P22, HP1 and L5) and other tyrosine recombinases (e.g., Cre and Flp). Examples of serine recombinases include serine integrases (e.g., integrases from phiC-31, R4, TP901) and other serine recombinases (e.g., γδ, Tn3, phage Mu recombinase).

Preferably, site-specific recombinases can include integrases (especially phage integrases) that mediate unidirectional site-specific recombination between two different DNA recognition sequences, the phage attachment site, attP, and the bacterial attachment site, attB. Integrases of the tyrosine family, e.g., lambda integrase, utilize a catalytic tyrosine to mediate strand cleavage, tend to recognize longer attP sequences, and require other proteins encoded by the phage or the host bacteria. Phage integrases from the serine family (e.g., phiC-31 phage integrase) are larger, use a catalytic serine for strand cleavage, recognize shorter attP sequences, and do not require host cofactors. Because the attB and attP sites are different sequences, recombination will result in a stretch of nucleic acids (called attL or attR for left and right) that is neither an attB sequence or an attP sequence, and is functionally unrecognizable as a recombination site to the relevant integrase enzyme, thus removing the possibility that the enzyme will catalyze a second recombination reaction that would reverse the first. This will result in a unidirectional site-specific integration event.

Phi-C31 integrase refers to a phage integrase which is capable of catalyzing in mammalian cells genomic recombination with high efficiency and tight sequence specificity. Functional characterization of this enzyme is described in the art, e.g., Kuhstoss and Rao, J. Mol. Biol. 222, 897-908, 1991; Rausch and Lehmann, Nucleic Acids Research 19, 5187-5189, 1991; and Groth et al., Proc. Natl. Acad. Sci. USA 97, 5995-6000, 2000.

The native attB and attP recognition sites of phage integrases (e.g., phage phi-C31 integrase) are generally about 34 to 40 nucleotides in length. See, e.g., FIG. 2 herein and also Groth et al., Proc. Natl. Acad. Sci. USA 97:5995-6000, 2000. These sites are typically arranged as follows: attB comprises a first DNA sequence attB5', a core region, and a second DNA sequence attB3', in the relative order from 5' to 3' attB5'-core region-attB3'. AttP comprises a first DNA sequence attP5', a core region, and a second DNA sequence attP3', in the relative order from 5' to 3' attP5'-core region-attP3'. The core region of attP and attB of Phi-C31 has the sequence 5'-TTG-3'.

A transgenic animal or plant refers to a non-human animal or a plant having a transgene or transgenic element integrated in the genome of one or more cells of the animal or the plant. The term encompasses animals or plants having all or nearly all cells containing a genetic modification (e.g., fully transgenic animals, particularly transgenic animals having a heritable transgene) as well as chimeric transgenic animals or plants, in which a subset of cells of the animal or plants are modified to contain the genomically integrated transgene. A transgenic plant or animal includes an individual animal or plant in all stages of development. For transgenic animals, farm animals (e.g., chickens, pigs, goats, sheep, cows, horses, rabbits and the like), rodents (such as mice), non-human primates (such as rhesus macaques) and domestic pets (e.g., cats and dogs) are considered herein. In some preferred embodiments, the animal is a mouse or a rat.

"Therapeutic genes" refer to polynucleotide sequences which encode molecules that provide some therapeutic benefit to the host, including proteins (e.g., secreted proteins, membrane-associated proteins (e.g., receptors), structural proteins, cytoplasmic proteins, and the like) functional RNAs (antisense, hammerhead ribozymes), and the like. Secreted proteins include those that may be found in a bodily fluid of a subject (e.g., in blood, lymph, saliva, gastrointestinal secretions, and the like). In some embodiments, the mammalian subject is a human subject and the introduced polynucleotide sequence encodes a human protein or other human gene product.

The term "vector" or "construct" refers to polynucleotide sequence elements arranged in a definite pattern of organization such that the expression of genes/gene products that are operably linked to these elements can be predictably controlled. Typically, they are transmissible polynucleotide sequences (e.g., plasmid or virus) into which a segment of foreign polynucleotide sequence can be spliced in order to introduce the foreign DNA into host cells to promote its replication and/or transcription.

A cloning vector is a polynucleotide sequence (typically a plasmid or phage) which is able to replicate autonomously in a host cell, and which is characterized by one or a small number of restriction endonuclease recognition sites. A foreign polynucleotide sequence fragment may be spliced into the vector at these sites in order to bring about the replication and cloning of the fragment. The vector may contain one or more markers suitable for use in the identification of transformed cells. For example, markers may provide tetracycline or ampicillin resistance.

An expression vector is similar to a cloning vector but is capable of inducing the expression of the polynucleotide sequence that has been cloned into it, after transformation into a host. The cloned polynucleotide sequence is usually placed under the control of (i.e., operably linked to) certain regulatory sequences such as promoters or enhancers. Promoter sequences may be constitutive, inducible or repressible.

III. Inserting Heterologous Polynucleotides at Native Chromosomal Integration Sites Described herein are several specific genes that contain native chromosomal integration sites which support stable and efficient expression of an inserted heterologous polynucleotide (exogenous gene or transgene). These native chromosomal integration sites are suitable for stable integration and/or expression of a heterologous polynucleotide in a host cell. For example, transgenes or recombinant genes encoding useful polypeptides (e.g., therapeutic or industrial proteins) can be so integrated and expressed in host cells. Additionally, theses sites can be employed for inserting site-specific recombination sequences (chromosomal landing pads) into a host genome. Host cells bearing such inserted chromosomal landing pads can in turn be used for insertion and expression of heterologous polynucleotides.

A native chromosomal insertion or integration site refers to a chromosomal location or site into which a heterologous polynucleotide can be integrated, e.g., via random integration, and which may occur naturally in the genome of a cell. In other words, the site is not introduced into the genome, for example, by recombinant means. Unless otherwise noted, the term as used herein specifically refers to a position in the genome that supports stable integration of foreign genes and their efficient transcription, and that is located within or adjacent to one of several genes in the CHO genome including: ankyrin 2 gene (Ank2), cleavage and polyadenylation specific factor 4 gene (Cpsf4), C-Mos gene and Mal gene also described herein as the Nephrocystin-1/Mal gene. It also encompasses chromosomal locations in the orthologs of these genes or homologous regions (as determined by sequence alignment) in other mammalian species (e.g., mouse, rat and human) with similar functions or activities.

As detailed herein, one specific native chromosomal insertion site is described herein for each of the four genes identified in the CHO genome (the "exemplified positions"; see FIGS. 3-6). However, the native chromosomal insertion sites considered herein are not limited to these specific positions. So long as stable integration and/or efficient transcription of an integrated heterologous polynucleotide is supported, the exact location of the native chromosomal insertion site with respect to the exemplified sites is not essential. Rather, the native chromosomal site can be at any position that is within or adjacent to one of the four genes. Whether a specific chromosomal location within or adjacent one of the four genes of interest supports stable integration and efficient transcription of an integrated foreign gene can be determined in accordance with standard procedures well known in the art or methods exemplified herein. In some preferred embodiments, the specific positions exemplified herein for CHO genome or corresponding positions (as determined by sequence alignment) in other mammalian genomes (e.g., mouse, rat or human genome) are employed as the native chromosomal insertion sites. In some other embodiments, the native chromosomal sites considered herein are preferably located close to one of the exemplified positions, e.g., within less than about 1 kb, 500 bp, 250 bp, 100 bp, 50 bp, 25 bp, 10 bp, or less than about 5 bp of one of the exemplified positions. In still some other embodiments, the employed native chromosomal site is located at about 1000, 2500, 5000 or more base pairs away from one of the exemplified positions.

A heterologous polynucleotide (e.g., a recombinant gene or a chromosomal landing pad) can be readily inserted into the native chromosomal integration sites described herein for stable integration and/or expression. The heterologous polynucleotide can be inserted into the native chromosomal integration sites of the host genome by various means, e.g., by homologous recombination or by using a hybrid recombinase that specifically targets sequences at the integration sites. For homologous recombination, homologous polynucleotide molecules line up and exchange a stretch of their sequences. A trans-gene can be introduced during this exchange if the trans-gene is flanked by homologous genomic sequences. For example, as described below, a chromosomal landing pad (an attP site-containing sequence) can be so inserted into the host genome at the native chromosomal integration sites.

Efficiency of homologous recombination in mammalian cells can be improved by introducing a break in the chromosomal region of homology. This can be achieved by targeting a nuclease to this region. For example, by using a DNA-binding protein that recognizes sequences in the native chromosomal location. One way to achieve this targeting is to use zinc-finger nucleases. These proteins have a modular composition and contain individual zinc finger domains, each of which can recognize a 3-nucleotide sequence in the target sequence (e.g., a native chromosomal integration site described above). Some embodiments can employ zinc finger nucleases with combinations of individual zinc finger domains that target numerous chromosomal locations. For example, the disclosed chromosomal sequences surrounding the exemplified integration sites in the Cpsf4, Ank2, C-Mos, and Nephrocystin-1/Mal genes contain 8, 6, 7, and 8 candidate sites, respectively, that can be targeted by an engineered zinc finger nuclease.

Other than homologous recombination, insertion of heterologous polynucleotides into the native chromosomal integration sites in or near the Cpsf4, Ank2, c-Mos, and Nephrocystin-1/Mal genes can also be accomplished via the use of a hybrid recombinase. The recombinant recombinase is an engineered protein that has a recombinase domain (e.g., from phiC31 integrase) linked to a DNA targeting domain (e.g. a zinc finger domain). Such a molecule can be targeted to a site contained in or near the Cpsf4, Ank2, c-Mos, and Nephrocystin-1/Mal genes. Such recombinant proteins would enable integration of a recombinant construct into these chromosomal locations. Advantages of this approach include the ability to target into cell lines without the necessity of prior introduction of a landing pad (as described below), and a higher efficiency than homologous recombination.

Although zinc finger proteins have been well studied for their ability to bind to DNA and are suitable for the above applications, it may be possible to specifically target the Cpsf4, Ank2, c-Mos, and Nephrocystin-1/Mal genes by using other approaches, for example by mutation of another type of DNA binding domain. Other DNA binding domains include leucine-zippers and helix-turn-helix structures. It may also be possible to specifically target the Cpsf4, Ank2, c-Mos, and Nephrocystin-1/Mal genes by using a nucleic acid moiety to base pair to sequences in these genes.

Some embodiments include the direct integration of a transgene into the native chromosomal integration sites by either homologous recombination or by using a hybrid recombinase. The transgene can be any recombinant gene that encodes a therapeutic or industrial protein, e.g., a hormone or an enzyme, as detailed below. Some other embodiments are directed to inserting one or more recombinase recognized site specific recombination sequences (chromosomal landing pads) into the native chromosomal integration sites disclosed herein. As detailed herein, the chromosomal landing pads stably inserted into the host genome can in turn be used for integrating and expressing transgenes in the host cell (e.g., a CHO cell or other mammalian cells). Engineered host cells bearing one or more chromosomal landing pads at the native chromosomal integration sites disclosed herein are useful for site-specific integration and stable expression of any desired target gene.

IV. Integrating Heterologous Polynucleotides Via Homologous Recombination

In one aspect, disclosed are methods and compositions for stably integrating heterologous polynucleotides into the native chromosomal integration sites via homologous recombination. Provided herein are polynucleotide molecules and vectors ("inserting vector") for inserting a heterologous polynucleotide (a transgene or a site-specific recombination sequence) into a host genome at the native chromosomal integration sites or specific chromosomal locations described herein. The polynucleotides and/or inserting vectors typically include a heterologous polynucleotide sequence (e.g., a recombinant gene or a chromosomal landing pad), a first homology arm, and a second homology arm. The polynucleotide or vector can additionally also include marker genes or sequences for positive and/or negative selections.

The heterologous polynucleotide sequence to be integrated into the host genome can encode any therapeutically or industrially useful proteins as described herein. It can also be a recombinase recognized integration site (chromosomal landing pad) which is then used for insertion and expression of a trangene, as detailed below. The first and the second homology arms are intended to target the heterologous polynucleotide sequence to a specific chromosomal location (e.g., a native chromosomal insertion site disclosed herein) for homologous recombination. As such, they are sequences that are substantially identical to the 5'- and the 3'-flanking sequences, respectively, of the native chromosomal integration site. As explained above, the native chromosomal integration sites are present within or adjacent to the coding or non-coding regions of one of the 4 specific genes, the Ank2 gene, the Cpsf4 gene, the C-Mos gene, and the Nephrocystin-1/Mal gene. Nephrocystin-1 gene is found 5' to the Mal gene. The insertion site can be 5' to the Mal gene between the Nephrocystin-1 and Mal genes. This genomic region is described herein as "Nephrocystin-1/Mal." As one can readily determine whether insertion of a heterologous polynucleotide at a given position in or around one of these genes leads to stable integration and/or expression, the exact position of the native chromosomal integration site with respect to each of the genes in the genome is not essential. Nevertheless, some preferred native chromosomal integration sites are described herein for Chinese hamster ovary (CHO) cells. As exemplified in the Examples below, the native chromosomal integration sites for CHO cells can be preferably between positions 130-131 of SEQ ID NO:1 for the Ank2 gene, between positions 629-630 of SEQ ID NO:2 for the Cpsf4 gene, between positions 272-273 of SEQ ID NO:3 for the C-Mos gene, between positions 239-240 of SEQ ID NO:4 for the Nephrocystin-1/Mal gene. The native chromosomal integration sites for CHO cells can also be between positions 26,123-175,773 of NCBI No. NW_003615916.1 for the Ankyrin 2 gene (between positions 23 and 152,773 of SEQ ID NO: 9) or between nucleotides 844-845 of NCBI No. NW_003635654.1 for the Ankyrin2 gene (SEQ ID NO: 10), between positions 858,966-859,967 of NCBI NW_003614125.1 for the Cpsf4 gene (positions 966-967 of SEQ ID NO: 11) or between positions 858,533-859,237 of NCBI NW_003614125.1 for the Cpsf4 gene (positions 533-1237 of SEQ ID NO: 11), between positions 400,355-400,356 of NCBI NW_003614707.1 for the C-Mos gene (positions 355-356 of SEQ ID NO: 12) or between positions 398,595-399,212 of NCBI NW_003614707.1 for the C-Mos gene (SEQ ID NO: 12), and between positions 1,578,738-1,578,739 of NCBI NW_003613665.1 for the Nephrocystin-1/Mal gene (positions 738-739 of SEQ ID NO: 13) or between positions 1,574,453-1,625,306 of NCBI NW_003613665.1 for the Nephrocystin-1/Mal gene (SEQ ID NO: 13). The sequences and NCBI Reference numbers are incorporated by reference in their entirety.

It should be appreciated that the native chromosomal integration sites can also vary from cell line type to cell line type. For example, the nucleotide sequence of Ank2 gene of the CHO DG44 cell line can differ from the nucleotide sequence of the Ank2 gene of the CHO-K1 cell line as can the exact location of the native chromosomal integration site of the two cell line types. Thus, in some embodiments, the chosen native chromosomal integration sites for inserting a heterologous nucleotide sequence (a transgene or a chromosomal landing pad) can be at or close to each of these specific positions in CHO genome. Preferred native chromosomal integration sites between cell line type or for other mammalian cells (e.g., mouse cell, rat cell and human cell) can be determined based on sequence homology among the same gene in different mammalian species.

Once the exact native chromosomal integration site for inserting a heterologous polynucleotide sequence is determined, the homology arms which are substantially identical to the flanking sequences can then be readily designed and synthesized. Length of the homology arms is not essential, as long as they are capable of directing the homologous recombination at the desired site. Thus, the homology arms can be sequences comprising at least 10 bp, 25 bp, 50 bp, 100 bp, 200 bp, 500 bp, 1 kb, 2, kb, 5 kb, 10 kb or more contiguous nucleotide pairs of the sequences that flank the desired native chromosomal insertion site. In some embodiments, the homology arms comprise sequences identical to sequences that flank one of the exemplified chromosomal insertion sites in CHO genome (FIGS. 3-6) or corresponding positions (as determined by sequence alignment) in other mammalian genomes. In some other embodiments, sequences that are substantially identical (e.g., at least 75%, 80%, 90%, 95% or 99% identical) to the flanking sequences of the native integration sites are employed as the homology arms in the polynucleotide molecules and vectors described herein. For example, the homology arms can include part or all of the sequences flanking the exemplified native integration site in each of these genes in CHO cells as shown in FIGS. 3-6.

The genes (Ank2, Cpsf4, C-Mos gene, and Nephrocystin-1/Mal gene) in cells from various species (e.g., CHO cells) have also been described in the art. For example, human Ank2 gene (accession nos. NG_009006; NW_003615916.1; NW_003635654.1), Cpsf4 gene (accession nos. EF191081; NW_003614125.1), C-Mos gene (Neel et al., Proc. Natl. Acad. Sci. USA, 79: 7842-6, 1982; and Morris et al., Hum. Genetics 81:339-342; accession no. NW_003614707.1), Nephrocystin-1/Mal gene (Alonso et al., Proc. Natl. Acad. Sci. USA 84:1997-2001, 1987; and Rancano et al., J. Biol. Chem. 269:8159-8164, 1994; accession no. NW_003613665.1) have all been characterized in the art. A skilled artisan can readily design and synthesize appropriate homology arm sequences for various applications. As exemplified in the Examples, sequences flanking one of the identified integration sites with a length of about 1 kb to 5 kb can be employed as the homology arms of the inserting vector for homologous integration of a heterologous polynucleotide (e.g., a landing pad) into a host genome. In some embodiments, the entire gene loci can be employed. In other embodiments, the entire gene loci plus 1, 2 or more kb on at least one of the 5' and 3' ends can be employed. In some embodiments, such as for Cpsf4 gene and C-Mos gene, the entire gene loci plus 2 kb on each of the 5' and 3' ends can be employed. In other embodiments, such as for Nephrocystin-1/Mal gene and Ankyrin-2 gene, the entire gene loci can be employed.

In some specific embodiments, the heterologous polynucleotide sequence to be integrated into a host genome is site-specific recombination sequence that is recognized by a site-specific recombinase, e.g., a phage integrase such as the phiC-31 phage integrase. The site-specific recombination sequences to be inserted into the native chromosomal integration sites can be any sequence that supports site-specific recombination and is recognized by a unidirectional site-specific recombinase. Preferably, the site-specific recombination sequence comprises the phage attachment site (e.g., attP site) or the bacterial attachment site (e.g., attB site) recognized by an integrase (e.g., a tyrosine integrase or a serine integrase). Examples of such sequences include attB and attP sequences (as well as pseudo att sites) recognized by several phage integrases, e.g., phiC-31 integrase or λ integrase. Suitable recombination sites also include sequences that are recognized by mutant integrases. During the integration of the phage genome into the genome of its host (e.g., an *E. coli* cell), the enzyme catalyzes the DNA exchange between the attP site of the phage genome and the attB site of the bacterial genome, resulting in the formation of attL and attR sites. By inserting into the host genome (e.g., at the native chromosomal integration sites disclosed herein) a site-specific recombination site (e.g., attP site) that is recognized by a phage integrase (e.g., phiC-31 integrase), a heterologous polynucleotide attached to the cognate recognition site (e.g., attB site) can be readily inserted into the host genome via site-specific recombination catalyzed by the phage integrase.

The phage attachment site (attP) and the bacterial attachment site (attB site) recognized by any site-specific recombinase (e.g., serine or tyrosine phage integrases) may be employed as the site-specific recombination sequence described herein. These include both the wildtype (native) attB and attP sites recognized by a given phage integrase as well as pseudo sites. Site-specific recombinases and their respective recognition sequences (attP and attB sites) for various phages and other species have been known and characterized in the art. Examples include λ phage integrase (Enquist et al., Cold Spring Harbor Symp. Quant. Biol. 43:1115-1120, 1979), HK022 phage integrase (Yagil et al., J. Mol. Biol. 207:695-717, 1989), P22 phage integrase (Leong et al., J. Biol. Chem. 260:4468-4477, 1985), HP1 phage integrase (Waldman et al., J. Bacteriol. 165:297-300, 1986), L5 phage integrase (Lee et al., J. Bacteriol. 175:6836-6841, 1993), phiC-31 phage integrase (Kuhstoss and Rao, J. Mol. Biol. 222:897-908, 1991), R4 phage (Groth et al., Proc. Natl. Acad. Sci. USA 97:5995-6000, 2000), TP901 phage integrase (Christiansen et al., J. Bacteriol. 178:5164-5173, 1996), γδ transposon resolvase (Reed et al., Nature 300:381-383, 1982), Tn3 transposon resolvase (Krasnow et al., Cell 32:1313-1324, 1983) and Mu phage invertase Gin (Kahmann et al., Cell 41:771-780, 1985).

Other than wild type recombination sites that are recognized by site-specific recombinases, the site-specific recombination sequence present in the polynucleotide molecules or vectors for landing pad insertion can also comprise a sequence that is different from the wild-type recognition site (e.g., wild type attP site) by at least one base pair alteration (a substitution, deletion or insertion). Sequence alterations may be at any position within the site-specific recombination sequence. In some embodiments, the modified site-specific recombination sequences have multiple sequence alterations as compared to a wild type recognition site. When such a modified site-specific recombination sequence (e.g., a modified attP site) is integrated into the genome of an engineered host cell as described herein, the wild type or mutant version of the corresponding integrase (e.g., a mutant phi-C31 integrase) may be needed in order to incorporate a heterologous polynucleotide or transgene into the recombination site. Various mutant integrases (e.g., mutant phiC-31 integrase) are also known in the art. See, e.g., Smith et al., Nuc. Acids Res. 32, 2607-2617, 2004; and Kevarala et al., Mol. Ther. 17, 112-120, 2008.

For inserting a heterologous polynucleotide sequence (a transgene or a chromosomal landing pad) into the genome of a host cell, the polynucleotide described above is typically present in a vector ("inserting vector"). These vectors are typically circular and linearized before used for homologous recombination. In addition to the homology arms and the heterologous polynucleotide (e.g., a landing pad), the vectors may also contain markers suitable for selection or screening, an origin of replication, and other elements. As exemplified in the Examples herein, the vector can contain both a positive selection marker and a negative selective marker. The positive selection marker, e.g., an antibiotic resistance gene, is used to identify host cells into which the vector has stably integrated. Examples of such markers include antibiotic resistance genes for neomycin, blasticidin, hygromycin and ZEOCIN™. The negative selection marker, e.g., a suicide gene, serves to eliminate cells that have randomly integrated the vector sequence while retaining cells that have undergone homologous recombination at the desired location. An Example of such negative selection marker is the HCV-TK gene as exemplified in the Examples herein. The positive screening marker (e.g., enhanced green fluorescent protein) is used to identify host cells into which the vector has stably integrated (e.g., by using fluorescently activated cell sorting, FACS). The negative screening marker, e.g., cyan fluorescent protein, is used to identify cells (e.g., by FACS) that have randomly integrated the vector sequence. FACS for cells containing the positive screening marker but lacking the negative screening marker will identify cells that have undergone homologous recombination at the desired location.

One more component of the inserting vector (as well as the targeting vector described below) is an origin of replication. Replication origins are unique DNA segments that contain multiple short repeated sequences that are recognized by multimeric origin-binding proteins and that play a key role in assembling DNA replication enzymes at the origin site. Suitable origins of replication for use in the vectors include, e.g., EBV oriP, SV40, *E. coli* oriC, colE1 plasmid origin, ARS, and the like. Another useful element in an expression vector is a multiple cloning site or polylinker. Synthetic DNA encoding a series of restriction endonuclease recognition sites is inserted into a plasmid vector, for example, downstream of the promoter element. These sites are engineered for convenient cloning of DNA into the vector at a specific position.

The polynucleotides or vectors for inserting the heterologous polynucleotide into a host genome can be readily constructed in accordance with standard procedures known in the art of molecular biology (e.g., Sambrook et al., supra; and Brent et al., supra) and the disclosure herein. To generate the vectors, the above-described polynucleotides comprising the homology arms and the heterologous polynucleotide sequence (e.g., a transgene or a chromosomal landing pad) can be inserted into various known plasm ids for transfecting mammalian host cells. Such known plasmids include, e.g., BPV, EBV, vaccinia virus based vector, SV40, 2-micron circle, pcDNA3.1, pcDNA3.1/GS, pYES2/GS, pMT, p IND, pIND(Sp1), pVgRXR (Invitrogen), and the like, or their derivatives. These plasmids are all described and well known in the art (Botstein et al., Miami Wntr. SyTnp. 19:265-274, 1982; Broach, In: *The Molecular Biology of the Yeast Saccharomyces: Life Cycle and Inheritance*, Cold Spring Harbor Laboratory, Cold Spring Harbor, N.Y., p. 445-470, 1981; Broach, *Cell* 28:203-204, 1982; Dilon et al., J. Clin. Hematol. Oncol. 10:39-48, 1980; and Maniatis, In: *Cell Biology: A Comprehensive Treatise*, Vol. 3, Gene Sequence Expression, Academic Press, NY, pp. 563-608, 1980.

V. Engineered Cells with Integrated Heterologous Polynucleotides

Provided herein are recombinant or engineered host cells which contain heterologous polynucleotides (recombinant genes or chromosomal landing pads) that are stably integrated into the genome at one or more of the native chromosomal integration sites disclosed herein. Cells with recombinant genes integrated at the disclosed sites will allow stable and strong expression of polypeptides encoded by the genes. Cells with integrated chromosomal landing pads allow for efficient site-specific integration and/or expression of a target polynucleotide or gene of interest. Engineered host cells can also include cells which bear such inserted chromosomal landing pads and which then have one or more transgenes integrated into the landing pads, as explained below. Using the polynucleotide molecules or inserting vectors described above, various cells can be modified by inserting recombinant genes or chromosomal landing pads at one or more of the specific chromosome locations described herein.

The recombinant polynucleotides or inserting vectors described above (or targeting vectors described below) can be introduced into an appropriate host cell (e.g., a mammalian cell such as CHO cell) by any means known in the art. Typically, after appropriate restriction enzyme digestion to generate free ends of homology to the host chromosome, the polynucleotide can then be transfected into host cells. The linearized inserting vectors can be introduced into the host cell by standard protocols routinely practiced in the art. For example, the vector can be transfected into the host cell by calcium phosphate co-precipitation, by conventional mechanical procedures such as microinjection or electroporation, by insertion of a plasmid encased in liposomes, and by virus vectors. These techniques are all well known and routinely practiced in the art, e.g., Freshney, supra; Sambrook et al., supra; and Brent et al., supra). Host cells which harbor the transfected recombinant inserting vector can be identified and isolated using the selection marker present on the vector. Large numbers of recipient cells may then be grown in a medium which selects for vector-containing cells.

Figure 2:
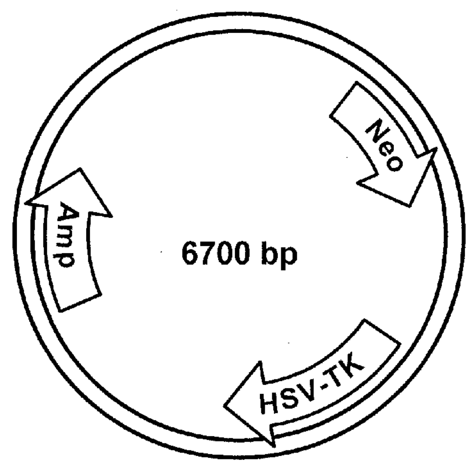
FIG. 2 illustrates the plasmid used for introducing an attP site into identified native chromosomal insertion sites in CHO genome. The attP site is in the 5' of Neo gene. The left-homology arm is cloned 5' of attP and Neo gene; the right-homology arm is cloned at 3' of Neo gene. The HSV-TK gene is used for negative selection. The sequences shown are the double strand sequences of the attP and attB sites recognized by phi-C31 phage integrase: attP (SEQ ID NO:5 and SEQ ID NO:6), attB (SEQ ID NO:7 and SEQ ID NO:8).

A specific vector for inserting a site-specific recombination sequence (i.e., attP sequence) into a native chromosomal insertion site is exemplified herein (FIG. 2). In addition to the attP sequence, the vector bears homology arms which support homologous recombination at the noted native chromosomal insertion site and also selection markers. For integrating into the CHO genome at the desired native insertion site, the vector was first linearized via restriction digestion. After transfecting the linearized sequence into a host cell (e.g., CHO cell), the cells are then subjected to positive and negative selections to identify cells which have integrated site-specific recombination site (attP site) via homologous recombination. Cells thus identified can then be further examined to ascertain integration of the heterologous polynucleotide at the chosen native chromosomal insertion site. As disclosed herein, cells with integrated recombinant genes can be directly used for production of therapeutic or industrial proteins encoded by the genes. Alternatively, cells with inserted chromosomal landing pads can be employed for production of a target polypeptide by integrating into the chromosomal landing pad a polynucleotide sequence that encodes the target polypeptide.

Preferably, host cells for inserting one or more heterologous polynucleotides at the native chromosomal insertion sites are eukaryotic cells. Eukaryotic vector/host systems, and mammalian expression systems in particular, allow for proper post-translational modifications of expressed mammalian proteins to occur, e.g., proper processing of the primary transcript, glycosylation, phosphorylation and advantageously secretion of expressed product. Therefore, eukaryotic cells such as mammalian cells are the preferred host cells for inserting the heterologous polynucleotides (recombinant genes or chromosomal landing pads) at the native chromosomal locations described herein. Suitable cells include both animal cells (such as cells from insect, rodent, cow, goat, rabbit, sheep, non-human primate, human, and the like) and plant cells (such as rice, corn, cotton, tobacco, tomato, potato, and the like). Specific examples of such host cell lines include CHO, BHK, HEK293, VERO, HeLa, COS, MDCK, PER.C6, and W138.

In some embodiments, provided are recombinant cells which have a polynucleotide of interest or transgene already stably integrated into a landing pad that has been pre-inserted at a native chromosomal location described herein. Targeting vectors for integrating a target polynucleotide into a chromosomal landing pad that has already been inserted into the host genome are described in more detail below. As described herein, the landing pad comprises a recognition sequence (e.g., attP site) that is recognized by a site-specific recombinase (e.g., a phage integrase such as phi-C31 integrase). By attachment to a cognate recognition sequence (e.g., attB site) that is also recognized by the recombinase, the polynucleotide of interest along with appropriate transcription regulatory elements are integrated into the landing pad via site-specific recombination mediated by the recombinase. The integrated polynucleotides of interest in the recombinant cells can encode any protein or polypeptide useful in industrial or therapeutic applications. Specific examples of such polypeptides and proteins are described above. These include e.g., enzymes (e.g., proteases, phospholipases, and the like), protease inhibitors, hormones (e.g., pituitary hormones), growth factors, cytokines, chemokines, chemotactins, gonadotrophins, lipid-binding proteins, somatamedians, gonadotrophins, and immunoglobulins. Other proteins of interest include antimicrobial polypeptides (e.g., antibacterial, antifungal, antiviral, and/or antiparasitic polypeptides), and antibodies or antigen-binding antibody fragments (e.g, FAbs) thereof (e.g., orthoclone OKT-e (anti-CD3), GPIIb/IIa monoclonal antibody).

Other than mammalian cells, the host cell for inserting heterologous polynucleotides as described herein may also be a yeast cell or a plant cell. Yeast or plant cells thus engineered are suitable for stable integration and expression of a transgene that is introduced into the host via a yeast or plant expression vector. Examples of suitable inset cells include cells from *Drosophila* larva. When insect cells are used, the heterologous polynucleotides can be introduced into the cells via appropriate inserting vectors. For example, baculovirus vectors can be employed as described in the art (Jasny, Science 238:1653, 1987; and Miller et al., In: *Genetic Engineering* (1986), Setlow, J. K., et al., eds., Plenum, Vol. 8, pp. 277-297). When insect cells are employed as hosts, the *Drosophila*-alcohol dehydrogenase promoter can optionally be used in the inserting vector for inserting the heterologous polynucleotides (Rubin, *Science* 240:1453-1459, 1988).

VI. Integrating Target Polynucleotides into Chromosomal Landing Pads

As described above, a target polynucleotide or transgene encoding a polypeptide (i.e., a "polynucleotide of interest" or a "gene of interest") can be directly integrated into the native chromosomal integration sites disclosed herein. Stable and efficient expression and production of any of the therapeutic or industrial proteins described below can be achieved in this manner. Alternatively, a target polynucleotide can be integrated into a host genome via a chromosomal landing pad that has already been inserted at a native chromosomal integration site disclosed herein. Employing engineered host cells bearing inserted chromosomal landing pads described herein, also provided are vectors ("targeting vector") and methods for integrating and expressing a heterologous polynucleotide or transgene in the cell. Polynucleotides of interest that encode various useful target polypeptides can be stably integrated into the genome of an engineered host cell described herein. The polynucleotides of interest can be either endogenous or exogenous to the host cell. An exogenous polynucleotide is a nucleic acid molecule having a sequence that is not naturally present in the host cell while an endogenous polynucleotide is a nucleic acid molecule with a sequence that pre-exists in the host cell. Many specific examples of proteins or polypeptides that can be expressed are described below.

Depending on the engineered host to be used, a variety of targeting vectors are suitable for use. As the preferred host cell bearing the inserted chromosomal landing pad is a mammalian cell (e.g., CHO cell), the targeting vector is preferably a vector for eukaryotic expression. In general, the targeting vector will have the gene of interest attached to a cognate recombination site or a recognition sequence. The cognate recombination site on the vector is also recognized by the site-specific recombinase (e.g., phiC-31 integrase) which recognizes the inserted chromosomal landing pad. As such, the cognate recombination site on the vector will support the recombinase mediated integration of the target polynucleotide into the landing pad. For example, for integration and expression in an engineered host cell bearing an inserted phage attachment site (attP) of a specific phage integrase, the vector will have the target polynucleotide attached to the cognate bacterial attachment site (attB site) which is also recognized by the same integrase. Similarly, if the inserted landing pad comprises the attB site of a phage integrase, the targeting vector will comprise the cognate attP site recognized by the integrase. Some phage integrases, such as phiC31 and R4, prefer to integrate into phage attachment sites (attP sites) rather than bacterial attachment sites. With these enzymes, the targeting vector should carry the attB site while the landing pad should comprise the attP site. Other phage integrases preferentially integrate into bacterial attachment sites (e.g., pseudo attB), rather than phage attachment sites. Examples of enzymes with this preference are phiBT1 integrase and A118 integrase. When these integrases are used, the target vector should carry the attP site instead of the attB site while the corresponding host cell should contain the attB site in the inserted landing pad.

To support expression of the target polynucleotide upon integration at the landing pad, the targeting vector can also contain promoter sequence and other transcription regulatory elements (e.g., enhance sequences) that is operably linked to the target polynucleotide. In general, promoters can be selected such that they are functional in the cell type into which they are being introduced. Many promoters known in the art can be used for expression in mammalian host cells. Examples include, but are not limited to, the promoter of the mouse metallothionein I gene sequence (Hamer et al., *J. Mol. Appl. Gen.* 1:273-288, 1982); the TK promoter of Herpes virus (McKnight, *Cell* 31:355-365, 1982); the SV40 early promoter (Benoist et al., *Nature* (*London*) 290:304-310, 1981); the yeast gall gene sequence promoter (Johnston et al., *Proc. Natl. Acad. Sci.* (*USA*) 79:6971-6975, 1982); Silver et al., *Proc. Natl. Acad. Sci.* (*USA*) 81:5951-59SS, 1984), the CMV promoter, the EF-1 promoter, the actin promoter, the phosphoglycerate kinase promoter, the ubiquitin promoter and the thymidine kinase promoter, the ecdysone-responsive promoter(s), tetracycline-responsive promoter, and the like.

In addition, the targeting vector can have selection or screening marker sequences, an origin of replication, and the like. As with markers used in the inserting vectors described above, the selection or screening markers in the targeting vectors also provide a means to select or screen for growth of only those cells that contain the vector. Such selection markers are typically of two types: drug resistance and auxotrophic. A drug resistance marker enables cells to detoxify an exogenously added drug that would otherwise kill the cell. Auxotrophic markers allow cells to synthesize an essential component (usually an amino acid) while grown in media that lacks that essential component. Common selectable marker genes include those for resistance to antibiotics such as ampicillin, tetracycline, kanamycin, bleomycin, streptomycin, hygromycin, neomycin, ZEOCIN™, G418, and the like. Selectable auxotrophic genes include, for example, hisD, that allows growth in histidine free media in the presence of histidinol.

The selection marker sequences and the transcription regulatory elements should be linked to the target polynucleotide and the cognate recombinase recognition sequence in the vector in such a way that they will co-integrate with the target polynucleotide into the host genome once site-specific recombination at the landing pad takes place. The targeting vectors described herein can be constructed utilizing methodologies known in the art of molecular biology in view of the teachings of the specification. See, e.g., Sambrook et al., *Molecular Cloning: A Laboratory Manual*, Cold Spring Harbor Press ($3^{rd}$ ed., 2001); Brent et al., *Current Protocols in Molecular Biology*, John Wiley & Sons, Inc. (ringbou ed., 2003); and Freshney, *Culture of Animal Cells: A Manual of Basic Technique*, Wiley-Liss, Inc. ($4^{th}$ ed., 2000). Typically, the targeting vectors are assembled by inserting into a suitable vector backbone a recombination site cognate to the landing pad, polynucleotides of interest, sequences encoding selection markers, and other optional elements described herein.

In addition to an engineered host cell bearing an inserted chromosomal landing pad and the targeting vector, site specific integration of the target polynucleotide at the landing pad (e.g., an attP site) will also require catalytic activities of the corresponding recombinase (e.g., a phage integrase such as phiC-31 integrase). The recombinase (e.g., phiC-31 integrase) can be introduced into a target cell before, concurrently with, or after the introduction of a targeting vector. As explained above, various phage integrases are considered herein. The specific integrase used in integrating a target polynucleotide into an engineered host cell should correspond to and recognize the site-specific recombination sequence in the landing pad of the host genome and the cognate recognition sequence in the targeting vector. In some embodiments, the unidirectional site-specific recombinase is a serine integrase. Serine integrases that may be useful for in vitro and in vivo recombination include, but are not limited to, integrases from phages phi-C31, R4, TP901-1, phiBT1, Bxb1, RV-1, A118, U153, and phiFC1, as well as others in the long serine integrase family. See, e.g., Gregory et al., *J. Bacteriol.,* 185:5320-5323, 2003; Groth and Calos, *J. Mol. Biol.* 335:667-678, 2004; Groth et al., *Proc. Natl. Acad. Sci.* 97:5995-6000, 2000; Olivares et al., *Gene* 278:167-176, 2001; Smith and Thorpe, *Molec. Microbiol.,* 4:122-129, 2002; and Stoll et al., *J. Bacteriol.,* 184:3657-3663, 2002. In addition to these wild-type integrases, altered integrases that bear mutations are also known in the art (see, e.g., Sclimenti et al., *Nuc. Acid Res.* 29:5044-5051, 2001). Such integrases with altered activity or specificity compared to the wild-type are also useful for the recombination reaction and the integration of target polynucleotides into an engineered host genome.

In some embodiments, a purified enzyme polypeptide is introduced into the host cell to mediate the integration of the targeting vector. Methods of introducing functional proteins into cells are well known in the art. For example, a phage integrase polypeptide such as phiC-31 integrase can be directly introduced into a cell by many means, including liposomes, coated particles, whiskers, microinjection, electroporation, and peptide transporters (see, e.g., Siprashvili et al., *Mol. Ther.,* 9:721-728, 2004). In some other embodiments, a polynucleotide encoding the integrase can be introduced into the cell using a suitable expression vector. The integrase can be expressed from the same targeting vector expressing the gene of interest. Alternatively, polynucleotide encoding the integrase can be introduced into the host cell via a second vector. In some embodiments, a DNA sequence encoding the integrase is introduced into the host cell on an expression vector. This can be performed as described in the art, e.g., Olivares et al., *Gene,* 278:167-176, 2001; and Thyagarajan et al., *Mol. Cell. Biol.* 21:3926-3934, 2001. In some other embodiments, the site specific integration relies on transient presence of a RNA molecule encoding the recombinase polypeptide. For example, an mRNA molecule encoding a phage integrase can be introduced into and expressed in a host cell as described in, e.g., Groth et al., *J. Mol. Biol.* 335:667-678, 2004; and Hollis et al., *Repr. Biol. Endocrin.* 1:79, 2003. It is generally preferred that the integrase be present for only such time as is necessary for insertion of the targeting vector into the genome of the engineered host cell. Introduction of integrase-encoding RNA (e.g., an mRNA) can ensure transient expression and removes the possibility that an integrase-encoding nucleic acid will become permanently incorporated into a target genome. Transient expression of the site-specific recombinase can also be achieved via other means. For example, polynucleotide expressing the enzyme can be placed under the control of a regulatable promoter (i.e., a promoter whose expression can be selectively induced or repressed).

Any convenient protocol may be employed for in vitro or in vivo introduction of the targeting vector and/or a second vector expressing a phage integrase into the target cell, depending on the location of the target cell. For example, where the engineered host cell is an isolated cell, the targeting vector may be introduced directly into the cell under cell culture conditions permissive of viability of the target cell, e.g., by using standard transformation techniques. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being transformed and the circumstances 'under which the transformation is taking place (i.e. in vitro, ex vivo, or in vivo). A general discussion of these methods can be found in, e.g., Brent et al, supra.

Alternatively, where the engineered host cell or cells are part of a multicellular organism, the targeting vector may be administered to the organism or host in a manner such that the targeting vector is able to enter the host cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body. Methods for the administration of nucleic acid constructs are well known in the art. For example, nucleic acid constructs can be delivered with cationic lipids (Goddard, et al, *Gene Therapy,* 4:1231-1236, 1997; Gorman et al., *Gene Therapy* 4:983-992, 1997; Chadwick et al., *Gene Therapy* 4:937-942, 1997; Gokhale et al., *Gene Therapy* 4:1289-1299, 1997; Gao and Huang, *Gene Therapy* 2:710-722, 1995), using viral vectors (Monahan et al., *Gene Therapy* 4:40-49, 1997; Onodera et al., *Blood* 91:30-36, 1998), by uptake of "naked DNA", and the like. Techniques well known in the art for the transfection of cells (see discussion above) can be used for the ex vivo administration of nucleic acid constructs. The exact formulation, route of administration and dosage can be chosen empirically. See e.g. Fingl et al., 1975, in *The Pharmacological Basis of Therapeutics*, Ch. 1 p 1).

VII. Target Polypeptides or Proteins to be Expressed with Engineered Host Cells

The engineered host cells described above are useful for stable expression of any polynucleotide of interest. The polynucleotides of interest can encode various polypeptides with medical or industrial applications. In some embodiments, the target polynucleotide or polynucleotide of interest to be integrated into the landing pad in the engineered host cell can be one that encodes a therapeutic protein. Examples of therapeutic proteins include factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, interleukins, cytokines, small peptides, and the like. Other therapeutic proteins that can be expressed from an intergrated target polynucleotide in the engineered host cell can include, e.g., Herceptin®, polypeptide antigens from various pathogens such as disease causing bacteria or viruses (e.g., *E. coli, P. aeruginosa, S. aureus*, malaria, HIV, rabies virus, HBV, and cytomegalovirus), and other proteins such as lactoferrin, thioredoxin and beta-caseinvaccines.

Additional examples of proteins of interest include, but are not necessarily limited to insulin, erythropoietin, tissue plasminogen activator (tPA), urokinase, streptokinase, neutropoesis stimulating protein (also known as filgastim or granulocyte colony stimulating factor (G-CSF)), thrombopoietin (TPO), growth hormone, emoglobin, insulinotropin, imiglucerase, sarbramostim, endothelian, soluble CD4, and antibodies and/or antigen-binding fragments (e.g, FAbs) thereof (e.g., orthoclone OKT-e (anti-CD3), GPIIb/IIa monoclonal antibody), liary neurite transforming factor (CNTF), granulocyte macrophage colony stimulating factor (GM-CSF), brain-derived neurite factor (BDNF), parathyroid hormone (PTH)-like hormone, insulinotrophic hormone, insulin-like growth factor-1 (IGF-1), platelet-derived growth factor (PDGF), epidermal growth factor (EGF), acidic fibroblast growth factor, basic fibroblast growth factor, transforming growth factor β, neurite growth factor (NGF), interferons (IFN) (e.g., IFN-α2b, IFN-α2a, IFN-αN1, IFN-β1b, IFN-γ), interleukins (e.g, IL-1, IL-2, IL-8), tumor necrosis factor (TNF) (e.g, TNF-α, TNF-β), transforming growth factor-α and -β, catalase, calcitonin, arginase, phenylalanine ammonia lyase, L-asparaginase, pepsin, uricase, trypsin, chymotrypsin, elastase, carboxypeptidase, lactase, sucrase, intrinsic factor, vasoactive intestinal peptide (VIP), calcitonin, Ob gene product, cholecystokinin (CCK), serotonin, and glucagon.

Suitable polypeptides of interest that can be expressed from the integrated target polynucleotides also include specific membrane proteins or other intracellular proteins. Examples of membrane proteins include, but are not necessarily limited to adrenergic receptors, serotonin receptors, low-density lipoprotein receptor, CD-18, sarcoglycans (which are deficient in muscular dystrophy), etc. Useful intracellular proteins include proteins that are primarily located within the intracellular compartment or which exhibit a desired biological activity within a cell. Such intracellular proteins can include fumarylacetoacetate hydrolase (FAH) which is deficient in subjects with hereditary tyrosinemia Type 1. Other specific examples of intracellular proteins include antiviral proteins (e.g., proteins that can provide for inhibition of viral replication or selective killing of infected cells), structural protein such as collagens, i.e. the type VII collagen COL7A1 gene, defective in Recessive Dystrophic Epidermolysis Bullosa (RDEB) and dystrophin, defective in muscular dystrophy.

VIII. Kits and Transgenic Animals with Integrated Transgenes

Provided herein are kits for using the engineered host cells described above. The kits enable a skilled artisan to site-specifically integrate and/or express a heterologous polynucleotide in an engineered host cell which bears a target transgene or an inserted chromosomal landing pad at one or more native chromosomal integration sites disclosed herein. Some kits described herein contain engineered host cells (e.g., CHO cells) which have a target polynucleotide directly inserted at a native chromosomal integration site in the genome. Some other kits contain engineered host cells which have a target polynucleotide inserted at one or more chromosomal landing pads that have been pre-integrated into native chromosomal integration sites in the genome. Still some other kits described herein contain recombinant cells with inserted chromosomal landing pad at one or more native chromosomal integration sites and other reagents for inserting a target polynucleotide into the chromosomal landing lads.

As exemplification, some kits described herein contain at least one or more of the following components, an engineered host cell (e.g., a CHO cell line) bearing an inserted landing pad (e.g., an attP site) at one or more of the native chromosomal locations described herein, a targeting vector for cloning and integrating a heterologous polynucleotide, and an integrase component (e.g., phiC-31). The kits can optionally also contain a target polynucleotide that is to be cloned into the targeting vector and expressed in the host cell. Typically, upon cloning into the targeting vector, the heterologous target polynucleotide is attached to a cognate sequence (e.g., an attB site) also recognized by the integrase for integrating at the inserted landing pad. As described herein, the integrase component can be provided in any suitable form (e.g., as a protein formulated for introduction into a target cell or in an integrase vector which provides for expression of the desired integrase following introduction into the engineered host cell). Thus, some kits can comprise a substantially purified recombinase polypeptide (e.g., phiC-31). Some other kits can contain a second vector that allows expression of the enzyme in the host cell. The kits described herein can optionally contain other components, e.g., restriction enzymes for cloning a targeting polynucleotide, control plasmids, buffers, and etc. The various components of the kit may be present in separate containers or certain compatible components may be pre-combined into a single container, as desired.

In addition to the various reagents, the kits described herein typically further include instructions for using the components of the kit in integrating and expressing a polynucleotide of interest. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging). In other embodiments, the instructions are present as an electronic storage data file present on a suitable computer readable storage medium, e.g. CD-ROM, diskette, etc. In yet some other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

Further provided herein are transgenic non-human animals or plants whose genomes have been modified by inserting a heterologous polynucleotide (a transgene or a chromosomal landing pad) at one or more native chromosomal integration sites disclosed herein. The transgenic non-human animals or plants can also have a genome which has inserted chromosomal landing pads and then further modified by integrating one or more target polynucleotides at the inserted landing pads. Examples of transgenic animals that can be produced with methods described herein include mice, rats, chickens, cats, dogs, rabbit, pigs, goats, sheep, cows, horses, as well as non-human primates such as rhesus macaques. The transgenic non-human animals or plants described herein can be produced by integrating a heterologous polynucleotide or transgene into the genome at one or more of the native chromosomal integration sites. Other transgenic animals or plants are produced by integrating a target polynucleotide into a chromosomal landing pad that has already been inserted into the genome as described herein. The target cell can be any cell amenable to genetic modification using the systems and methods described herein, and which is suitable to produce a transgenic animal described herein. Target cells can be isolated (e.g., in culture) or in a multicellular organism (e.g., in a blastocyst, in a fetus, in a postnatal animal, and the like). Exemplary target cells include, but are not necessarily limited to, primary cells, secondary cells, transformed cells, egg cells, fertilized egg cells, single cell embryos, somatic cells (e.g., muscle, bone, cartilage, ligament, tendon, skin (dermis, epidermis, and the like), cells of the viscera (e.g., lung, liver, pancreas, gastrointestinal tract (mouth, stomach, intestine), and the like), stem cells (e.g., embryonic stem cells (e.g., cells having an embryonic stem cell phenotype), adult stem cells, pluripotent stem cells, hematopoietic stem cells, mesenchymal stem cells, and the like), and germ cells (e.g., primordial germ cells, embryonic germ cells, and the like).

Transgenic animals or plants can be produced employing the methods that are routinely practiced by the skilled artisans in the art. See, e.g., Brinster, et al., *Proc. Nat. Acad. Sci. USA* 82: 4438, 1985; Houdebine and Chourrout, *Experientia* 47:897-905, 1991*; Teratocarcinomas and Embryonic Stem Cells, A Practical Approach*, E. J. Robertson, ed., IRL Press (1987); Hogan et al., *Manipulating the Mouse Embryo* (Cold Spring Harbor Press 1986); Krimpenfort et al., *Bio/Technology* 9:86, 1991; Palmiter et al., *Cell* 41:343, 1985; Kraemer et al., Genetic Manipulation of the Early Mammalian Embryo (Cold Spring Harbor Laboratory Press 1985); Hammer et al., *Nature,* 315:680, 1985; Purcel et al., *Science,* 244:1281, 1986; Pursel, et al., *Science* 244:1281-1288, 1989; Simms, et al., *Bio/Technology* 6:179-183, 1988; and U.S. Pat. No. 5,175, 384, and U.S. Pat. Nos. 4,945,050, 5,175,384 and 5,175,385.

EXAMPLES

The following examples are provided to further illustrate, but not to limit in scope, what is described herein. Other variants will be readily apparent to one of ordinary skill in the art and are encompassed by the appended claims.

Example 1

Identification of Native Chromosomal Sites with Strong Transcription Activities Plasmid for random integration into CHO genome: The plasmid was modified based on the original attP containing plasmid described in Thyagarajan et al., (2001, Mol Cell Biol. 21(12):3926-34). Specifically, the original plasmid was modified to replace the ZEOCIN™ marker with a Neomycin marker. In addition, the firefly luciferase gene was replaced with the EGFP gene controlled by the SV40 promoter (FIG. 1).

Stable transfection: The modified plasmid was purified using a Qiagen midiprep column. Twenty-five µg of DNA was digested overnight with restriction enzyme BamHI to linearize the plasmid. The resulting linear DNA was then transfected into CHO cells to create stable integrations. Two days after transfection, cells were split into new plates and hygromycin was added to growth media for selection of stable integration events. Cells were grown in culture for three weeks before harvesting for FACS analysis.

FACS: After three weeks of growth in culture under hygromycin selection, stable cells were pooled together for bulk sorting at the Scripps FACS Core Facility; the top 1% of EGFP-expressing cells were collected, returned to culture media and allowed to recover and grow for several couple weeks. When the cell culture plates were confluent, cells were collected and sorted by FACS again. This time, the top 1% of EGFP-expressing cells were sorted as individual cells into the wells of 96-well plates.

Single cell populations: Cells sorted into 96-well plates were allowed to grow in these plates for two to three weeks before transferred to 24-well plates. After one week, cells were transferred to 6-well plates for expansion cultures. At this stage, EGFP expression was checked to ensure that the single cell populations contained a stably integrated the attP-containing plasmid constructs and maintained EGFP expression.

Growth rate check: After confirming the EGFP expression, the single cell populations were checked for growth rate along with the parental CHO cell line. Cells were seeded into 6-well plates at 10,000 cells per well. Cell numbers were counted at three time points: 24 hour; 48 hour and 72 hour after plating. Only cells that had growth rates equivalent to or faster than the parental CHO cell line were further cultured for stability studies.

Stability studies: Single cell populations were further cultured for up to four months to determine the expression stability. Cells were checked for EGFP expression once every month. At the end of the culture period, both of growth rate and EGFP expression were checked to make sure that the single cell populations had maintained a high level of EGFP expression and grew as fast as or even faster than the parental CHO cells. After this stage, twenty single cell populations were chosen as good candidates for identification of chromosome integration sites.

Identification of integration sites: Genomic DNA was purified from the top 20 single cell populations. Individual DNA samples were checked for concentration and 10 µg of total DNA was used for enzyme digestion using four blunt end generating restriction enzymes: EcoRV, PvuI, StuI and Hindi. The completely digested DNA samples were then subjected to purification with phenol and chloroform. These DNA samples were then precipitated using ethanol and ligated to a double stranded DNA linker molecule (GenomeWalker Adaptors).

Three gene specific primers (GSPs) were designed based on the hygromycin resistance gene. GSP1 and AP1 (Adaptor Primer 1) were used in primary PCR reactions; the GSP2 (nested gene specific primer) and AP2 (Adaptor Primer 2) were used in secondary PCR reactions. If needed, GSP3 and AP2 were used in tertiary PCR reactions to obtain specific products.

The results indicate that native chromosomal integration sites in the CHO genome that support stable integration and strong transcription activities are present in the ankyrin 2 gene (Ank2), cleavage and polyadenylation specific factor 4 gene (Cpsf4), C-Mos gene, and Nephrocystin-1/Mal gene. The exact positions of the genes for integration of the heterologous sequence are respectively indicated in FIGS. 3-6 (SEQ ID NOs:1-4).

Example 2

Inserting Landing Pads at Identified Native Chromosomal Integration Sites

Homologous recombination: Genomic DNA flanking the integration sites was identified and cloned into a plasmid that contains both positive and negative selection markers (FIG. 2). For each site, the longer homology arm (3 to 4 kb in length) is cloned 5' of the neomycin resistance gene. The short homology arm (1.5 to 2 kb in length) is cloned 3' of the neomycin resistance gene. One single phage attachment site attP is located at the end of the long homology arm.

The homologous recombination plasmid is digested with NotI enzyme to linearize the plasmid; the long homology arm is at the one end of this linear DNA. Upon transfection into CHO cells, neomycin is added to culture media to select for cells that have this linear DNA integrated into the cell chromosome. A pool of resistance clones are obtained after 4 to 6 weeks. Then cells are subjected to negative selection with the addition of ganciclovir to the culture media, which will kill cells that have randomly integrated the plasmid. Only cells that have undergone homologous recombination at target site will survive both positive and negative selection. After both rounds of selection, cells that survive are picked and grown in 24-well culture plates and then expanded to 6-well plates. Genomic DNA is then isolated from these cell clones and checked for attP site integration into the targeted locations.

Landing pad integration: After verifying that the attP sites are inserted into the desired locations, these cell lines can be used for integration of recombinant genes into the attP sites using the phage Phi-C31 integrase system. Recombinant genes are cloned into a plasmid containing a single attB site. Upon cotransfection of plasmids containing the recombinant gene and the Phi-C31 integrase gene, cells can be selected for specific integration events.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

What is claimed is:

1. An ex vivo or in vitro method for stable integration and expression of a heterologous polynucleotide in a Chinese Hamster Ovary (CHO) host cell, comprising inserting the heterologous polynucleotide into the genome of the host cell at a native chromosomal site located at or close to positions 130-131 of SEQ ID NO: 1 of ankyrin 2 gene (Ank2).

2. The method of claim 1, wherein insertion of the heterologous polynucleotide is mediated by homologous recombination or by a hybrid recombinase.

3. The method of claim 1, wherein the heterologous polynucleotide encodes a polypeptide.

4. The method of claim 3, wherein the polypeptide is a therapeutic protein or an industrial protein.

5. An ex vivo or in vitro method for stably integrating a heterologous polynucleotide into the genome of a CHO cell, comprising:

(a) inserting a first site-specific recombination sequence into the genome of the cell by homologous recombination, wherein the insertion is at a native chromosomal insertion site located at or close to positions 130-131 of SEQ ID NO: 1 of ankyrin 2 gene (Ank2); and (b) integrating the heterologous polynucleotide comprising a second site-specific recombination sequence into the genome of the cell at the inserted first site-specific recombination sequence.

6. The method of claim 5, wherein the native chromosomal insertion site supports stable integration of a foreign gene.

7. The method of claim 5, wherein the first site-specific recombination sequence is a first recognition sequence recognized by a phage integrase.

8. The method of claim 7, wherein the phage integrase is phiC-31 integrase.

9. The method of claim 7, wherein the first recognition sequence is an attP site or an attB site.

10. The method of claim 7, wherein the heterologous polynucleotide is attached to a second recognition sequence of the phage integrase which is cognate to the first recognition sequence.

11. The method of claim 10, wherein the second recognition sequence is an attB site or an attP site.

12. The method of claim 5, wherein the heterologous polynucleotide comprises a target polypeptide-encoding sequence that is operably linked to a promoter sequence.

13. The method of claim 7, wherein the integration occurs in the presence of the phage integrase.

14. The method of claim 13, wherein the phage integrase is expressed from a vector introduced into the cell.

* * * * *

```
SEQUENCE LISTING


<160> NUMBER OF SEQ ID NOS: 13

<210> SEQ ID NO 1
<211> LENGTH: 254
<212> TYPE: DNA
<213> ORGANISM: Cricetulus griseus
<220> FEATURE:
<223> OTHER INFORMATION: Ankyrin 2

<400> SEQUENCE: 1

aaaatttctt gctttcttct aaaagcatta tctataaata tttgttgtct aaaactcatt     60

tttcccatgt ttagtgtgtg tgtttatgcg tgagtgcata ttgtcttggc taccatgaag    120

agaaatatta tttttccttc cagtgttctt gagtggcaaa ttacttttct gttgcagtgt    180

gacaacacca ggggcagaag gggcagagac tcaaaaagcc acagaagttc ctgactctct    240

ctgtaagact cctg                                                      254


<210> SEQ ID NO 2
<211> LENGTH: 1148
<212> TYPE: DNA
<213> ORGANISM: Cricetulus griseus
<220> FEATURE:
<223> OTHER INFORMATION: cleavage and polyadenylation specific factor 4
      (Cpsf4)

<400> SEQUENCE: 2

ataaaatcaa aataatgcat cttttgaaga aagcataaaa accaatatac agaattgtga     60

tatgacccgg catccctttt gggacggcag tgactgcagg cgagaaggag gggatggcag    120

agagcagtgt gaagtgggga gggcagctaa gagacctgag ggggagccag gtcctaggcc    180

tctgccgccg ctgccatgca taaaatcatc gccagcgtgg accctatcaa gttcgacttg    240

gagatcgcca tggagcaaca gctccaggcc cttcccagga taagtcgggg gctgctgtct    300

gagaattcat tttgaaagct gcctgtggca aatgtggcat gtgtccattc cgccacatta    360

gtggtgagaa gacagttgtg tgcaaacact ggctaagagc actctgcaag aaaggggacc    420

agtgtgagtt cttacatgag tacgacatga ccaagatgcc cgagtactac ttttacccca    480

agttcgggaa atgcaacaac aaggagtgcc ccttcctgta catcgaccct gagtctaaga    540

ttaaggactg cccttggtat gaccacggct tctgtaagca tggcccccctg tgcaggcatc    600

ggcacactcg gagagtcatt tgtgtgaatt acctggtagg attctgccct gaggaaccct    660

agggtagatt catgcaccct ccatttgaac tgcccatggg aaccactgag caacctccac    720

taccacaaca gatacagcct ccaacaaaga tcattgggtt catgcagagt caaaatagca    780

gtgcagggaa cctgggaccc tggacattgg agcaagtcac ttactataag tgtggtaaaa    840

aaggacacta tgccaacaga tgcaccaaag ggccaattgg catttctcag tggacagtga    900

caatagctgg gctctgtgga gcagcctaag agacctgctg ttggtaacaa gcacttagct    960

gctcaatgta gtgctggcag gactggctag agcctcaggc acacttgcca gggctcattt   1020
```

```
tgaggggcca tgtctgtcct atcattttgc tgtaatcttt tttctttaaa gaaggaacat   1080

gtgcttcagt tgggtccctt gagccagctt gcttggacat cagtgcctca ttttttggac   1140

tatgtgct                                                              1148


<210> SEQ ID NO 3
<211> LENGTH: 743
<212> TYPE: DNA
<213> ORGANISM: Cricetulus griseus
<220> FEATURE:
<223> OTHER INFORMATION: C-Mos

<400> SEQUENCE: 3

cagacatttg ttgaactact tgccagggtt attagatgca acctttgtaa gaattaacat     60

ctgtaacttt aatgtctttg atccaaatac aatcacttat agaagtcaga tcacatacct    120

tttacgttca tcagaaggga gcattctgac actgtatttg atttaaacag caagttaaga    180

ctctgtaaca taacaacaca gtgacctccc aatatccctt tccaaggcaa gttaagccac    240

cccatgagtg tgagtttgct tcaagacaga ttctagactt cacagaaagc aagttcctgg    300

aatttaatgc agagttggag gaaggaagaa aggaacaaag gtgattgtga tgaccacggc    360

tgtaaatatc agcaagcgtg ggaaaacaga ggaaaagtca ggagaaatag acatggctca    420

gaatcactgg tacccatcta taatatggaa aagcagatgc tgaacacaaa ttcagggtct    480

ggccatcaaa ccacacattc ctcctttttt gttttataaa aatgcgctca gttttatgct    540

atatctctgg gagaatgggg aagagccttg ctctgtttat tcaaaaacgt ttctcaaagt    600

ggctaggagt tactcctctt agctgcttgg taaggtgttt tatgcataca ggtgataagt    660

gatcactttt catgtgacag ctgtgtccct ttgacttcag aatcacaggt tttgagaaga    720

caataaagga gagacatata aac                                             743


<210> SEQ ID NO 4
<211> LENGTH: 618
<212> TYPE: DNA
<213> ORGANISM: Cricetulus griseus
<220> FEATURE:
<223> OTHER INFORMATION: Nephrocystin-1/Mal

<400> SEQUENCE: 4

cctccagaaa gccttgcggg tcaactaaga attcggtcta acgactcacc aaccctcaac     60

actcctcatc cctcaggccc ttgtctaaac tagccagacc cacccagccc agcgcccctc    120

tcctttgaaa ttcatcactt tctcaaagtg taacaggtgt caacgtatag tcttaataaa    180

ctaaccaagg acagattagt aatttcagaa aagttaattt caaagatgat caaacacaaa    240

agatcgtagc gattttaagt cataaccctc agtgctgagg aagactcgat gaaacaggcg    300

atgccctggt atatagtcta catttctgga cagcagtttg acaacatata gcgagcattg    360

atcctcctag gctggttgat tacattctca gcaatctccc acttacaata acttaaaagt    420

gtgacagaga tggatattta aatgtgttca ccacattttt tgcttataat agaaaagctg    480

aatatgaata aatgataggt attagtggga tggataaact aatccataga tggattaatg    540

ttatacaggg cttctcagtt cttcttttga gggaaaggat ttagtggcag gacacaaagc    600

ttaaacagaa gtttatat                                                   618


<210> SEQ ID NO 5
<211> LENGTH: 39
<212> TYPE: DNA
```

<213> ORGANISM: Bacteriophage phi-C31
<220> FEATURE:
<223> OTHER INFORMATION: phi-C31 phage integrase attP site strand 1

<400> SEQUENCE: 5
ccccaactgg ggtaaccttt gagttctctc agttgggggg 39

<210> SEQ ID NO 6
<211> LENGTH: 39
<212> TYPE: DNA
<213> ORGANISM: Bacteriophage phi-C31
<220> FEATURE:
<223> OTHER INFORMATION: phi-C31 phage integrase attP site strand 2

<400> SEQUENCE: 6
ggggttgacc ccattggaaa ctcaagagag tcaacccccc 39

<210> SEQ ID NO 7
<211> LENGTH: 34
<212> TYPE: DNA
<213> ORGANISM: Bacteriophage phi-C31
<220> FEATURE:
<223> OTHER INFORMATION: phi-C31 phage integrase attB site strand 1

<400> SEQUENCE: 7
gtgccagggc gtgcccttgg gctccccggg cgcg 34

<210> SEQ ID NO 8
<211> LENGTH: 34
<212> TYPE: DNA
<213> ORGANISM: Bacteriophage phi-C31
<220> FEATURE:
<223> OTHER INFORMATION: phi-C31 phage integrase attB site strand 2

<400> SEQUENCE: 8
cacggtcccg cacgggaacc cgaggggccc gcgc 34

<210> SEQ ID NO 9
<211> LENGTH: 152760
<212> TYPE: DNA
<213> ORGANISM: Cricetulus griseus
<220> FEATURE:
<221> NAME/KEY: misc_feature
<222> LOCATION: (50692)..(51086)
<223> OTHER INFORMATION: n is a, c, g, or t
<220> FEATURE:
<221> NAME/KEY: misc_feature
<222> LOCATION: (84882)..(84898)
<223> OTHER INFORMATION: n is a, c, g, or t
<220> FEATURE:
<221> NAME/KEY: misc_feature
<222> LOCATION: (114932)..(116327)
<223> OTHER INFORMATION: n is a, c, g, or t
<220> FEATURE:
<223> OTHER INFORMATION: Ankyrin 2 gene
<308> DATABASE ACCESSION NUMBER: GenBank NCBI No. NW_003615916.1
<309> DATABASE ENTRY DATE: 2011-10-27

<400> SEQUENCE: 9
ataattaacc aggaggagag acactatttc tcttgctgtt taatgttctc caccaaacac 60
caggcaaata cagcagtgaa gcaaagcagg aagcacagca caataagcaa atgacaggga 120
cacagttact gctacttgga aaaagagaga gaaaagcaaa cttcactatt ctgttttctt 180
tgggaaagcc tgttatgtta attccagaag atcttgttaa tgaaccagaa acaacacaga 240
tctagagatc tagttggccc tttaatggtg tagtaaggtt caaacctgct cagttttaag 300
catttgtttt cactgtacac acacacacac acacacacac acacacacac agagagagag 360

```
agagagagag agagcgagag agagagagag atgaagcagt ttttttctta tgtttttgaa    420
accgcagcac tccaaaggat ttcagtttgg catattcttg tcttgtcttc acatgaatat    480
attcaattaa tttcctgttc tctggttgaa acaaaaagaa aagaaaagaat gaaaacccgg   540
agctaactgc tcttcccaaa gtctctctct catgctgcta ccacttaaca aaaatgaacc    600
aaatcctttt ggccttgccg tcggtgttgt tgactagatt actcagttct cctgttcccc    660
aagtcctcag aagctcctac ttttcattta ctagatatct gcaaattaaa catatatcct    720
tgtttccccc aggtgaggga tggtaagaat tttccttgga gctctgaggc actaatccag    780
agcatgccac cgtccggggg gacagtagat tccttactaa ataaaagcac taaggagata    840
ggccattgat gagtttctgt tggcttcata tctacttcat tgaacagctt ctgactctcc    900
aaaactcata gactgatgac aaagaaggac aaagcactgc tgccacattt aacacttgta    960
cattttattt agttaaatca gccattgtac aacattgcag ctatgtattg ttagtgttgt   1020
attgttttcc attaactaat acatgccctc atagatatat tcaattagtg ttatcaccat   1080
gggaacaaga tgctgattca tcaactgaaa attctgaaaa ttcacttctt ctcacagtat   1140
tcaagttttt tttgataaca cagcaaaaaa aaaaaaatca aaattgaaag aaggtgaatg   1200
accattatat tgctacacag acatcatctg cactgcaaat aacacaacag aaaggctttt   1260
catgagctcc ggtgaagttc tgacaagatg gccatggcat atctcaaaaa gggctgccac   1320
atgcctctct tgttctggat gccaaagaat actttgtttc tactcaaccc cccacagaaa   1380
gtgctagcgt taggggctca ggagatttgg gagatgggaa acctctctcc caagaaaatt   1440
cctctcttgg taatgttact ttaaaagatg aagtgccatt gtttgtcctg tttgtgtttg   1500
acattccaag caatgagtca gttctgcaca caggaaaagg ccagatagga ttggacaaag   1560
ttcagtctca ggagagtaca ctgttttctt tctttctttc ttttttttta aatctcatct   1620
tcattgaata tacttttctt taacaaataa ctgattcaaa acgtatactg tttatatgaa   1680
tatatttgtg actatatata tatatgttaa aatgctacac agcttcaacc actagaggga   1740
ttagacacag ggcatgggga tcactcagtc atcgtccctt ctctgaaaca aacagaaagt   1800
tgcacaaatg cacttcagtt tccaagggtg tctgggtttc aaataaataa atcaaaaaaa   1860
ttaatcaaaa ccaaattttc caaggatttc tcaatctcgt ctgcaagccg aaaagcagac   1920
atagctagaa aatgaaagcc catggttaaa accattagta tgacaaaaag ggtttgtgtg   1980
tgtgcgtgtg tgtgtgtgtg gtgtgtgtgt gtgtgtgtgt gtgtgtgtgt gtgtgtgtgt   2040
gtgtgtaatg ccacatgcag gtattagaga agagatacac ctggaggtgg gggtaaaaaa   2100
aaaagcaaaa gaaaccactc caacatggtg acatcattta acattttgtg tggtgcataa   2160
atcttgtttc caatgaatta tctacagtgc agtggccaga agaaagtacc accagtaaga   2220
cagcgtggtt tgctaaagca gcgatgaaca ctggaaaact acagtagtta tagctttttt   2280
aaaataccct gccaacgtgt ccaaaatcaa aaacacctga aagtgctaga acaccaccca   2340
tgcagcttct agcaccagaa tacctcattg tttccatccg cttgtctgtg ctcccttctt   2400
cccctccctc agggtggcag ctggagagcc atcatcgatg gctgaccagt actagattct   2460
gctccttggg atcattcttc aagattatga tcctgtattt aggagcaatg gctactctgg   2520
aagtactaag gacatgtcaa ggtctgaagt gttcctttca tagaactgtg ttacccttaa   2580
ctgtgttaac aatatcttaa ttaaccattg ttcagcaatt tcaagaggct tttattccat   2640
gatgcccagt gaaattatga caggcagtgg tttaaatttt actctgttgt tcgtctgaga   2700
```

```
atgtcagcta tatacattat acatggatat cctcggaaac attcccctct gtcacttgaa   2760
gaagtctgca ggtgaagttc ttctgatttt catggagcct gagcagaagc aaagaacaat   2820
ggaggcgcca gttcccaggt tagcacagat gctcagaata gtggatacag catccagaat   2880
gaaggatgct atctttggtc acaaattagc ttatagttag agagggtggg ggagaaggaa   2940
gcaaaagaaa atgccttgta tttgccaaga gtggaaatgt cacaggatcc cagtaattag   3000
gccacttggg tcactcctga caggaaatgg gaagttgcat attgagtggg tatgtggttt   3060
ctggtaagaa ctgggcagct cctcattggg cctcttgctt tgtgttctcc ttgcagaaat   3120
gccgaaggag ttggtggaga tctctctgga ggtcgtcttg gtctagtgct ccaggaacat   3180
cctccaggtg ctccaagttg atgcgttttc cctgctggtc cttcaccaca gccctcttct   3240
gtgtactggc tttactcatt gttgtcctac agggagcaga tcagataatg agaccctttc   3300
cctgacaccc atggacttcc tgtcatacca tgtatttatt cctattagtt taatgatgac   3360
aggtggacag ttatgtttct cacatctctc ataaatgagg ctctcccaaa gcttaaaaag   3420
tgtattttag aacaagaaac attgattttt tatatcttta aaaatagttc aaataaagaa   3480
cactatgcct ccattacatt ttcacaaaga gaagccaggc catggctcag attttggtta   3540
agttgcattg atccaaaagg ttctcgctta ctctgaaata atgataccaa aagcatcatt   3600
gacaaaatca gaaaatcata taaaattcac tcacttccca ttctgaacct tgcccaaatt   3660
ttgttttact atgagatttg atttccatga gattgaaatc tttaaaaact ggagtattct   3720
accaaaatat gagaagggga ctctgaagct cccttgagag taagcaaggg agggaaagga   3780
gatggagatg actcccaagg gcaaacactt tctgtgtatc cttgggacct ccacgtgctt   3840
aaccagttct gcatgttcca ccatgtcagt cagcaggcat cttccttccc ctggtgctcc   3900
ttgagaaaag atgccctagc ttgctatttt atttcaaact attattttct tagagtctcc   3960
acttgaaaat gatattgtaa tgtgttcttt ttctattctt ctcaccatct atttatgaga   4020
ataatgcttc attctgcaaa taggtgttga atgtatttta tgtactgtct atagttataa   4080
caaataagaa aactgacctt agaaggttta aattacatcc ccacactttt tcttttttaa   4140
acattagcta agggtccaag attcctgagt ctgggtccat aagcaggaat ccatggatct   4200
tcaaatccaa caacaaagaa tgaccaggta ttttccttat gactttgcag tgttttgaaa   4260
ctagaagttt taacaatggt cattctaacc tgatgctagt ttctaaaaat ttacttctgc   4320
ccaattccag ctctcctttg gccatccttg cttccgacct ccttctccaa gtctctctta   4380
gatattacat acattgcatt ttcatttgat gccatatcta aatttgttcc tcttgatgaa   4440
atgttcatag ttgatcactg tggctgcagt cagtttgtgt gtttctggct gttccctatc   4500
atttctggtt tgtttacttc acaaaagaca aatatctgtc tctttctgcc agggattagg   4560
agaaggttcc acagttctgg tgtcaggggg caggcctaca gcgtgggact tttttttttt   4620
ttaattttct gcagatgtgt gcagatgttt atacatacac atgtatatga taaaatgact   4680
tcagtaatgt agaaactcaa gtgctgttca ccagagtccc acactgacta gcagtgtgca   4740
tgcaagttgt ttgttactgt cttcagctaa gtgtccacca cttcaaggac acagggaggc   4800
aactgctctc cgaatctatt ccagttcaaa gatcatggga tgccaaggtt tgcaaaggct   4860
atatagtttc aaccaaacaa tcagacaaaa gggttcaaca ttcaaagcag aagcatttta   4920
tccgtaattt atacggcatt taaaagctct aggcaaccaa ttatgttctt ctaaattcat   4980
agctgctact gtttctcaca tttgagctga aggcgggact gtgacagaac cttaattttg   5040
cttgtaatta ttatgttcca gaaacctaaa atagccttgt ggagtactat aaatgacaat   5100
```

```
ctttctccct ttttcaatga gattggaagc acagcaataa cttgggctcc cattgtatct   5160
ttcactgaga agctaagagg tttgtgagag tagtgatgct tacaatggcg ctagaggacc   5220
aaagtggtga agagaggctc cagaagcaat gctcagttct gacatcagaa ttgcaatgga   5280
gcctcacagc gagcacacga gggaaaggct gcttaccatt cacacatgct cttactcatg   5340
ctgcttgcgg caacattctg tacatccagg acctcagaca tcaaacatgt gctcttgttt   5400
cttgtcactc ccatgcatca ccatggaagt tgttaacagt aaaaagccat gatagaggaa   5460
gactgagctt gatatagtta gttgccaagt taatcagtgt gcaatcgatt agatttctct   5520
tcatatggtc tccaaatcta tcaacacagt ggtattcccc accggcttag ctccaactgt   5580
attgacaatt tgcttgaacc cagaaagcca aattgtataa acaaatgtct caccatcact   5640
gtgtctcagt attaatttga aagcatcagt ggacatgcta ggggcaacac acacacacac   5700
ccatgcctga cccaggcctt ctcacacagg gcagtcagag gctcagaagg gctctaccct   5760
tcctttctag cattagaaac tttgtatcat gttagtggtc aaaacatcac cccatgctaa   5820
cccaaacctc ttaattattg atccatcctc cttcaggatt tcattttcta ctaaactggg   5880
gaagtgaact ttcatgtggc tacctgtgta acccaaagcc tgagataaga aaaagagaaa   5940
acaagacttg actcatagat caccgacttt cattgaagca gtctactgtt ttactagtta   6000
gtcttctgct ttactaatta gtctaatgct ttactaatta gtctattgct tcactagtta   6060
gtttagtgtc ttactaatta gtctactcct ttactagtta gtctactgct ttactaactc   6120
tggtggtaca aaagaggtat tcgatggggt aacatatgag ctcatatgtg ggtatcgagt   6180
tttatttaac acgtccttta aaattccatt tatgtcacag ataatactct ttgttaaaag   6240
cttgaaactg acatctagac tgactgactt taaattttcc ccttatttgc catcctcctt   6300
ctgattgtgg agatttgaat aatatatatg agctcatatg tgggtatcga gttttattta   6360
acacgtcctt aaaattccat ttatgtcaca gataatactc tgttaaaagc ttgaaactga   6420
catctagact gactgacttt aacttttccc cttatttgcc atcctccttc tgattgtgga   6480
gatttgaata ataaatgaga tcatttatca aagacaaaac cagatacagg gtccaatgta   6540
caacttagac aattcacttt ttgaacaccc aagaggtcaa atgtgcagaa ttaaaagtat   6600
ttaaagaaag tttgctttaa atacaaaaat atgttaatag actacttata tataattgtt   6660
gatactatta ttgttgttgt gatattgttg ttctagtatc tggtgatcaa acccagtgct   6720
ttgtgggggg ccacataggc atcctaaaat acagctggat ccccaggcct aatgtgagta   6780
agtacataag ggcactgatt atagcattta actttaagca tttaagatat aacttatcta   6840
ttttttttagg caggctgcca taaagaagtc caggctagcc tgagctcact ctgtagcata   6900
agctagcttt gatcttgtgg catcatgctt tagccaccgc agtgccagta ttacaaacct   6960
aggccaccac acttggcttt gtaattttaa cagacatagg aaatcatgcc ccaactctgg   7020
aaacttggat tctgccctgg caggaatgaa tctcagcaac ctgcattttt aagagccctc   7080
tgggtgacat gaatgaaaac cagggggctg cagaaataca acttcaccac ataaattgtt   7140
taagacggaa atctggtctt ttcagttata caaacacctt ccatgaatct gtgtatgaaa   7200
tgacaaatgc ttttctttgc taacacaaag caaccataaa acgcacatca aaggaaaaca   7260
gacacaaaat aaaacaatgc tctgtacctc ttcaaagtca tctttggctg aaggaaggtc   7320
agtggctaag ctagagtccc ccaggctttt ctccatcctt tctccatgta ccactgttgt   7380
tttaacaact ttgctgactc tacggccttc tactggttca gcctgaaact gtgaggtact   7440
```

```
ggacaaaatg ctgggttcag acaaggtcac ctaatgaatg aaggacacat aacagacaat   7500
tcccaatggc caaaatggaa caaataatga tatttctgtg aaataaaatg gttgtaatac   7560
tggcttccta aaaaaaaaaa aaaacagtaa ttaggaacaa atctcatcaa ttggtctatt   7620
tgagggtata ctgccagaac acgaacagtt aatgggctat ttgaataaaa tctcaccagt   7680
cacatttcct aagggctgac aggcacaatg tagattggca acctaggctt gatctctttc   7740
ccacaattaa gtttatttcc tttgcaacat gaagataaag tcaacccctg aagggagagc   7800
ttgaaaagct atgagaaatc aaagtggata actagacagc ttcgtgtcta taatcatatg   7860
attctgaaga tataaataaa cacagaacag taagaatttc aaattgtgtg tgtggtggtc   7920
tcaagtcttc aaacagtgag gtaaaataga aagtaataaa tggcctaaat caaagcattt   7980
cagatcataa tttaattaac cctgaaactc agaagtttga ttgtcaagca tatatcgaaa   8040
gtgactcttg gaaggctggt gtgccaacaa ggcccaatca ctgcagtaca tttgggtacc   8100
gtactcttca tagcacatac cttgccagaa aatagattta aaatttggct tttgattgct   8160
actgtaatca actaagaatg aaatgcaaca tagaaatgaa gaaaaacaaa gacaatgagt   8220
acaaggacca catagaatgg aaatacagtg ggaactgaca tgtttttttcc tgttttgtct   8280
ttctctgcac aatgaactct gcagagctgg gtggcctcac ctctgattgc tgggtgtcac   8340
tcttcaatac cacacgcttt atcactttgg aataactgtc cccatcctca atgttgactg   8400
gctcctgtgg cgttccctgc attgtaatct cctccttctc catgccatca gaggatacgt   8460
accgcctaat gattttccgg gtgacctgaa acacatttca tgttgctgcc ttattttttg   8520
tgtttcggca cccacactag tgacagcatt taaacaggaa gcgtgaaaac agccctgtac   8580
agagagccac tggcaggtac cttcttcacc acggtgtgtc cattctcatc gacatattcc   8640
tcttctgaga cagtttctgg gggtatgtca ggcatatcat ctccctaaac agtgggggaa   8700
aagcattacc taagtgtgtg gcactgtcct gaggaactac gtccaagtgc ttctgatatg   8760
aggaatgtta gaaaaccaga ggtcatgttg ccaagtattg ccgagatgca aaatcctgtc   8820
agtttgatta attttaaaaa atgaagcagg tatattagca agaaaaaaca aaacatgctt   8880
aggagaatct caccaaagtt agggaaaatt taatcaaaca acaaaaacaa ataagcaaga   8940
agggaggcag gtgcaaccct agaagccaag ccttctgcgt gctggctcat ggaggagggc   9000
tgcaaacatc cttggctctc tgcatcccct aacaaatgag agaggaagag gggagctgct   9060
ttccatgcat gcactaccta tggatcatgc tcagcctctg ttgttccaga tctctcttag   9120
tgaaggacac aactgtcccg acgtgcagta acttaacagc gggtacctgg ataatcactc   9180
tccggcggac aaccctggta gttaccatgg cctcctcatc agagctggcc tccagctctc   9240
ctaattcctc tgttagctcc tggtggaagc atgcatgaat cgttgttttt aatcttattt   9300
taaattttaa aatgtaatca aaaattgtat ttggtttcca agacagggtt tctctgtgta   9360
tcagccctgg cattatcctg gagctcactt tataggccaa gctggcgtca aactcccaga   9420
gatctgcctg cctctgcctg gcaagtgctg ggttaaaga cgtgtgccac cacctccgag   9480
cttcaagaaa aacttgtttg agatgggata ttacttggtg gaccaccctg gcttgaactt   9540
ataatcattc tgtgccagac tcacgagtgc caggtttaca gatgtgtgtc accacacttg   9600
gctgcatcat tttgtttaat ttgctattga ataactgtac tattggtttc tttatttgtc   9660
tgtatcatat tctgaaattt tatgcaggga gatattgata gaaaatcatc agggaaaaag   9720
taaatgtgtg gttatctcaa gcctcaacaa gcatggagtc ttattgttcc caaaatcata   9780
aagaaatccc gcaatctgag agtggttgga aaagccactg tcaaaactgg tcccaagaga   9840
```

-continued

```
tgtcttttcc cacatgaatt ctgtacttaa gtttaataaa atctgggtga aagtacagga   9900
cctaagtagc acactaaata cctgtgacac atgggccagt cttgactagg caaggaattc   9960
taatcccaca cacagaacag ctcatatttg tagcagagct ttctccagta agttaaattt  10020
cctgtagcta ttagtaaata gtacattttc ctgccatcaa aaattgtagg ctttaaataa  10080
cattgaactc ttttttttta gagaagctaa gagaatactt tcatttatgg gtttgaccaa  10140
aagccaaaga tgaggctagg aacataattt tagattgaaa atgccttaag agtcataaac  10200
agagacaggc tttcttcaca gaacatgatt tccttcctcc tctctcctcc cctcctctta  10260
cttcccctcc tgtctccccc tcccttcttc ccttccaggt tttttgacaa aaatcaagct  10320
atgttgtatc tcacaggttt taaacttttg atccttctgc atcagccttc agagtacttg  10380
gatgaccggt ataaataagc aagaagggag gcaggtgcaa ccctagaagc caagccttct  10440
gcgtgctggc tcacggagga gggctgcaaa catccttggc tctctgcatc ccctaacaaa  10500
tgagagagga agaggggagc tgctttccat gcatgcacta cctatggatc atgctcagcc  10560
tctgttgttc cagatctctc ttagtgaagg acacaactgt cccgacgtgc agtaacttaa  10620
cagcgggtac ctggataatc actctccggc ggacaacccg actttttttt aagggaaaga  10680
gtacactcaa aaaacttact gtctcaaaac acccaaagac aatcaggaac ctactgctag  10740
caatatggtc agcaacaaaa ataactacaa tgacatgttg gggttactgt tgtaagaagt  10800
taggagttca caagtgaagc atatgaggga cgactagaaa tgcattgagc taagaagagg  10860
ccgtaaaaac cctaggatgc taggccaagc tggcgtcaaa ctcccagaga tctgcctgcc  10920
tctgcctggc aagtgctggg gttaaagacg tgtgccacca cctccgagct tcaagaaaaa  10980
cttgtttgag atgggatatt acttggtgga ccaccctggc ttgaacttat aatcattctg  11040
tgccagactc acgagtgcca ggtttacaga tgtgtgtcac cacacttggc tgcatcattt  11100
tgtttaattt gctattgaat aactgtacta ttggtttctt tatttgtctg tatcatattc  11160
tgaaatttta tgcagggaga tattgataga aaatcatcag ggaaaaagta aatgtgtggt  11220
tatctcaagc ctcaacaagc atggagtctt attgttccca aaatcataaa gaaatcccgc  11280
aatctgagag tggttggaaa agccactgtc aaaactggtc ccaagagatg tcttttccca  11340
catgaattct gtacttaagt ttaataaaat ctgggtgaaa gtacaggacc taagtagcac  11400
actaaatacc tgtgacacat gggccagtct tgactaggca aggaattcta atcccacaca  11460
cagaacagct catatttgta gcagagcttt ctccagtaag ttaaatttcc tgtagctatt  11520
agtaaatagt acattttcct gccatcaaaa attgtaggct ttaaataaca ttgaactctt  11580
tttttttaga gaagctaaga gaatactttc atttatgggt ttgaccaaaa gccaaagatg  11640
aggctaggaa cataatttta gattgaaaat gccttaagag tcataaacag agacaggctt  11700
tcttcacaga acatgatttc cttcctcctc tcccctctcc tcccctcctc ttacttcccc  11760
tcctgtctcc ccctcccttc ttcccttcca ggtttttttga caaaaatcaa gctatgttgt  11820
atgtcctccc ttgggcccta tgggcatcta aaggaggaaa gtgcctaaga ggaagaaatc  11880
atttcatgtc tctttcttct catgttccag tgacaagaga gcaaaactca gtgtcaacag  11940
agtactgtgc tgtgagctct tgacacacta aggttgcttc tcctgagcca ctttcctttt  12000
caggatggcc agtgtcactc aggcaacttt ctcctttacc tgctaaagtt ctgagctaaa  12060
tgattttcta gggtttcttt ccagcagaca atgcctcctt atccttactc taactctgct  12120
ttatctcaaa ctaatggtgt tgtgtcctgt ttgcatgatt tataccatat tgatgttttg  12180
```

```
tttgtttttt tgtgtgtttg ttttgttttt tcaagacagg gtttctctgt atagctttgg  12240
agactatcct ggcactggct ctggagacca ggctggcctc gaactcacag agatccgcct  12300
gcctctgcct ccctatgcct cccgagtgct gggattaaag gcgtgtgcca ccaaccccag  12360
gtcatactga tgtttttata cttagatgct acatagcttt gctgaagtac taatgggctg  12420
ccattcctac accatcactg ctcaaacccc aaggcagcca tggcactaag tgggcacatt  12480
ccaatgagat acaacaatcc tacaagtagt gactgtggtt tgcaaggagt acacccaaag  12540
gtgattcaca ggcttatcag tggcccttga ccctggtaac tgataactag atttggaaat  12600
ggagacttgg agaactttgg gattgttcaa ggttacagaa ttggaagtcg gctcaggtag  12660
gacagtacca cacaacatga tcacaattat gtatcttgac tgtttcagct cttctacagc  12720
ctctgcccct tctgcccctg gtgttgttat actggaacag aaaagtcaat ttgccactca  12780
agaacacttc ctgccacaga agtttttctt tggagttgta tttaatatac tttcttctga  12840
aactcactag tattcctgct ggtcttgcat tttccctgag aaatcctgtt gagctggctc  12900
cgggtgcatt tggggagaaa gtgttgcggc tgggctgtct ccctcagttt tggggataca  12960
atcttgaaat gtggaataac caacagaaat gtcttcttca gagaccatgg gtgggtgatc  13020
gctggactcg ctttctttgg aagctgcttg ctcctctttc tgcttatgcc gggcaacaca  13080
gagctcctct tgaagtactg aaaatcctgc agggaagagt aattgaaagt attgtggaat  13140
ctcacttaca ctaggtgttg taatttaaaa aaaaggcagc tcaagagaaa gcgatgccct  13200
gagacagagc tcatgtggag ggtttttttt aattagggga aaggaaatgg gaccagcctc  13260
tggggacaga caggagcatc agaagagaat ggggggcaga gacaggcaga gaagcagaga  13320
gagaagatat atcagaagga aaaaggaact ggaggagcca cccatggtag gaaagattga  13380
acagaggggg taccaaatgg aatctgaggt gttgatgggg aatgtgcttc tgtgtatatg  13440
tttctcttat tggttgatga atagggaagc aagataggtg ggactaggag tggaggagga  13500
ttctgggaaa tatagtaaag agacgaccat gtgatccagg caggaagtga tgtagcaggc  13560
agaatcagaa tataagcagg gacaagcagg aaattgctct ctctcttctc ttctctgtgg  13620
agacactgag cagatatgat gcagacccca acagagtaag aggcccagac cttatctccg  13680
gtaagacaag gccacaagga aatacacaga ttagtaatta tgggttaaga ataagaaacc  13740
caagttgcca gccaacagct tataactaat atagcatctg tgtgtttcct ttggggcaaa  13800
gaagggcagt gggacctagc cagccaagag aaaacttcac attacaaggt ggcatggaag  13860
taaatacatc atcaccaaaa gctatggtct gttgtaaaaa aaaaaaaaaa tggaggcagt  13920
aggtccatct cctgaattat cccctactcc taagagacac cactttacct tcactgttgt  13980
ccagtacaat ggtctgctcc atttccgcat agctgtggcc catgcgctcc tgcaggggtt  14040
ctgtgttggt ctccaggaga tgtacaatat ccatcctgtt aatcttggtg aggcattcaa  14100
tgaggatggt atctgagaca ttagagaaaa ggcattcttt gcatatgagg ggtactcttt  14160
ttaggaactc tttcattcag ttgccttact aagttcttgg tatttacagc agagcctagc  14220
aaactccaac taggtccttt gtaaatagag gcaaatagca gagaatagac cccacatact  14280
acaaaccctg aaggcagagt tgctagataa gacacagggc acagccccat ctggattcta  14340
ggtaaaaaca aagactttaa ctgtatctca aacactgtat atttatatta tatttatatt  14400
aaatatattt tttaaatatt tatattaaaa gatatttgat tgtttttaag ttaaattgaa  14460
tacccttctg tttttattgg ctaaacctgc caatgctgct aaaaaggatg tggggaaaaa  14520
agaaacagca ggagatatta aggcagatct tcacagagac atgaaaggat gggctgaagc  14580
```

```
tgggtggcag ccaagttcta tctcatttcc catttaattc cacagggtca taatcatatc  14640
agtcatcaca tacagtatct acttgattct cctcccccat atatctaaat ttctagagag  14700
gaatggaaac atgaactgca ggcagtacac tccccataaa taattgtaac cgtacaactg  14760
tgcccgttaa ctaatactta gaaactgtta ggtctcagtg aaccttccac agtggctggt  14820
gctcatatca ttgccactgt tcacaaacat atcatgcaag atttctcatg gaacaagatt  14880
ctaaaaaaaa tttagaaaga taataacagc ttgttctcct tcactgacag tggttgttaa  14940
aattgatgac ttttgacaat ttatcttact gattctgtaa gaacgggatc gttgggggat  15000
ccacttccac ctttgtctaa aacctccacc ttagcatttt cccaattacc tgtggcatgc  15060
ttcccatccc tctccaacca gtacttcagc agtgcatggc tctggtcttg aagggagttg  15120
gggttctcaa ttcgaatttg gtgaatttgc tcctcagtga aatccagttc tcttgctaat  15180
tctaaaataa taacaacaaa atgctacgtt gtcaatacat tgacttcatg tttgagtctc  15240
tacaccttgt tccatgatgt gtaagtgata tggtcttgtg ctgctttgag catttaggtt  15300
agaagtgact cacacacacc tttgacatat taaaactaac aacctctccc tattaaaatt  15360
ggatatagaa ttaattactg ccattgtaga aatagtgaag gtgaaggagt gatggtgaaa  15420
tgtaaatgga gatcagacca ttattacttg tttatatttt taatcaggaa aatgaaaaat  15480
aagtgactga acaggagaag tgaagcattt ctcactttta taggttttta actttaacaa  15540
atcctgtttc tggaaatgtg tacaaacatt tgttgtagct aatttacagt gatcgggtat  15600
gctcctttct ttgatgtata tgaaggaaag gtctgtggaa actggtgtag agtagaagtc  15660
aaaaagattt ctttaaaaga tgggaatagt ggtacatacc ttgaatccca ggactgagga  15720
ggcagaggca ggtggatctc tgtaagtttg aggcaagtct ggtctacata ctgagttcca  15780
ggatagctag agctacatag agaaatcctc tctcaaatgt acctcctata aaaagtttgt  15840
ttattttact ataaacattc tatatgaata cttgatgctt gtgcatacta taggtataca  15900
tttgtgtgca aaagcaatga cttctaatgt ctacctggta tctttcaata ttaaaaataa  15960
cccttgatcc agtaattcta ttttagaaat gtatttcctt ttcctttatt ttcattctgt  16020
tatgttataa ggtttaaaat tttgccacct ttatacttaa cacacttagt atgtgtggat  16080
tctacatatt caaggaaaaa atacatatct aaaatgccaa ccagagatat tttggtatca  16140
ttctcttctc tgaatcctta tatcaggtat ttcaacatta ttctaaaatt accaaaagtg  16200
agaaaatggc tattcctaca gcttctagtc atttattcaa aattatgaat catctttgag  16260
gataggctct tatttccttc taaattttca agaaactgat agaaaagtag taactttgca  16320
attttttttt ctcagcaaag cacatccaag tgatacttaa gaaaccaaat cagagtcaaa  16380
aataatgaaa acgaaagtaa gctaggctat aatattgcct aatattaagt cacaggtaga  16440
tgaaaattta ttttaaattt ataaaccatg atttgtaaat agcagtatgg atattagaat  16500
tcacttcctc ttaataaatt accaagcgtc cctacctcaa aaaaatggtg caacatatgt  16560
gttttaacat tcacccagag cacatgttaa tactatttac tatgaagaca cctaacatca  16620
aacatcaaaa acaagcagca ctgataaaaa tctcaaatgt tatgaaaaat tgccaggcat  16680
agtaactcac acctgtattt acagcactgg agcaggtgga ataccatgac tttaggacag  16740
cttaaggtat attgtgaatt ccaaatggac ccctgggcta tagattaaga acctgtctaa  16800
gaaaaacaaa aacaaagatt ataaaaattg aatctaaaat tgtgtgaaac ctgggtattt  16860
tcccatagct tagctaacta taactagtag aagaggatgg gtaaatgggt ttattctcaa  16920
```

-continued

```
agtcttcaac tccaaagttc taaattccaa aactgttaag aaccttatac tcaggccaca  16980

caattagcta ctgtggttgg atttttcaac ttgtagattt ttcctcacac tattctttat  17040

agtcttccac aagaaaaatt aagagaaaca atctttaaca gactgtttct gtagagaaac  17100

tggatcacac caattacctg tccaactgaa gccaagatga tcagcaatgt aagccagcct  17160

ttcttcaatc cgttcctgtt catcttgggg atctacagaa ggtcaaaaac agaatggaca  17220

aagagtatct gggacaacaa gggagccaca gtactaatca tccaagaaag gaagtcactt  17280

gaccaagtct ctgatagctc tcatggttca ggttgtatgg aaaggtgtgt tttctgattt  17340

ctggggtaga atggggaatg aatcccatgt ggtgacttgt ggaaaccgtc tccttcctta  17400

tctctttaat gaggactaat aactgaacag aacgtccagt tatttcaggg cttccctttt  17460

acacttttga aaacacggcc caccagagca tactcatttt gcaaatgaaa caccagaaaa  17520

atggccaatg gattatagaa gcggagtaag tggttgggct ctaccactaa tgcctgagga  17580

ggtgtcaatc accatcaggt cctggatgaa agaaagcact aagaattatc ttagtcatgg  17640

ttagactgac cagcctggcc aggaacaaca ctgtcctaat gaccttggta gaagacaaga  17700

taaaggcatt tgaactttgt atgttctgct gctatgatat ttgcttctga ggcaaagttt  17760

ctggctgtct cttcctatgt aaagttttca ctaccacaaa ctagaattca tcctcttccc  17820

ttttaatgac catggattaa tgggcagcag caggaaattc tgtcacccac atttaggagt  17880

tagtcttcat ttggagatag tggaagcctg caggttacct ctcaaagcca cccatggttt  17940

cctttttttt tttttttttt ttttttcaat tccaagagcc atcattccct cacatcatgc  18000

aatgtttgag attttgttgt ctgctgaatc tcatctgaac acattcacaa tccatctgct  18060

tcacaactca aaagtggatt tttacctcac gtttgtttgc ttaatttggt tatcatggta  18120

tctgaaagcc aacctctctg aattggaaaa cagacccata gtaatttcag gatgtgagca  18180

atcattttga gtaaagggct ttttaatcct gacaaaattg aatgcaccaa ttatttaatg  18240

aacacaaaga aaagagttga gagcactgag tccttgtgct aagaaactca catgctcatg  18300

tgcaaaacca aaagttttta acttgaggct aagcctggga cttcagaaca acaaaaccca  18360

aagcttgtat ggctttacgt gcagcaacta aagaaaagca aggtcccccg ttgcttggtt  18420

atgtttatgt ttttgataag cattctcatt actcaatctt gagattgttt catagacaag  18480

agtatacaga aaaagcacaa aacacaaagg gcttacacaa acacattaac cactacagaa  18540

agcttaaagg aaatgagaca caaatcacaa aataaaagaa acattaccaa aaaaaatctc  18600

tatcaaattt atgacatgcg tagcacaggg aatcccagtg gctggcaaat accttcagct  18660

cggtcatggc cattttcatc agggatgcgt tcaatcatag tctcaatgga ctcatcccaa  18720

atgggccttg tgtcaaagat gtcctcagga actgaattct cagtctcaac aggtggcaga  18780

ttctcaatga ctgacacttc cagggcacta ctactttcat catctgaagg tggctcctgc  18840

tccctttctg actgtgtgag cctgtccact aatttggacg cctcatcact aatttcctca  18900

aagaattcta tggaatttct ataaaggtca aagaagtgct ccctactctc ttttgtgggg  18960

ctcatgcctg tcctgctgga agatggagtg cttctgctct taactggtaa tcgggatgca  19020

aatagctttg gttttgtggc cccttcttct gattctgact caaacccttc tgctctctcc  19080

ctgctctctg tttctgtctc aatgtaactt ctggctttta ctgggcattt ggtcttagca  19140

tccaaaggat tagcatctga ttcagatttg cttctaccat ctggtgctct gcttagcatg  19200

tcctgtccct ggggaacagc tgtcttctgg agagatgtgt ctggatagga gagctgccac  19260

tcagttcttt gggtgggtgc tttgatgggg attttggact ttggttttgc ttcatcctcc  19320
```

```
ttactttcct catccatgcc agatgggaaa tcatcagaaa atgcactctc atcctctgta  19380
gatgaaggga ctgggactga agtggagagt gtccttagag aaatttgagg tttgctttca  19440
gcagaaggca cattttccat gggtgcagta gggatctcaa tcacagattt ctgttcctct  19500
ggggaagaat ctggggactc gtcatcccta tctgaatgaa cagacctagt gactgtggaa  19560
aagtccaatt gaacaatagg ttgggggaag gcagggcaag gtgtctgctt cacagtgctc  19620
agagaagatg tatcactcag ttgcatggtg gggaggtcct gagcttctgt ggatacagcc  19680
tcttttgtgg gcatttcagt ggaagctgaa atcatcactt gggagtcaag gttagtatct  19740
gaggcaggta attcctcagt ttcctcactc acatcatcag gaagtaattc tccctcatcg  19800
tctacttctt ctttggattc tgaaagttcc agtgactcac ttgtgttttc cggctgtgtc  19860
ggctcagccc ccatggtccc ttccttcaag tcttcaggga tagtctcttc attggattct  19920
tgaccaattt ggaaaaagtg caaattttca tctgtatagg accttttggt catatcaata  19980
gcaccacttc tggtcatctc aaacaatttt ccttcctgga agaggaatgg attttgttca  20040
cttgttgggg ttccctcttc agttggggtc ctagcaggag tagtatcggg agtagtaccc  20100
tgtgattgtc tgtctaccat caaaccaaat attttctgtt cttcctcttt cactctagct  20160
tcaaaggctt catcatcttc acgaatttca ctccaggagt cagaatccac atcggttttc  20220
gtgatgatga ctttgctcac ttgctcacca atgactgctg gtgcatttgg tgtagcagat  20280
gctacagatg tggaaggcac atctgactgc attccccaca agctggtttt ttcctcggat  20340
tcagttttta gaccctgggt ttcaaatttt gattcttggc ttgagacagc tctaccagag  20400
gagtttgtct ttacaacatc ctcagaagag gatctgatga caacagagaa cacttcaggt  20460
ggacaaacaa ctgtggtgtg acatgtgtct gtttggattc tgctgtcctc accagagaaa  20520
aatgatgagg aaggaacatt ttcataaggg ctggttattt gaggatcaga attttcatca  20580
gtctcagcta aatcagacac cagagtgtct gtatcaaccc tatctgtttg agttgtagaa  20640
gatgagtctt gagtgggaca gtccttcggc atgcttccca gagtctgatc agttactgtg  20700
acgtctactt tttcagtgga agatggggag ggtacttctt tcactgattc ctttctttca  20760
gatactgcac aatgagatga agaagacagg gaagagcttc caccggggaa atctgcctgt  20820
gtagattcca ctccagaagg atcaagctct ctcccttttt cccaagtatc ctggagagcc  20880
agtgactctt tatcaatggc aagctgttca tcaacatcaa tacatgctgg actctgaact  20940
cctagggaga caagggtggc tgacttgcta ggactcacaa cttcacaacc atggccatca  21000
caggtttccg accgatgagt ctctctgttc agatcatcat aagacctatc aacaccatca  21060
gcagaaggag tccgacagcc ttcagctaaa ggagattggc aatctttgtc ttcttctgac  21120
ttacccggct cctcttgaat atcttcgttc atcttgaaag tgtattgttt ggaaactata  21180
ggctggaact gtgattcttc agggctggaa ttagagtcta tgctggatgg gaggggagat  21240
ggaggttgaa ctcgaataac tggttccatc agaagccctg agtcggcacc tttactcagc  21300
tgtgtcagct caggctcact ttcagaggag gaagaagctt ttctgctctc cgaagtcacc  21360
aagactggga cctcagtctc cccttccatg gtctccactg gcttttgttc atccacttct  21420
accgaacagt cagcatcggg gtctgaggct gaagaggagc catcttgtct gggttctttt  21480
ctgtagtctc ttttctgctt tgcttcttgc tcgagttcat caaatgtttt aattttggtt  21540
accatcttga acatttcctc ttctggggtg aacctctttt tctccccatt ttcagagtcc  21600
tcctcctctg cacactcatg aatcacagct ggcttgggta aacttgaatc tgaagccttg  21660
```

-continued

```
ggtgtgacct catagctaac ttcttctgaa ctgggagtgt caggggagag ggggcttttc  21720
cctgagctct ccatgagtga agtctgttca agactgtcgt cctcggcact gccatcaggg  21780
tctcggagca gccgagaacg catggaagcc acttcagcaa caagatctgt tttggcaata  21840
gctgcaggga gaggaaagtg acttgggaga attcctgcct tcattttggg ctcaactggg  21900
ctgctttcaa gggagtccct gcaaggggat tctttcagag gacttggttc cagagaatcg  21960
ggagttttgt gtgaggagtt atcttccaac acagggctag cttctagaga gtctttgtgg  22020
cttactgcta atgattcatc ggccactggg ctgagggtct cactatcccg gctagggagt  22080
ggaagttcta acccttgggg gcttctaata gctccctggg gctttggttc tgttccctca  22140
cctgccttcc cagaagcatc agatgatgag aaggcctttc ccacctcgga gggagtggtg  22200
gattcctgag tttcactttt tgcttgtgtt ttacaagctg aacctacaat tgggagctga  22260
ctttcgtcac aggacccttt ctcagtaaag acttggcatg tttcatctgc caacgataca  22320
ctgtgcctgc tagggcaacc atctagtttg gaggatacat cttgggaagg gtcttgggtg  22380
acctccttct gacaatgctc agtagaggtc tctgaacccc cagtgaccac agcaccttgt  22440
gttccagaac tatcagtaat gtctttagtt aaaggaagct ctttttctga atgaatttct  22500
gtgggcattt ctaccttagt ttccttgatc tctccaattt gttcctcact tttcttcggt  22560
gagaaagaaa gactctctgg acttgtctcg ggagtttctg ctaggccctc atgcttatag  22620
ctctcttctg aactgacctg aggagtacct tccatcaggc tgccacaagg cgagcctgct  22680
atcacttcct gtttcaggct ttccaaactg ccagccaaag caccactctg taaagacaga  22740
gctggaagaa actcgtcttt catgtaatct agagggaacg ttgtgttgaa aggacttgtg  22800
attacttggt ctaagtgtat ctgagccttt tctgtttcct cagtgaggcg gaactgctga  22860
tatttatcat tgtcttctaa ctcttgcttg atgacatcag agaagtcagt ggaggtcttc  22920
ctgtctgggc tgatctgaag atccatgtct ccttgctcat ccatcatctt gtcttgaagg  22980
atctcactgc cccgagggct ttcttctgcc accactgatg gaactggctc aggtgtttta  23040
ataatgggag ctctctcaaa cttttctcta actggatctt ctgtcctgag cccaacagtg  23100
atggtagtag aacggaacct tctggattct gtaggtgccg tcactggaaa tctctggcca  23160
cgcttgattg tctggctttc tgttctctga gactctctct gggttactgt gtgccccttt  23220
tctttttctg ctcgggtttt acttttgtct tgtgattgct tttgctttgt tgatttgtgc  23280
tcaaagagtc ctgttttgtg tttagacggg tcctgacctg actggaatgc tttcatcaac  23340
tcccggacag acattgtctc ctcaattcgt tctgttttgg aggtgggaga tacaggtggc  23400
tgcttttctg tcttcccagg tgacacagga aggtgcttat catttttccc agactgcttc  23460
tctgaggttc ttgcagaagg tgaaactggc aagcgttttt ctgttctccc aggtgacact  23520
ggagggtgtt tctctgttct tccagatgat ggtactggag gacgtttgtc tgtttttcct  23580
gaaggtgaca caggtgtatg tcgttctgtt tttacagatg acacagggga atgtctttca  23640
tttttgttg agggggatcc aggtgaatgt ttctcaggtt tacttgacga tactggtgag  23700
tgtcgttcat tttttggcga gggtgacaca ggtgagtgtt tctctgtttt gcttgatggt  23760
gacactggcg tgtgtctttc agtttttgca gaggaagaaa aagaagagtg cttttctgtt  23820
ttagaagaag gagatgactt tgaagagggt gacacagctg ggtgtgtcct gggcgtggtc  23880
tttttgggca catcctcttt gcctttgact ctgaccggca gcttgcttcg acctttctgc  23940
tcatcttcta cttttttctg aagagccttt actttgtcct ttatggaacc aataggagtt  24000
tcttctatca gaggagaggt ggccttggca gtgggaaggg gctcgggtgc caggcctcgg  24060
```

```
tcttcatcta ccgactcctc tgaactacct ttcctaagtt cggttgtttc ttcactgcct  24120
tgggaacctt cctctttttg tttctgcttt tcttttagtt tcctcctcac tggcttcttt  24180
atcaccaggc ttggttttgg ctgcttctgg gcactttgtt tctcctctgc tggcacagtc  24240
ttccctttat tattctcaga ggtcttggca acacctgaag cctgacttgt ctcccctgtc  24300
ttttcctgag ctgtctgtgg cttcttttca tgagaagaag tatatgaatt taggtcttct  24360
gttaggtagg tcactaaccc agtggagtcc ttctctgatt tgaccttgga ccctctgtct  24420
actctgactt ctatgcatgg ctgttcagtg atttctgcag gcgcatgttg cttggcctct  24480
tggatttcct catcactgac aatgacccat tcctcttcta gctcccgctc agactgagaa  24540
gtctgtactc tgccttcttc tctaacacag gccccacttc tcaggattgc gtccactttc  24600
tctaagtcct ccttaaccct ttcaacaatt tcgaatggtt cgcctggctc ttcttcagca  24660
gcctttgcca gctccttcac cttgatagaa cctgccttat cggacacatc tgtggtcaag  24720
atggccgtca ttttgatcaa atcttgtttc atctcagaaa cttcagagag caagtccgga  24780
cttgctaaga caggaacttc attaaccagg tggcttttca ggacagatgt ttctgttgac  24840
tctgtctcat catctttgat gtgaatgaaa aacattgaaa gtaaaatgga aatcaaaaaa  24900
gatatcggca aatgtaatca ggaccaaaac aacacagcgt cttttcctgg tggtggaagg  24960
ggcaacagaa tgggctggga atggtgaatc cacaaggtct caaggaacaa gagcaaagca  25020
aggctaacag aaaaaaataa ctgaaaagga aaatgagcag gaaataactt gcttaatttt  25080
ctcaattgta gcacattcat acatacaaca aagctatcac aaatactcaa gacatacata  25140
aaaaagtcac aaatcaaaaa gaagagagca gtgaaattac acagaggtat ctcaagattg  25200
tccagatatt acagatcaat gtcagaaaat aaaacaaaac aagaaaccat ggggaaaaaa  25260
taaaaaaagc attagaaatt gcagaaactt gatttcctcc ctgagaaagc cagtaggagc  25320
aaattcagaa ttgcacccaa ctatgtccat acattgtaaa tcccacaggt ctggaatttg  25380
atcagcatag tcctgccacc atacagcaat ggcagaatac acatctgaat cagcagcaga  25440
ctggcatttc atcaaagaga aatccacacc taacgatgac acacatctcg tgctgagagg  25500
catggccctt tccttggagg aacctccttg tttagagatg taacagacag aacaaggagg  25560
aggataaagg aaaggaacaa atgacagaaa caacagttgt gactgaacat atatgtgagt  25620
tcagagttaa aatgtgatgc gtggcaaccc aaattagaga cagtcacaca ggacacacac  25680
acagttgatg taagccaagt tatttccatg caaagcaaag gtggaataaa actgctgggc  25740
aggggacagc cttgcaggaa agtgcaggca ggagggtggt gagaaattag aacaaaaatg  25800
taaaacgtta ctgtggtgaa gcatatttag ctccctaacg atccatgcat aaggtggcct  25860
gtgcaggttc ttttaattaa tacaaatgca agaaaccctc agggttggct tatataaaga  25920
cttgagtaaa gagagagtcc ttctttggag gttattttgt cactatatga aaatcatgta  25980
agggttatct ttaaacagaa acaaacataa atctgcattt aaaatctggg agacatttaa  26040
agtttctagg tgtcattcaa gagaatcatg gcattatagc aacatgggaa ctttactgcc  26100
tttttaactg gcctagacca ataatttcaa ttcctaatag tttatatata ggagtaaagg  26160
aaggaaccat ttaagtcaat acaataatcc taaagaagaa agagaaagag gaaataaaaa  26220
cacttaaaaa tcagtgaagg tagcactaat atgtgtcata aacaaaggtg ccttctctgg  26280
agagaatttg tatttgttca gaggcaagca catgtgaata tataaaatat attaagatca  26340
atttatggta atgttgattt tttagttata taaactattg aagacatcag aatctcagat  26400
```

agtttcatcc tgaatgaaga agaacatgac gataaacctc agttaaagcc atttcaatag 26460
gacaatagta aattatagtg agctaagact tcagacaaac aggccctagt tggtggctgt 26520
tttgtgaggc ttaggcggta tggccttgct ggagtgtcac cagggttggg caggctttgg 26580
ggcttctgga gtattcattc tgcctgttgt ggtttccaga ttccaacagc ctgccaccta 26640
ctacctctgc tctgccatca aggaatctaa cccttaggga ctgtaagccc aaaataaaac 26700
tctttcttca gtgagttgct ttggtcatgg tgtttatatc acagacacag aaaagtaaca 26760
aatacaatta gctagggcta aatgaccttg acatgtgcct ctgtgttctt tccgaattgt 26820
tacgctggga tatggtgaat caaaacaaat cttaatactt aataaaatta aaaattagaa 26880
tattttctca ggtggtttaa tgcttaaggt agagaaaaag ctataaaatt caacttgggt 26940
tcctatacaa gatgagacag ttacaagaga ctagactaac gagatgaaat gttaatagac 27000
tatcacaaac ctcaggtgaa tttagggctg gttactgcac tagattttgt tgggattttg 27060
agttgttatt taaacatagc cacacaagga cacattgtga acggtaattg gatccagtat 27120
actttaattt ttccattctt ttctttttc ttcttttctt tccttggaaa tgttcacaaa 27180
attctgttag atctcaccta aagatttagg tacacttcac cacagtaaga gtgcaaggat 27240
ggtagagtat ggggggaggg gtgcatgagc ttcagctaag aactatgaga cagtatcgct 27300
tttgtaggca tccttccaaa ggcaaggctc actacagagg tcactgtagc tttatgtaaa 27360
aagtaatact gtcatgtcag tgcttaaaaa gaaaagaatg aggtaacaat gttatgctaa 27420
caaatggaca aaacgataga gtagctttgt aaacaagctt tacagcaatg ccaggggtta 27480
cagggatgtc aaaagaaagt gaatgcttag atgaataatc attgcattta ttgctaatta 27540
gctcacaaat taggtatatt tatgatttaa ctggccaagc tgcttttata agtatatatt 27600
aatgattaat aagaattaca taaaattaca attattatgg tagttagtaa tagcaactag 27660
cttgcatctt aattcatgct tcttttcatt atagccatct ttcaaacaaa ctcaatttta 27720
tttaaaaatc ttactttttt ctgatgtcat accgatctga aagaaaacat acacaaatac 27780
aatggttaca cacagctctt ggctcaaagt cctttatgtc ctttatccta tttgtaatat 27840
gaacatagga gtataataag ctagaggaaa gtcagaggca ttagctacag ttcctgtatg 27900
tagaagcaaa catatattca cacatcattg ctagatactg caggaagaat atgttaatct 27960
tgggaagaca tgaccccact gtgtttgatg taagaattgc gtattaggga aaaggtcatg 28020
aaaaagttga agtcagtctt cagcagtagt ttcccattta atgaggggaa aaaaatggca 28080
aagttttgct gggtgataaa ttctaccaaa gtcatttcgt gacaacagtg agccactgtt 28140
ccaaagcttt tctcatattc cttttaggaa gaacagaaac ttcctgaggg tatttcacag 28200
gaaacactgt ttatctaatg gaaatggttc agctgtgaac acagcaaagt tggtttcatc 28260
acttgtatgc tcttttgggg tgtaggtgcc acattttgag aggcagggtg atagaatcac 28320
tgagcacaga agtgtgtgac agtgacacac acagggagaa gaccagtcac acatctgctg 28380
gtgtgtgtga ctgccattcc acatctgttg tgtagcttcc catggcataa gcaatcccct 28440
aaactaaggc catgcattgt aagttggtaa gtaccgaaca tttattgtgt ttttctttgt 28500
atttttacat ttcagatgca ttggcataac ttttaaaaat ggtatattaa aaacatgcac 28560
tgatgataat tagtttggaa acagttgagc acaagaagga aacaggagtt gctatattaa 28620
tgagtaaatg taaggaattt tccaatgatt tctttcattt ctgtttcagt gcctagtttc 28680
agacctttag aaagaagaca atttacttta aaaattgaag tgtgtatcac tcagatatct 28740
attttttaa ggtaccctct ttagaactta ttttctatat ttgtatgtaa cttgacacag 28800

```
aagtcaggtg agataaaccc atgctgatga ggtatgtgga acactgagtt ttgcaaatat  28860
actttatgag gaaatgtttg ctattagtat atgtttatat tataatcttg gagtctagtg  28920
aatgtactat gtgtttctga acattagtta gtcttagtaa ttctcagact tggtgttagg  28980
accacagtat acatctaaag ttactttcat taataagcta cacataaaca aatctgcata  29040
ctgcagttaa gagctgagaa gattcaagaa caccacaatt acactaacac actacctagt  29100
aattgccaga gtgctgaagt catcacagtc ccacctcaga aagccttgct gctagtgagg  29160
ctatgagacc taaaaagtaa actgctgtat ctgatcactg ttaccttcag acaacttcag  29220
tctagccttt gagtgtcatt gagacatggc ctggccttta ggagttggta gagaaatata  29280
tactattaca tagagggcta cagtaaataa agaaactttg cagttttctg aatgtcattc  29340
acaagatgga gaaaaatgta agagaggggg gattgactaa aattctgttc atcaaattgc  29400
taaggacagt tgcctacttt ctaagaatca gaggccaacc atatgctctt attggtggct  29460
ccaacaatga tatagccagg aacaagtgac tctgttgtaa aattacctct tcctcctgct  29520
cttgatctga ctctgattcc ttgatgcccc aagatgccat tcgagatgga aaaaagggaa  29580
aaggaagaaa actttttagaa ggaaggaata aatacatcgc acctacaagc atcaaggcag  29640
gtacacagta cactcagact cttttcttaa acagtttcta taagacaaac agttaaagaa  29700
gattgatcaa agtttataca ttcaaagaga caaaaggaac aaatgataaa tatactaatt  29760
ccagacccta ggttaaaagc agtctcaaat cttgatattt aatgtgtctg gtacaattga  29820
tttacagaaa tggtggtgac actatcccac ttactatgga tactgactga aaatgtcaaa  29880
tgacattagt aagtttatgt tgaaaacatt ttcaatacat gggcactaca caagtttcat  29940
cataataaaa agctacggaa ttctcagtat atcataaatg tgcaatgttt ggcattttat  30000
tcttttcatc ttgaattact aaatagaaac cacccctgac caccatagca ttaataactc  30060
tgtgagctat gtctggcctc aaagaatgta aaagaaagta aatgcgttct ttcacagcat  30120
ttggagagct cagagaccag tgaaagcaca ttggcactaa tatctctggg tagcttttgc  30180
atctctcctc agtaactcta tcaccagaga ctaaacatta aagtgcattt gtgtcatggg  30240
atcacatttt cttggttgat ctatctattg ctacattcca attgcattga aacatcatgc  30300
atattatatg tggaaataga tattaaattt atttttaatt tctaagaaga actaataaca  30360
tcaaatatat gctaggagtc ttcttctata caactgacct ctatttccaa gaaggaggat  30420
ttaaaccaat acatactgca gcaactatga tggaggcaaa gctaatagag aatccttggt  30480
tctgcagact caggatagaa agttttaagt atttccctac ttcccctcca gcatccacta  30540
ctcatccctt ttccaagtgc agaacaaact gaacacttgt agctgttatg cacagactat  30600
tatctgcagc tgtctatttt taaaaattag cttaaaggtg gggggaagct ttcagaataa  30660
gatttcccac atcacttaac tgatttagtc gccttctttg atacattcag aatagtcaaa  30720
agtattatgt catagagaaa gagttagata caattaacat tagataaatt tgcatcagga  30780
attaacaaac ctcctcctag tgctgcaaca attgtgatct tctcaagaat atgtttttag  30840
acagatcatg ctaagttaat tgaaaagcta gtttaaaatt cttcaaccat taaaacagga  30900
cagactataa tataaacagg tgattggttc aggaaaaggt aaaattctag tagtatgctc  30960
tgaaacttca agctgaccca gctctgagtg aacagtgaat ataagctaac actctaccat  31020
ccaggtggga ggtaatgcac caagtagcct caggaatgca cacagaaaca agaacaggga  31080
ttgacaacac cagttatttt ttctttacaa cttagctcaa aaagcattaa gattaaaact  31140
```

```
catcttttct ctgtcatatc taatatataa aaattaaagt gcattaaatg tcaaagaagg  31200
tgggaattgc tttttctcta ctgaattgaa aaaaaaatca ctgaattggg tagaataaca  31260
aaaatgattt gtacacgttc ttgtgttcaa tgtcttttat aaagaatctg aatcttaatg  31320
tctatgctgc ctgggaacac tacagtattc acaatacctt tgcataaatt ggcagggtga  31380
tgttcaggtt gcaaatggct tgatgcacca atcctcttgt ggatttcggt tccttcataa  31440
atgatagtcg cccgcaaggt tcctgagttg tatcacgtac cttgagtgag aaagacatat  31500
gtgcttgacc tacgtttgac agcagatgag gtttaaagga gaggggggaa taatttcaat  31560
ccagtaacac ttaaaggata gacataagat ccacagacgt aaagcttctc cttttctact  31620
ttggtgtcat cattgtcaat aacactttga aaatgtcttt caggcatttg ttgctttata  31680
atgtacaatt gaaaaaaaat tgtaccagga tggtttgcta tgcacatgat gtgaaatgaa  31740
gctgaccatc atgctaactc acaggccttg cctcaaatga aacctgccat ttgtttgagg  31800
agaggatgct tcatcccttc agatctccca gcaaacttca aatataaaat aattataaac  31860
tatggctaca tttctgaaca ttaggtttcc gaaactaatt tacctttttt ttttttaaaa  31920
aactatggta aaatacacct gccataaata aaactgtaca tttctactgt tttctaagtg  31980
ctgtgaagta agctcatgaa gttgtgcaat caccactact ccccagtgct ttctattcac  32040
ccaggcactg tgcccagtac aattttactt tccattccct gtccctggca acccccactc  32100
cactttgtgt ctccatggac ttgcctgctt tgtaaagtgg actcacatag tattttcctt  32160
gtgttttact gacttagcat aatattttta agttcattgc aacatcaaaa tttcattcaa  32220
tcattcactt ttagctgtgg atttgtaaca ggaaacatca tttcagatgt accattcagt  32280
ggtcgaagta cgtgcatttc attgtatagc tatcagcact atccagaggt gtgccgaggt  32340
tacttcccaa actgcaagtc tctgcgtgga aagcaaaaat tcctccccac catattcctt  32400
tccctaatag ccaccctttt actttctgtc ttcatgactt ttacttccct gggtatccct  32460
taataaatgg ggctattcac tatcaaactt tctattacgt tgaattgatg aaagtgtatc  32520
aagtctatag ctttaagtag aatattttct tatcggacta tgagattctg ggtcttttga  32580
gaagttatta caaaaagttt ttggtgctct tttggtctag tgacattcac atacttttta  32640
aactctaagt atgaatatat aaaagtcaca gcagtgaaga aacagaaggg ttgggagttt  32700
aagtcactag tagagttact ccctttcaat aactaggcat gaggccctaa gtttaattca  32760
cacacacaca cacacacaca cacacacaca cacacacaca agcacgaaga gggagagaaa  32820
gaagagaggg agagggaggg agggagaaag agagaaatag agagagagag agagagagag  32880
agagagagag agatacttat atagctggtc ttgacagcta gttattaagt gggatcaaat  32940
ctgggaaaca gtatttaatc ttatactctt aatacttagt aacttggtca tagtttctcc  33000
tcattgccct catattgtgg tctctcatta aaatatatgg ttgactttgg acttcaaaaa  33060
ttttaaaaat gtatgttttt gtaaacattt gtaaaaatat atttaaaaac tactggaaat  33120
gtttgagaag cacatattct cactatgaaa gtaactgaaa acagcccttg tacatgagca  33180
aatgtttaac tgatttttat ttttgtatat aaattacctt gacaaagaga ggaagtctgt  33240
tttctttgaa ggcaaaaaaa ctgaatatat gatgttggcc actcttggtt agtggtacca  33300
gattgccaaa acaatcaaca taaataggtt ttccttctaa tacctaaggt aagacagaaa  33360
accaacacag attaagacat ctacaatcat ttttatgaca tttattctaa caagtagtag  33420
gtgtacttgg aatcttcggt tcttagaata ttcataggac gatgttcaca ctgctgattg  33480
acatctgtca tatacatgct ttgccataca tagtaccagc attctttctt gctactaaga  33540
```

```
atcttcaatt gtatggcaac attcaatttc tcatttttat tgttgtataa agatacccat  33600
aaagaccaat atatgtctaa tacctaaata taaactttgt attgggtaac tttgacatca  33660
tgataggaat cccggaggac ttcagtatct aaacatctac aatgatggaa agttctttac  33720
aaaaaaaggg aaaaatcaat gtagacaagt atttagctga ccaaatactt aaacaaaaag  33780
aagtacttta aaagaaaatc caggaagctg aaatcacaga aactactata gttattataa  33840
actcatagtt acctatagac tcaaagttta tcaataactt atagtttttc ttcagataaa  33900
ttttacagaa atccttctac atacagagag accatccatt tatggtccaa attgtcagaa  33960
aaatctctga tttgggacct tgacctttaa gtgatagaca cacaggctga cctttctttt  34020
gttaagcaaa tctccctata tctgttttgc aagtgacttg atagtgaaaa ttcaggatgc  34080
agcatgtcta tattcttacc tccacatccc tgctcctggc cacctcagag aagttttctt  34140
gttgctcaag ggtcttatct actttatcat ctgtcataca gaaacaccgc aaccgggctt  34200
caatggggtc atgtgatttg gcaaagacta caaatttggc catatatggt acacagataa  34260
tttctctata cacttgcgat gcaaaggaaa cagattcctg aatctgccga caatctatca  34320
gccagaacct acaaaaaaaa agaaagaaag aaagaaagaa agaaagaaag aaaaccagtt  34380
acctaagtat aattatgcca tttgacaaaa aatagaaaga aagaaagaaa gaaagaacga  34440
aaggaagaaa gaaaaccagt tacctaagta taattatgcc atttgacaaa aaataaattc  34500
ttttaatatg gccaatatag tcatcaaatg attcttgaaa aagaaagaag tgagagagat  34560
agagatgata agaggaccta gataaaaggg aaataaaaaa ggaaatggca aggaagtcta  34620
gaggtatcaa gaaggagaga tatatcagat ttttaggatt gactatgatg aagagagaat  34680
atgttcaatg tacaatatac acttagaagt aaaagtcatt atgtaacata ttaccatgca  34740
taatgaataa atccaataga atacacctcc caaggcaaag taaaacaaaa agattgactt  34800
aaatgttcta gttgtgtttc tcttcttgaa aactcttatt tataaccaat cttttgactt  34860
acaaatcgat tgcttttgga atctttggta ataaaagctc tgtatcagac tatgatatag  34920
atttctttga gtgagttatt cttttccttt attcctctcc taatcgttta atcttctgaa  34980
tctttcaaca tcttttcctc actgcatcat cttccaagag actcaccagc cactgagact  35040
caatcagacc aaccagaaat ttgacgatgt ttacttttcc attaaagata tacaaatgag  35100
aactaatatt agaattcaat tactgtatgt aaaagaaata atagaagata tcttcagcct  35160
cttaaagatt tgtaatatgc aagtgtgtta ggtatataac acattgtaac tacttaacca  35220
cttaggaagc tatactgaac tgtgtgtgtc ttggtattct attgaaaaaa acaactcccc  35280
atgtgttgga taacaggaaa cttctcattc cttggggact gtaatcatca gaagtggctg  35340
ccaaagctat caccaagatc atacagccaa agcagacaga cccatttttt ccatagatcc  35400
taatctgaat gtcagggagg atttggttat tgtgttgtta tcattcatgt caaaaaaatgt  35460
aagccttatt tcatattcga caacaataat caaaatcccc ttgaaagaat taagaaaaaa  35520
catcaaatga caaagagaaa acaatcagtt tggggaggaa caaagtaata tagcaaatag  35580
gcttttctgt gttgcacata catacctggc agacacgttg gttgtaaagg aaacacattc  35640
attgacgaat gttagtggtg tagttcctgt gatgtcttcc cattgtgcag gcgtggttcc  35700
acctgaaata gcatgattgt ggaagacaat tgggcaaaat tccagacatt ggcctttcaa  35760
aaatgtcttt gtgattctga ctgtttacct gtgtgatccc tccatgccac aaaagggcac  35820
aatgggaata acatggactg agatacaggt tagtgataga acatttgcct agtgtgtgca  35880
```

```
cagtcccctg ttcaaccctc tctgccaaat agaaaaagaa aaaagaaaga aaagcaaaac  35940
aactttcagg gctaaggatg tgtagctcag gagtaaagtg cttgcctttt ctagcaaata  36000
acatgctccc agttcaatca ccagcatcag aaggaaaaat aaaaagtaaa tttaattaaa  36060
tcaaaatgaa agagtacaaa ctgtcaaaac tatgtaccaa aaagtacccc ccctcaaaaa  36120
agcgaacacc accttaagat aaactaaatt taagggaagt tatatgaata tctgtttatt  36180
agacattctg tacttgacct gctaaaaaag ggaaatgatt ttcccagtgc tggatcctga  36240
atgtcacaag attgatgtgc taggcaagag tcccccactg gtgcaatggt ggcaagactg  36300
tttatggaga accaactgct cttttggttg gctttgagtc tgatccactg gaggaaatgc  36360
atatatagta ccctaagcat ggtcacagag aagccataag ccctagagga aaactattgt  36420
tgtttttgct aaatgatcat attgtcaaac agccttctaa atatttatgt ttatatccat  36480
atatgtaaac tttggtcaga gaagctcctt actgatattg gtaatggttt gcagagattc  36540
ctaactgctc aaagtgctga gaataagaaa ttgtgagtgc tcaataggag gtgggacagc  36600
tatagcatcc tgtcagggaa catgagcaag aggagtgggg tgggggagtg agaagaaaga  36660
aatagagaaa ggaaaagaaa ggaaggaagg aaggaaggaa ggaggaagaa agaaagaaag  36720
aaagaaagaa agaaagaaag aaagaaagaa agaaagaaag agaaagggga gaaaagaaaa  36780
gaaaaagtaa gagccagaaa atgggaggag tgctgaaatg ctgtctactg ggcatgggct  36840
gttagacctg ggttacctgt acagatcagc ccaggaaaat tgctgcatag ataggaagga  36900
actgtcaggg caccacccat aaatgaggtg atattggcag ttgctgtctt ctgggggaaa  36960
gaaaggttca cttttctttg aggggtagtc actggaagat cagattgcag ctggtggatg  37020
gcccaacact gtgcacatat gggcagcact aataactcag tgggtgaaaa aataaaatta  37080
aaaatattta tttttaaaat gactgcatat aaagtatata atagtttgat ttgtaaacat  37140
tgttgagtat gcaactcatt cttttattca cctagttaat taaaaaatgc ttcgcctgaa  37200
ttaatgtatc taaccccaca gctttttga tgcagggctt gaactcagcc tttcaaatac  37260
tggcctatat tctcagcttt cagggctact taggacaaaa gccactgaat ttttcactac  37320
gctctaaatg ccttctagaa ttttctctgc taaagtcaca tatgactcac ctgttatgct  37380
gcatagtaat cttaaggttg gtgcgtctcc cccaaaacca ttcagcatga catcacttga  37440
agctttgggg acgggaatcg tcatggtaat aggcttgtga aattttcttc tcctgggttc  37500
caaagtgact atagggctga aggttgcttt gttgcctagg atcttcttca ccaactcact  37560
gtgcataggt tgagcctttc aaggtaagaa agaacattaa actatatagt accacactta  37620
attccaacta tcacatccag acattgtttt tcatttcaca aatgagttta atggatttca  37680
aacatggcag ctataagttt agtactatta aagattcaca attaaaaaat tattacattt  37740
tatttttaat ttattttttg tgtgttagaa gtatgtgtgg ctgagtgaat gctacagcat  37800
acatgtgcag gtcagaagac agatgaatct gaggacgtcg tttctcatct ttcatcaggt  37860
gagtttccag acttgaactc aggcttagca gcaagcccct tcaccagtcc agtcatctca  37920
cctgccccac cctcaaaatt ttgtgaatct ttagtctctt gtgttagcct ttgctcactc  37980
aggaaaactt tatttaggtg atatttcaac tctcgtttga aaacctaatt gtaaccctgg  38040
taataaaaat accacagtac catatgcatc ctgcatgggc atacctgcag gcctacacgg  38100
atgcgctttg tgagtgcacc ctctggaaag acagcctgca cctgtgacac cacggtactg  38160
ctcagcactc cgccctctgg gccaatcagg ttgctgtcct gtttgatccg agacaccacc  38220
gcaaagtact gtgggaagtc acgagtgatg atacggcaga ttcgtttctt ttccaggtcc  38280
```

```
tcgggactgt ccagcactga gacaagaaat gatccatttt cataaagcta gtgactcccg  38340
agaacattct agtagactca tgggcacggt taatagtagt caggaggagc agccaagctt  38400
ccctttagtt aaagctagaa cacaaggtca tcctgacacc aaataaatac tgggatcttt  38460
caccagctgt cagcaggttg ctggtacact tggggaaaac cctgctttcc agggcagtgg  38520
aaaagaagtg catctcgggc ccgatgtgcc tgtgcagtgc tgtgtcttcg agggctatcc  38580
tgtagtggaa attaacatgt gctattcttg gttcatgtga tggagaggag gctgcacagg  38640
tacctccttt cctttgccaa tttcaaagtt agctcaaaga ctagttattg ttatcttcag  38700
aaatcatatg gtccattagg tttcgggga ccagtccggt aataaattct gtagtgaatg  38760
gttaagattt ctgcttatag actctgtctt gtggcattgt ttgtgtctga attgacattg  38820
gtgatgacat cagggtttca atattcctct gatgacaatg acttagcaaa cacatgacct  38880
aacagcagag agtgggatca tggactctac aagttgctcc agtgtaggta tttagagaaa  38940
taaaggcagt tagactaagt gtccatatga atgactgaat gaacttattc ctgtctcttt  39000
aataatagaa catttaaaag ttttgtgctg agttattcat tatgaaatga catctctact  39060
gttagtttta gattccacaa aaggttgcat taaaggatag aatcctgctg actatacttg  39120
ttaaaggaat acatttatta tcttaaaaga ctttattttc ctgagtttaa cataaacaca  39180
gttaagaaaa cggatggatc aggcactaaa acttgctaca atcagaaccc agcagataat  39240
gctctggagt gaaatacctc aagaggcaca catttgcaca caagtgctca gagaactgaa  39300
atatctaaaa gcaaagcaca attatcatat ctccacctga gagtccttta gaccccttaa  39360
ccgaaggtac cttcatccat gccattaagg atctcgttca gttcgtcttc agtgtagtca  39420
cagaaatgct ctttccagct gtccccgttt tcacttcgca gaaccaccag ctccctctcc  39480
tttcctcgaa gggcagcaaa gtgaggaatc tccacgatca ccggcctgac acagcaatac  39540
agaacactca gtgtagacag gacaaccaat cctgagacaa gtacctcaac actgtctgtt  39600
gcaaagtgac ctggaattct gttcattctg gggacaggga cacagtgggc cttcctccag  39660
agcccaatga ctaatagatg gtgacacagt ggcactccac ctcaggggca ctggtcctca  39720
agtacatgct gctaccttaa ggcaaatgat atttctctgt gagtgcatgt ggcattctgg  39780
aacttctcct ttgataaatg taggtatagc aatttaacca aaagaaatgt acatgcatgg  39840
ctatgacgta tgccaatctc ctaaaacatg tcctacaggt gcaaaatgac aacatgagtt  39900
aagaaagaat atggctcata cattgcataa ttcaatgtgt tataaatgag atgtcagaaa  39960
ggtagactac ttgtgctaat gagccatgca cttatggcta ttctcatact gtcttcattc  40020
aagaaaacaa taggcatgtg tacacaatgt ggccctaatg agccactcag ctgacagtcc  40080
aatggtgtcc aatgcctatt atggtcagga tccagaacat gcactgtcct atggctttta  40140
ggtcacattc atcctcaaca tagacagagg cttttcattt ttgagtccag gttgctttga  40200
tacagactcc aaactcatca aaaccacatc atgactagca cagagtacaa ctaggcaagt  40260
ctcatgcttg aacgaaaatg aaggtcacag cactttaaag gagaagatat aaaacgtcac  40320
tcaaaaacaa aagtcacata ccacaagggt cagaaatggt ccactaaaga taggttatac  40380
agagtttaaa tcatagagag ggacatgtca tgggcacaat gacgaaaaga gaaatcatat  40440
cgcagaagaa ggagaagaat gggggccagc agccatcaat ttgttttaag tcgctcctac  40500
ccaaggaatt tggttccagg aggccccagc tgaaggatgc ggctgaccaa actttctccc  40560
tcattaagtg ggggaggagc cgttggcagg tgaagtttac tgagtacatc caaagcagca  40620
```

-continued

```
gtgaaagaaa gaacagaagt aagcttcagg taccgtgtcc acagaacccc agcatcacag  40680
ggtgaagttt ggtttcacac tgcgttcggt tctgccccct ccattggtca caaagagcaa  40740
ggaactagga actgagaccc agagtgtaca atggaggtgc ctctgtgcca ggccagcacc  40800
tggctgtcaa gtctgttcct atttaggttc actgccaggg cactagccaa aaatgaaaaa  40860
aaatggaggg gaaaaattgc tctttgggaa agacaaaact gttgggaata tagtaaaaac  40920
tctggacagc agccagacgt ttccatagat attcctcaac agatttgaag gttattaaaa  40980
aagcctacaa caatgtaagc aggagggagt taggctctga aatgaacatc aagaacatca  41040
aaataatcca gccatagtgt cattttatga tgcaacccag aactccatag gctctttcca  41100
aacctctgcc tgataagacg tgtaagaggt ggtttctaca actgggaact agcaacacat  41160
ccctttgaa tttggagcaa cctgttaaca atttgcccca aattacagac tttagaacat  41220
tttcagagtt ctaaagcaag aaatcttctc cccagtatga catgaacaac aatgtaaagg  41280
aatcctgatt agtaagagtt ttctctgttt taagacccaa gacttaaata caattgattt  41340
gtttcaaaat gatttgaaac ttgttccctg ctccaaagct tcatcccttt gtcaccattc  41400
agtcacgact tttcacctct tgacagattg aggtgccatt tagtatgaca gtagccatac  41460
agacaaacag aagaaagaag aaatgctatt ttctgctcaa aatggccaaa atgacaaatg  41520
gcagaggtta atctcagtat tttcatctta cactgtggct tagaagctga aggtaacaat  41580
tttgataata gaaaaacaca caaatcattt agactgaatt ttagatattc aatgaaggca  41640
gcactctggt ctgaagagaa ggtaactgtc actggattca taacgacaca aggcattaaa  41700
tttatgtttc aaacagaaca catttttct ttatatttg ccttttagtc tcagatgaga  41760
aacagaaata cttaccaatg gctaaaaaac atggttatac tattgggaat ctagcagcta  41820
ctcccacatc caagaagaaa aaacactaaa acactagcaa cctgcatgtt taactcactg  41880
acgccttatc atgggagtgt ggaagtaaag gcaggcatca aggcactatt tccaattaaa  41940
aaaaaaaaag tcacaggaac ctatcctttt tcaaaatggc tttgacatac ctttggtgtt  42000
ccatcccatt gatctcgggt agagggcaca agcccaccgg agagtaagta gacgacttat  42060
gggaaaccct tacccaagga actgagctcc agaaggtccc acttcaatga ggcggctggc  42120
caggccttct ccttccacca ttggcggcat cgttgccagt ctatggcgtt tcaccaggcg  42180
gcaggtgact cgagttggtg ctgtgcattt ccgaggtggg ataatgatcc ggagtccatt  42240
gtgtctgcat ccgcgcatgg cgccaccacg ggcatccacc atgaaactga ccaggaaact  42300
gaaaagtgaa agagaagatt aggcacgctt caaagcaacg cagcaggtaa tcacaaactg  42360
tgaggtcaat tgttttctgg actgtctatt tctcctcaat acaatgcttt taaatgtaag  42420
tgccttgcgg aaaaatattt ttgaagttta tactaatatc tatatttgta ttacttattt  42480
taatttctgt ataattttca tatgcttctg aagaataatt ccaagttttg ctagtaactg  42540
gaatgaaatt gcacagaaga tgggcaagcc ttctgtctcc ttatatgtcc tgtgcaatcc  42600
aagtgttcaa ataatataag gctgcagtac acaggaaaga caaagtgtca tatgtttcaa  42660
cttagctttc caagatcaca tctgtctagc ttgtttttaa gataatctca tcatgactga  42720
aaaacaacct caaggacctt ttcttatgat caaatctatg ccaatgtgtc ctgcccacaa  42780
atcattgttc ccagggtgca gatttgtcac cagtcaaaag acgggaaaac ggttggaata  42840
gactttctgg ctaaagtgat gactgcactt ttaacccgtc cctgcactca gccattgtaa  42900
ctgaaacaga gggtgaatga tgggaacaaa tggggttccc cctgctctgt ttctgtgggg  42960
cagggccagc atgggaagcc agggctcatg ctgatagagg tactttgaca gcatgatttc  43020
```

ccccaaattg caataaactg gaggtggaaa agaaattaca gtttaaatat gcaaaagcat 43080
ctctgtgagt tttgtttctt tattgttcac tgaccacgac aaaaagaatg gtaatctcaa 43140
gagtctgtgg ctgttgaatg tgccaagaga aagtgtctga actctgaagt ttctttgggg 43200
tcgtcacaaa tcctggagca gcttagctag aatgcttgtt actacattaa caatgacact 43260
caccaaggtc ccttggtcac gcacctccta cagaagcaaa agttaaataa caacagtgta 43320
gttgtcctgt acatatacac aaggacatgt gtaaacagaa tgtaggctct tccacaatca 43380
ctccaatgtt ctcccacttt cactgcactt gcaaagtttt tacaacaaca aaatggaagc 43440
aacgtatagg tgtttcatag atctactgat aaccacacca gccagatcaa cacacctaga 43500
tattgcctcc atgacaacac tgaaaacatt tgaaagggat tccatcaaag taagttgtgg 43560
gatagaaaca tggtacactg gtgttatttt ttgttttagg taagtgtaat atcatagcat 43620
cctctttgcg gcagaacaca gaatgcatta gacatgccat taaacagaaa acctgttgct 43680
agtaagagaa atgggtgcgg aggagcccag agtaccctct gaagcatatc atgcagcatg 43740
agaccacagg agccacagtc ctccacatgc agtagccagg ctagcctacc attctcccct 43800
cgctgttgag ttttcaggtc gggcaatagc tgctatgtac aagcaacagt tcatactgtg 43860
ttaactgttg atgttctggg tgttagcaaa acacaatgag aaaagggcta cagcttttca 43920
tactcagtct ttagtatgaa ttctgaaatg ttttgtttct gacttttaaa tatacacgtt 43980
cactcaaagg aagaactggg aatacttcca gatgaacaag catattttct tttattattt 44040
ttgagtacat ttatattgat gtccatttaa aagtaggaaa attgctgctg ctgtttcaac 44100
tagcagtgtt tccagattca ctgtaatatt tccaacttgt ttatagttaa atttgatacc 44160
tcctttgatt ttcctccctc ataacttttt aagataggat ctcaagtagt acagcctagc 44220
cttaaacttt ctacatttat gcaattaact ttgtactttg cctttacctc taaagttctg 44280
tggttataaa tgtataacaa cacctaggga atttttcaag tctctggtac tgtgagaaaa 44340
ggaaataggt gctaaaacta gaagggatta ttattacatg tttgcttaat gtaatgaacc 44400
ctcatagtat ctatgtcttt tgaagaaagt aacaaagttt ctgcactcac atcccaagcc 44460
cttatatttc catggtatta ttccagtgat ggcctttagc ttgtaggata ttaattctct 44520
acccccccca aaaaaaaaac acatagaata ttcttgtggt ctaccctcaa agcagagaat 44580
cggctgctat gtccttgaca gagtctatta ttttcccact gaagccctct tttttgtgtt 44640
aacttcctct gatttctgct tccatggtcc ttttgtgtga tctgttgccc taccacaaat 44700
gtcaggagct gtgccaagat gtcactttat gctttcttcc ttgcttggac ctgctaactt 44760
ctttagtcaa tgagatatca tctgtcatct catcaaggtg tcacctaagg gctctaacaa 44820
tagtgaatgc aatctcagtc ccctagtact cagtaaagta tggatgcagc gcactgtaca 44880
gagtcaaaat attttttgag taaatgaatg aatctaagaa tgaaaagcag gctatgacaa 44940
gttatgtgta cttacaagga tcagagagag agcaaggcat gagataagtg aattctttga 45000
tgcctggcca gttattacaa tcaaacctca ctcaaatccc tatgttctga tgtggcaaag 45060
caggaaaata gtatgtctaa ttttaaagag tctactccac acatttacgc tcagctggga 45120
gatccgatca gatctggtat acttgtttcc ctgggtagag gtttagtgga aatggaagac 45180
tctgaaaact aagagcttga atgtaacaaa atgatatttt taaaagtgat aacaagatta 45240
tatgaagaaa gactgaagaa ggaggaatca aagtagcaga atttaaagac tgaagcagca 45300
tatagataca cttcccagca atcattcctg tgtcgtgggt gattcagaaa acagtaaact 45360

```
ggtagaatta agcgcctaat atgcataatc caggggggaaa tggcaaactt caggagaggg  45420
taaacctcca taattaccgt aactgaagaa atgacatagg ctacatgaaa atcacaaata  45480
agagagagag agaaagagag agagagagag agagagagag agagagtaaa ataaaaagat  45540
gccaagaaac agaaagggct ggaagacacg aaacaactgt cattattcag aaggaacaaa  45600
tgccaagaaa aagaaagggc tggaagacac gaaacaactg tcattattca gaaggaacaa  45660
agagtattat tgtaaggtta acctagaagt taaacattct aggcaaattt gcctcataat  45720
gtaattgtca aatgaccaat taagactgaa cttcactgtg tactcccaga acctctcctc  45780
tacatagaaa gagtaagaga aacattgcct ggatttcata tctaggtcta cttgtaaagc  45840
cagcaagcta accagtcaat cccaatggtt tctagcacaa aactgggtaa gcatttggag  45900
atttttacta aaaatggaag aatacagaaa gatgcactac ctggatggct aagggaagcc  45960
agttcatctc tgctatgtat aaagcaactg ccaactctgc aagagccttt tctttgtaag  46020
gactgtgagg aaaggagaga gcatgggaga agtaactcat gcaatgctgg aatgtgtcag  46080
ctagcctgct ggaatgaact gagtgaatat aattctctca cctctgaggg acactggaag  46140
tgagacaatg cggtccctgc aaacatttac agatgaaggg aactgaagga aaccgaagaa  46200
gacagctaca tacaaaggag atgggatgca aactgaagct cagctctgca gtctggcgtg  46260
tgacatggaa gcttccttgt ccctgggtgc tgatcctgtc accacttaca gtaataggga  46320
gaaataaatg atgtgtgggt aaaaaaaaata cagattcaat aaatggctgc tcccattatc  46380
ttctttttct gccttttatc tttttaatgt catgttcatt aaaatgtaca tcatacatca  46440
cctaaaaaac ggtaaaaaaa atactcattg agagccttca atgtacccac atttgtgcta  46500
aggggtttta atataatcag tagagttatg attgcctcat gaaattgatt ctttaagcag  46560
gatgtgagga ttttcttact acagaacagg gtgctgtgct gccatgttct ttccatgtct  46620
gttttgaatt atttctgtaa ccacagtcaa gaaacatgac aagttcatta gcttttgttt  46680
tcatatgcat gaattcaaag atttaggtga ataaactctg aactcactgc ctaatattac  46740
aaatttgatg cagttatggc taactagatc agacaaccta cctgaatatt tgattttaga  46800
ttttctggag gaattcctaa ttggaaagca aactgttact gcttcaataa atgtagtttt  46860
taacccatgg ttaaatagat gctttcttga aaatgtgtag gcatactgcg ttagacattg  46920
acttaaaact acaagggagg gtggagagat aaccagggga cattggctct gatgcatctg  46980
actcttcaaa tgacagcagt catgcaaagt agaaattctg aagttttcta aattgtgaga  47040
tactatgttt tcacaattta aaaaggaata aaagcaaaca caattcactt ttattaggca  47100
gaggacttgc tgataaatat gcaatttgat tagctaaaca ggtacatgct tcagaggaga  47160
cagcataaaa caaggattct gacttttcaa acaactgtac tgtccatccc caaagttact  47220
gatacttaaa atttccattt aattcatcta ggaccatgag ctgggaacag ggaggagact  47280
gcagcattcg gagttagtca ctgggtgaaa gacagaagaa aagattcatc agggtgcttc  47340
agtgatgcca tgtacacagc agaggtcctg acttccactc ggactcgtgg tgctgttgga  47400
aaccacacca ggagcttcct tctccatcat tcccctgtcc tttactagtt ctccaaatcc  47460
cacaaaccaa aacattgatt aaaaaaatga cactgaaaag ggtggttcaa atttgttcaa  47520
atcactcagt aattaattac caatcactgt agtcatgaat agaaatacaa tatttagggt  47580
gtgcctgaga agacataaaa ggatgcttag acccttaaaa gaatgaaaac atagaattgt  47640
cttattttta gaggaataac ccatattatc atcatggatg accaaagaat aaaaatacta  47700
taatcagtag cccaaaggaa ctttaaaaat aacttcatct aaataataca gaatgattgc  47760
```

```
tatatttaga atgcagataa ctcattccgt agcacaattg caaaatatca aaaggttgaa  47820
cttaaaactg agttagcaaa gatatgtact attaataagc ccttagcctt tggctcacct  47880
agaatattgc aagataaaaa gcaaaacaaa gaagaaaaag gcctgagtgc taccaaaaat  47940
cacaaccttt aataaaactt caaaatagca ctgccaattt gcataattat gggaacataa  48000
tatttcagtt ggatgtagca cttttcctcc caaaagaagc tgagatgtta aggccatgat  48060
caagacagga gtctgtttta attttgatcc agctaacatg gtacctactg gtactaaata  48120
gacccacttt cccttcatag ggaaagtgag caattgtctt gatttggaga acataagcct  48180
ctgtatatgt ttcactagac atcatcaaca ctaaagcatc ctgaggtaga gcatatgcag  48240
aaggagatgg cgaaggagag gagaacaagg gacatggtca gagaaggaat tacgcagagg  48300
ttcacctgct gttgtcacga tcaagacatg gagaggcgcg gctgcaacag aatagataat  48360
ttagcatgga gaaagagtgg ataagtgaaa tataaagaat gaaatcagat gtgactttga  48420
ttaaaatatt taattcatat actaacacag tgttcactga aaaaaagaga tggaaataca  48480
agtaagatat cactctatgc aaatacaact aaaatgtcac tctgtatgcg ctgagagaag  48540
aacaagcttt ggggccttcg tagttcctcc cagtttagga acctggggaa gttacttaat  48600
tactggatat gaaagtgaag cattaattag cattggcttg tgggaacact tagcaaatac  48660
taagtgtcag agaagctagg aaacaccaag tgatattata atggcaaata caaagtctta  48720
gatactgtag atgtagtttt gattcaactg ctgtccattt gtaattcttc caatactttt  48780
taaataagat aattccccgt tgggatatag cagaagaaac acaaactgga aaggaatagc  48840
ttaaatgata gcttctgtgg cagagatagc atacagtcta caacaaagta ggtaacattc  48900
tttggataat agtggataat aaagatcttg gcaaacatga tcttagtgct tctccccaag  48960
acaccatggc ctactttgag cattgtggtc tttctcctca tccctaatgt ctagtcccac  49020
tttatagtcc tactcgtcac tgctcttttc cccatggagt ctgtgattca ttaaccccat  49080
gcctgcagga tttaataagg ttccaatgtt tgctaacatg tggaagtata ttttattcaa  49140
tgaatcagaa atccatcctt ccagatcagt tgatttgcta ctttagaaaa caatcttctt  49200
catctgaaag aaccagcctt tgtggatcta aaagaactcc caagatattt taagaaacat  49260
gaacagctaa attaaacact ggaagtgctt ccataagcgt ttacgttatg ctatcccatg  49320
caaaatacac ttggctgcct tatgcctcaa acagtctgtg atttgagcaa acagttttga  49380
atacatcttt catgactttt ttgaagtata gtgcaaggtt cacaacaaaa ttgtcttcag  49440
catgctttaa acgatcaatt tcataggcct ttattgtact gtatcatatt ctaacacctc  49500
atgagttggt atttaattaa taacatctgg ctgtcattaa aacactacaa agactttcaa  49560
agtggcaata tataaagttg agttgtaaaa ctagctattg gtagggaaac tgccttacat  49620
cagccaattc attatgcata taggcaatta caaagaattg taaagttcac atttttgtgc  49680
aacaataaag ttgcacaaac tttactatta tgacattaga tgggagcctc taataataac  49740
tgtttcttgg attcatgagg agtcagttgg gcaactcaaa taataacaaa aagtcaagcc  49800
tctcatttgt ccaaataact gaatgtatca atctgtgcag gaagcagagt gtaatcattg  49860
gcccagttct tcttagccaa ggacatctct taaaaatgaa atagagggaa agtaaataac  49920
tagcactgat tagtggtaga aaatgcagct cgaagttaag acaactactg aatttaatgc  49980
agcattgtcc tcatgtatac gttagatata atcacaagct ttcttcacta ttctttaccc  50040
aaaagtcagt cgcctttccc ttacatttta agtgggttaa aactcagatc cctgaaaaat  50100
```

```
atctaacagc tattacttat gaacctgatc catgatgagt ggattaataa ggaatcagtg  50160
ttataagaca tgatgaatgc tactcatata tattaatatg aatgtcactt tcaaacagca  50220
cagctcttgg aatccttaac tttctaaggg taatcttgct tctccctaaa gtcctctgtg  50280
gccccatgtt tgctcaacca ctacaatagt gacacccata gatgatagaa acaagtccat  50340
attgggattg tgggctgaat gtgtttgtat tgtcattcag aagacttggg gcgcactttg  50400
tttaacttat ttggagtttt gagaaatgtg aaatgtgtat aaggaggatg cagaaataat  50460
aaaagctata ttctattaag tacttgtttc taggtaaagt ctaatgattt taaaagcttt  50520
aactttaaag gagtgacaag caggttgtat ccactctgtg aaaggcattg aaaagacagc  50580
tgagaaaatg actacatgga tgtgaaatct ttttattcat atccctactt gagtttgagt  50640
ttatggatca gtgtgtgtgt gtgtgtgtgt gtgtgtgtgt gtgtgtgtgt gnnnnnnnnn  50700
nnnnnnnnnn nnnnnnnnnn nnnnnnnnnn nnnnnnnnnn nnnnnnnnnn nnnnnnnnnn  50760
nnnnnnnnnn nnnnnnnnnn nnnnnnnnnn nnnnnnnnnn nnnnnnnnnn nnnnnnnnnn  50820
nnnnnnnnnn nnnnnnnnnn nnnnnnnnnn nnnnnnnnnn nnnnnnnnnn nnnnnnnnnn  50880
nnnnnnnnnn nnnnnnnnnn nnnnnnnnnn nnnnnnnnnn nnnnnnnnnn nnnnnnnnnn  50940
nnnnnnnnnn nnnnnnnnnn nnnnnnnnnn nnnnnnnnnn nnnnnnnnnn nnnnnnnnnn  51000
nnnnnnnnnn nnnnnnnnnn nnnnnnnnnn nnnnnnnnnn nnnnnnnnnn nnnnnnnnnn  51060
nnnnnnnnnn nnnnnnnnnn nnnnnntcct tttctatatc taaaacctac acacaaagag  51120
catcagattt aatggaaaac acagcttcaa aattcaacta aaatacagtg agttctgaaa  51180
gagcacaaaa caagaggtgc tatgacagaa atttttgtct aaaaacacga tgaaattatc  51240
tcttctaatg cattccctcc tgaattatat tatgacagca aagtactttg aagagagccc  51300
ctgttcatcc atttccctat atcaaatcca tacatcagat ttaatggaaa acaagcttca  51360
aaactcaact aaaatacagt gagttctgaa agagcacaaa aacaagaggt gctatgacag  51420
aaatttttgt ctaaaaacac catgaaatta tctcttctat aattccctcc tgaattatat  51480
tatgacagca gagtactttg aagagagccc ctgttcatcc atttccctat atcaaatcca  51540
tcacgagcaa taaaattata cctaaaatta aaggttccaa agtaaactta aagccttttc  51600
tcatagctac tttaaatatt gcaacaaaat gtactttgca aggtaccatt catcatgtaa  51660
atatgcctgg gtcattttta tctcataatg gagatattag ttacacaaca caaatctttg  51720
tagaaaatct ccatagagga actatggctg aagaaagtat ggccaaaaaa agaaacagta  51780
tattatttag agggtagggg gcaatgctca gtgaaaaatc tagtgaacat ttgtcatatt  51840
gtagggcacc gtcaaatctc tcaccctaaa ttttttttt gttgttaaga ataaatttag  51900
gtttctgtca ttctctattt ctttctccct ctggactccc acccccacca ggtttcctcg  51960
ggatatttgt ggtatgagga catttgaaaa agttatccag aaagcagtca tgaaggcaga  52020
aagtcacata cctggtggcc aggaatcaca accgtgtcat caatcatggc actgtccctc  52080
aggtacgaag catggctcag agtgtgagac ctgtcagaac tgaaggaccg gaggctggta  52140
ggttggcagg aggtcatgat cataaaccaa cagcggtgga ggattgggaa gatgaaatga  52200
gccgagcagg agagtgaaaa aagcgtgcta ttagctaaca gtgcaacttc caggggacac  52260
aggtctcaga gtggccctac gcctccaccc aacagctaaa aacgcatcct cagactggct  52320
gaacagtgaa aggcaagggc acaagggaac ccacaaggta aatttgatac tcttaatctg  52380
atttgttgcc tttccagaaa tgtttgaaac cagcaactgt cttttatttg ccagcagaag  52440
aaatttatac aggtaataat tctgaaatcc ttgctaaata acctccctgc agccgtggga  52500
```

```
aaaaatatct gatggaagga agacagcggc cggagagcaa aagtagaacg aaaaggcagg  52560
tttcagtttt tgccctttat tttctattct cttcccatgc cccttcctct tcctttccac  52620
acggggaatg gctgaatgtc agtgtcctcc cctggaaggt acagagtgaa atgaactgga  52680
gccagatgtg tggttcctgt ggaagtggag ttcctcttgt ttatctctgg agagtccaac  52740
aatgctgtta tttcagagga gggcagtgtc ccttttgtat gccctgtgtg tagtgcagga  52800
agctctaaag agtgttggtt gccatgggga tgagaggcaa gagcagagga actcagcacc  52860
agcccaaaac agatacacac taacacaaag acaaactgcc aacagacacc aaaagtaaca  52920
ccttatattt ttgataaatc tgaattttgt tattcctaat tgcagattca aatgcaatgg  52980
gcaaaaattg cactcattct attcaatatg tacaatcaaa ggacattatt ttggtgttat  53040
ccctttttatt ttcctgagac agggtctttc tgtgtcatcc aggctagtct ggaactcact  53100
atgtagccca gaatgtcctt gaacacttgc ctcagtttcc tgagggctga agttacaggt  53160
ctgagctacc acgattagct tacagattga tatttgaaat aatgtgtcat atgaagattt  53220
ttatgcatag cccaggaatt aacagtttgc attcaaactg ccagccaaaa accacaaatg  53280
ggtaacacaa aggataagca agcctagtag atattgatca atgaagcact gtagaattat  53340
ggactgaatg aaatactaac attaagttta ttaaatagaa aattagcatg tagattagta  53400
gaaacacctt agtcttgaaa atgcatcaaa ttttgttact cacgctctct gataaacatg  53460
aggtgtcaat gaaaaccagc tatttgaaaa cattattaca tgaaggattc tttatggtga  53520
cattttccca tgttttgtca gtagtaggtt ttcagaacct cacatttaga cagtaagtga  53580
tacgacaaaa agaaattgat tattggctgt ataagctctt ccctacataa atctatatgt  53640
ttataatgaa ataaaatcaa aatataattt gaactcagct atctacagtt ttacaggctt  53700
ttggggtaga ttgagagtct taacacaggg cacaggtagc ctggatgcct tgcaattaat  53760
cagcagaagt ttgagcccta gcaagaggca gcaactgata ctacagctgg ctttgtggct  53820
gtggagttgg cttttgatgg ggtcttaatg agatcttgaa tttaggctga gacagaaatt  53880
caataataag gatgataatc ttttaatgta acaaaagtgt actcccacta gtggaataaa  53940
atgttgctat tccttgctgt aacccagagg aagcagagat acatttgagt gtgttttgta  54000
cccagcagca gtccaccagt agtacttaaa ttctattctt tattttgttt tgactttggc  54060
caaaggcaga gggccaacct cacgaaacaa cagtgtctac tccatcacct ttcccatcga  54120
gcgtcttcag ctgggcccag atttattagg tatataatgt ctagccatgg ttgtataatc  54180
taaatgttta gactataact tttcataata aagatgctag ctgtatgtga attcatactg  54240
caaaagatgt gaaccaggta agaagaacac ttgattcaaa aggccagctc ttttgctagg  54300
aaaaattaac cttttaatgc accctaagta gagaagaaat tctggtttaa aatgaaaatg  54360
tatactgatg ggaataaaca gtggtaataa aggtattcca cataaaacct gtgacaaagc  54420
tgtcagaatt gtattatacc taaactttga cagaaggcac tgggtctcag tgaccactgg  54480
agtgacaatg actaattggc aggtctgcct gaagagcatg atatgaaaaa gcttatgggc  54540
cctaagtgtc atatcccatc ccacagttag caccagtgat gaaggtgagt ttgtgattgc  54600
catcttcctg aatactgggt ctgtctctcg actgaattga tatagagaag gtagagagag  54660
aatctggtgg tttttattca ttttcatctt gcttaaacag ctaacaagga aaaaagacaa  54720
cttagccaca aaaggtgatt gcaaaagaga caatgggcaa gaccactatc tgagtgttca  54780
tttctttgag gatcctatgg tgctttctct gctgactgta gggaaatgct aactggatag  54840
```

-continued

```
tgaatcaaac tttatgtttc ctaactgttc ttttcaccct gagaaaatat tgctgagata  54900
ttctaacagc agagacataa ttctctctgg taaaataata acaagaaaaa acttttggaa  54960
taatttgagt ttctgagtca tgaactgtcc acatttggtg gaaaacatta cgaaaaagtt  55020
ctaatgtttt atagcagagt taccattaaa aaattatgtt ggggagcagg gactcctgtt  55080
cacttaatac acagagaata atatatccag agaaattaaa ttttacttgt tcagttgagg  55140
gattagcagc tatagataca aggaaagact caattcacac tttcctcctt tcatataatt  55200
tatgggtttg aataaatgta ataattaata tcttactaaa ctataaaatt tattagacat  55260
tcaacttata gagtttgaag ccctgttgaa caagtaaatg cacaaaatgt tcagtgtgct  55320
gaagaagctt ctgtgatttt ttggttactt ggggttttat atttgaattt ggacagtatt  55380
tttaacctgt aagcaataat aataataaat gaactaaaag ctagctgatt gtaatttgac  55440
tgtgtttttg ttcagtatgc attaatttgt acatgcttgt ttcaggcaac agaatatttt  55500
ctctagcttc tccaagtgca tatatacgta ggttgtttag tttgtatggg agaaaccatg  55560
cctctgtgtc ttcagccaca aggtggcact gtaacagtca gagttaagcc tggatctcct  55620
ggcactgtgg ttccagtaac agactaactc cagcagttac tgaatttaga tcaaagggga  55680
aaaaaatcca taattccaag atgtaagcaa ttctggccaa cacacacaca cacacatacg  55740
cacacatgga tgcacgtgca tacatacgca gtgagcagtg aagcagggaa atgcgtgtgt  55800
gtacaggaag gccatggttt catgccatgt aatacctacc tggggatggt actactgaca  55860
gcataccaaa taaagaaata atgaaaagga gaatggttac caaaaaaagt ggtgtgccaa  55920
attgctcaag caaaagtgaa atagtaatta ataaacatga aaatgagatg ctgtccatac  55980
tctgttttgg gctagtgtgt acatgtggtg gccaagagat gcaggtggaa ccctaaaaac  56040
atagcatgta atgtttgctt ctagcctcca tctttatatg ctggtaaatt tcaaaccatc  56100
cacctcctta ttctataaaa agtacactac cattctccaa tcttagtttg aaaaaaagga  56160
aatgtgactg aatcaggtat ttttttaata attagaaact gatgaaaatg aattgttcct  56220
tggttgaaca taatcaagtg cacactatcg tgaattcaca caaagctaca gagaagtttt  56280
tttattgtta aaacatagtc ttttaagaat ctcagattat aaatcgaaat ctgtcagtgg  56340
acaagaattt gatgtgtgga acacaggctc agtcaccttt ccccccaaac cccccacagg  56400
ctcctccttt cttacgctga ccctaagggt cacctactat ctaagccacc aatagcaggg  56460
agtcacctcc cttcgttttc aaatgctcca taaaactaac caacaaatct cactgcccgt  56520
ttcaaaattg tcactgctgg attctttcca cgactagccc agggttagag tttcatagtt  56580
gcataatcac ccagcaaaca gcactaagca gctgggtggt ctagtccagt gggcactaga  56640
atggtcctct gtagagggat tcttataaaa tccaggtaca gctccctccc ttcacactcc  56700
cactccagcc caaggcacca gtgtgccacc gataatgtaa gctttgctgc ccccacagtt  56760
aagtatccct gtcttcccta gcatcactgc tatgcattct tcctgtgttt gagcttctat  56820
ctgtcaggaa gatcaagcct cagccctgca gaggcgctct gtgctcttcc atcctggcct  56880
ttcagggtct ctcttaggcg gtgaattcag tgaacatatt ttaatcaggt tggtacctct  56940
gggacttacc agaatgcaca gctcaagaat taacttacca cagtaaaaaa aaaaaaaaga  57000
aagaaaaaag tgaagaaaaa ggcaagaggg gggaaaaaag agagaaggaa ttctggtgct  57060
taagggaaaa gcctccaagt agcttgcttt tgtatattat caatgtagaa ttgataattc  57120
cttaagctgt aaacatggga aattcataac atagccaaca aaagagtgag ctttgtccta  57180
tgagcatgtg actgttgatg ggaaagacat tacagcaaca tggacaggca tatatgtgac  57240
```

ccaggctggc agccatactt ctgaagaaat acccagaata ttcttattca tcttgctgtt 57300
gagagtacca agcaccaggt gtattagcta gtaatagcca agagtacctt gaatctcaca 57360
gtgcagaata tgagaaaggc tcttcacatt tgtctataaa tagtcaggtc cttatgggca 57420
cagatcacct cataagatcc tatcttcttt ttttaaatga aaacattaac tccagagcag 57480
tttccctctg cacttgtttt tctattattc ttcataattt tgttcacaca gaaataacag 57540
caccaatagt taagttagac ttaagggtat ctggagatgt taaacatatc ggccaggcaa 57600
aactgtgcgt agaatttccc tagagaacaa tgtggcagct gataaataca tcacttggga 57660
aggcagtgac tcctgtttgt ctttgtccag tttcgtagca gttggatgat tgtactatat 57720
tgtttggtgt ctctgaacta gtttccagtc cttcaaaatg ggcactactt aaaatatcag 57780
agaaatgaag gcgataacat gttaactggc aaatgtggta aactacccat aagtgttcta 57840
taaccatgtc tacatttttt aatctccata aaaaaggaag tggtcagcca ggcatagtgg 57900
tacatagtgt acctgcctat aatgcatgcc caacactcag gaagctagga ataggagggt 57960
caggagtttg agactcatct gagaaagcca ttctgggcta cacagtgaga ccttatctct 58020
aaaaaccaaa agaaaaagag aaaagaggga aacatttttt taaatgtgtt gtgagcactt 58080
gtgtctgaca ttcaatggaa ggttggtgaa tacctgtcag atctccctcc ctccaggctg 58140
taccgaaggt agttcatgcc atccaggaac tgactgctgg gtagtgagtc atcaccgagt 58200
tctttgagat cttcaggcct aaggtattcc cccccatcgc ctgtcattgt gtcatcacct 58260
taaggcaatc agaggagagt gaaggaagtt acttgttgaa tttcatacca gcaacaaaat 58320
atgcccataa ttatgaaggg cattcataca gcatcttgga taacagcaaa acactgcaca 58380
gcaggaagaa acagggttca tgcatatgtc tacaaagggc taaagctaat agagatagta 58440
tttgattcat tgccctacaa tgcaccaaga agaaacaatt ctctgaattg taattgtttg 58500
gctaccttga aagggttttc tttattatgt ctgtcatatg atgactagtt cagcttaaag 58560
attagccaaa tgtgtagact attagaattc tctcagtacc ttcaataatt ctgcacaaaa 58620
tccagtacta atagtctctt tgtgccattg acagtaggct aagaaacgta tatttttcta 58680
taataaatga gaggttttaa ttttatttat atattgtgta tgtgtgtgtt agtgtgtttg 58740
tgtgtatgta tctgtgtgtt tgtgtgcctc tgtgtgtgtg tgtgtgtgtg tacacatgaa 58800
aaggatatca gaggaacatg gtctctgctt ccattgtgtg agagctagga tttagttcag 58860
tttgtcaggc ttagcagaaa gcaatttacc tgctaaatca tgttgctggt cacaaatacg 58920
ataataatat tttataagat taaatatata caatagcaaa agagcacaaa agtaaaaata 58980
aattctaaga acaggactac taaaatcttg gcatgctctg gcttgggcat gagcctaatc 59040
tgttttagag agttttatta acatctggga agacagtctg tgacccattt tcatgtgtga 59100
aaagggtgat gggaatgtca aatgcaagat ctattacata acaagagctg catcttatgt 59160
atcactggag caagaagcca aacatcacct aacactcaaa agttggcttg catgcttcct 59220
ctttcccctc ttccctgacc ccactcagaa gttccaatac aagcgaactt ggcttaagtc 59280
cctactacta cccaaattgg ggcaccctgc atccacctgc tgggtcagtt agttttcaaa 59340
tgctaacctg tttctcctgt ttccagttct gatcccaagg tggtcacagg gaacaaagtt 59400
agactcaaaa taagtatcta ttacttatgc cttcaaattt ctcaatgctt cataataaaa 59460
cagggcccac attttagatt ttcttactca acctctttct tgttttgtct tggtgggaag 59520
cagaaggttc ataaaagtgg aaggaaaaga tagaggaggg aaggcagagt ctagctggaa 59580

-continued

```
aattccaccc tgacagacca gggcagtaag taaactacag atgatctggc agaacctggg  59640
aatgaacaca tttctaacct tcctctcttc tggtgatgga attgtgttac aaatagagaa  59700
caagctgtct ggacagtata tttaaaataa aatatatcct tttaaaaact ctagtgacag  59760
gccaaggcac tatttgaaac cctctgatca ctttaagctc atgaaatagt gtctgtcctt  59820
aatattctcc ccaattctct gccttctgat tgtgtgtgtg tgtgtgtgtg tgtgtgtgtg  59880
tgtgtgtgtg tgtgtgtgtg tgataccct gccactgttc tgttgtgata tgcctccagc  59940
agttgctatg ctcggttaat taaaagtgag gcttcagagt tttggataca cccatagtga  60000
gccttaggaa tagattgtga ctgtgaccca aagtccctag tgatagtcac actatctaga  60060
atctcatctg atactgttaa taggaggggt acttgtctct ggccaaatct tgatattata  60120
tgcaatttct ctccaaatat ttgcaccaaa aatactattg ttcagtatta cctatcaaca  60180
ctgagtggtg gaaagcgtgt atcaggagaa gtagagggag ttcatgcttg tttatctcca  60240
tttctagaac cctatgcccc ccatcttctt gtcagcctgg tctagaccct catctataat  60300
cttcctctgc caccaatctc atgaaggact ctccctccct ctagtaaaca ctaagcccta  60360
ttctacatca tacttggtct cctcttccct ttgtaatcaa actaattaaa gagacccttg  60420
ctattattaa ttgattttag taattaaaca gtgaccaaga gttgacttct ttgaaaaagc  60480
aatcttccat gatatctctg acagaaatct ctttgggccc ttttcctatt actttgagtg  60540
tttcttctca cgctctcttg tctgaaatgc cattcctaca tgacccctgt tatgtcccat  60600
ttgccatata ttattaaaat tcaaagactt catatactat atataaggtg ttcacaactg  60660
ggtccatctc agatcctggt caaactgcac atccatattt caatcccctc taagaatcct  60720
gcgcctgagt tttccgtaag catctcttcc ttgtctactt cacccccctat caacatgctt  60780
ctccacaaac tctctctatg gcgagtagtg cagctgtctc catgctttta gtgacggaga  60840
tgggagagat gagggtcttt cttatattta ctttatttat ttattctttg ggtgtgacta  60900
ttttgcctgt atccatgtgt gtgtacatat gtgcctgctg gatccggcca aagtaggttt  60960
agggatggtg gtgaaccacc atgtgggtac tgggaaccaa acccaggtct tctgtaagtg  61020
gttaagtgct gttaactgct gagccatttc tctagcccca gacagtctat tctgcataat  61080
ttagctatta cagaataatt gtacagtgac atactttcta ttattaacat atctgatgta  61140
gaagggtcaa acacaactag tttcctgcat catataacaa acttaatgtg agtttcctgt  61200
acttggaaca atgtcttcct aaattacaga tgtattcatt taataaaatg atgaatctca  61260
gattaatgag gtcacttttg ttgtattcta cagggttttt tttgtttgtt tttgtttttg  61320
ttttgttttt ttgagacagg gtttctctgt gtagctttgg agcctatcct ggcactcact  61380
ctggagacca ggctggcctc aaactcacag agatccacct gcctctgcct ctcgagtgct  61440
gggattaaag gcgtgtgcca ccaatgcccg gcatattcta cagtttttcc agacacattt  61500
tgggtagctc cttcccacta attgtcaggc atcagcatac tgtagttttg ttttttgttg  61560
ttgggttttt gttttggttt tgagatccgg tttctctgta taacaaccct gtcctggaac  61620
ttgctttgta aaccaggctg ctttcaaact catagagatc catctgcctc tacttcccaa  61680
gtgctggtat taaaggcatg tgccatcacc actgggctca tactgcagtg tttttttttt  61740
ttttttaca gtaagattga ttttagttac caacacagac attaaaaacc tggggataaa  61800
ttaaggctaa atggtgtgga ttaactatgg tgataacctc tgtaaagctc agataaagag  61860
actttctgaa atatcattga gcccttgccc tttctaccga aatatgggga gagctgcaat  61920
gagaaggagg ctaagtgctc acaaaagtga gcatgtaaga gatgaaactt gtttcccagt  61980
```

```
ttttcttctc aaccctctgc cattctgaag ttctcatgtt cgatagatca tgcagatcca  62040
gggcacttgt ggagatgcat acttgagctg ttcactaact gatggatgaa tctcaaagat  62100
aagccatttg cacttgccac cattctctgt gagtgctttc tctactctca gatacatgag  62160
ttcttccagt tcccaataaa acaccctctt tctgtggacc acaactggat taatattcaa  62220
aaaagcagat ttttttaatc attaactgaa acctttatga tattccaatt tctctagact  62280
cagctaaaaa ttcagaccct tcgaaactaa acccaaagtt gttatgcaac agaataactg  62340
aattattttt ccactcatta tcactctgct gcactttcct acattaagat ccctgtattg  62400
atctttctct acttcttaaa acctggtaca ccctctgatt aatctctcgc tttttggaaa  62460
atacataaga ttgtgtggat ggccccgatt ctagatatga acactgatgg tattgtacct  62520
tcactttcag ctcttcatgc attactttcc atgtatgaag gcagaccctg tgtttgcctt  62580
taattccccc ataatgtgaa ttatagaact cttcttatta tgacagcaca ttcaccagct  62640
gtgctttgga ttcaagggag gataacacca atggctttag cacatatcaa gttagttgga  62700
gcaggcatct aaacccatct tatgaatacc ctttggtatt tgtacatggt taccaccagt  62760
agattctata gagaatgggg atgggctaac accttctaaa catatgtgac tgcactatgt  62820
ccatgtggat gatagcaggt tccacgaaaa catttactga acaaaatgtt aaagagttag  62880
cacggtaggt caactaatgc tgtactgacc ctttgcataa aaagcttttt tcacaattca  62940
aatatatcat ttatataaaa atcactgtac ttgaattctc tgctggtaat agaaagttgt  63000
tatattttg gctattagta aaactaaaac attattctta tcacaaagtg ctcttattca  63060
ataatcaata ttcctatcaa atcaagagtt cttttttaac cactggcaaa tgtcactgtt  63120
tagcaatttt gattttaaaa gttatatatc tacatctcat tttatatatt aggcagacat  63180
gagagtctta caaatgaagt ttctagaaat tctacagtaa acactttagt tgcattaggt  63240
aataagtcct ttaccaatta ttttaaaaat agtgatctgt tttgaaatca aatgcatcta  63300
atttataaac tgagttttca tgtaataagc ttgctatgaa gagataccac atcatctctg  63360
gaaactgcat atcacataga atgttttatg tcattcattc attgtcccct aaacaccaaa  63420
ttcacactga atgactttta aaaatatgta ttttgttttt atttgtgtgt gtgtaagtgt  63480
gtgcgtgtgt gtgagtgtgt gctctgtgtg tgtgtgtgtg tgtgtgtgtg tgtgtgtgtg  63540
tgtaagtgtg tgtaagtgta tatagttgcc cacagagacc agaagacagc ataagatcca  63600
ctggagctgg agttataggt gtttgtgagc tgcctttcat gagtgccggg aacacttaaa  63660
cactggacaa tattctccca ccagccatcc cctcactaaa tgctatttaa agatcattct  63720
taatcataat aacttacctc tactcttgac tatcttttaa aaaatcaatc acattataac  63780
tcctaattat atatttgttt ttaagagagg gtttcaatgc attgctaagg ctgacttttt  63840
tttaaaagac agattctctc cacatagcat agccctagct gtcctggaac tcactactta  63900
gatcaggttc gccttgaact cacagagagc tacctgcctc tgccacctgt gtattgggac  63960
taaaggtatg tgccaccata cccagcccag gctcacttta atgtctcctc tcaagttaac  64020
atcctgcttc tgtctcctga gtaatcataa ctaaaggtac atgctaacat acctggcttc  64080
taagtgaata tatctttgcc tcatcttaga agggtaatgt gagcattcac ctcaagcagt  64140
cttgactgaa ggtatagact ggaactaata aattagtaac caatatgcca tgcttacttt  64200
aatgttaact tatcaaagaa ttacttttcc tcaaaatctc tatcctaaaa aacaaagata  64260
tttatctgga aaaatattct tataatgttg gtctccataa tagttgctaa attattacca  64320
```

```
gaataagcaa attgtggctt taaacttaca agttaataaa atgcacacat caaatgcaca  64380
catgcataat tctacctata ttacacaagc tgtttcaaaa gaaacattag tatcaagcac  64440
aaagatttaa ggattaatgg gttgcttcta tgtagttaag aaaaatgaaa agcaaagaaa  64500
agcaatcact ctgagtccct taaatggtac ctgaatcact aagcgtttcc ccatcaataa  64560
agtggtcacc aaactgctta agagctgcac aacatatgaa tgaaaatgaa aaataaaatc  64620
ccaccgaaat atggtgtgca tataagtatg ctcaaactca gctggcagaa cacagctcag  64680
acttataata attactcaga attacagcat ttggcaatac ttttaaaata actcatcatc  64740
atacattgat ccaacatttg ttcattcttg tcataattct tatgcagact gacagagctc  64800
agtgcctatt gccaataaca aaacaaactg gttccaaata agactgaaga atgtaaagct  64860
ttgtcttgag attgcatgcc aaaaaaccta aaaacatatt taatcatttc tatagagact  64920
attactatca ggcccagcag cacctttgtg gcaatgattt tgtaaagata tgactgaatt  64980
ttccttgtac atatatatgg caataaattt ttaaatctca catgctggtt ttgctattga  65040
agcttgtata ctgtgtgtgg cacttctgtg atcttagggt agtagttttt gttgttttgt  65100
tttgttttta ctcaggagaa acaatgcagg gaaattaaaa atatggaaca aagaaaagtc  65160
actggggagg ttaaaaaaaa aaaaaaagga aactttctgt ctcaagatgg cttcttacct  65220
ctacccctag gagagcctag cacatttttt tagaaattct ttttcaggac tttgcaatcc  65280
actgtttaaa tgagcagttc tcaacttttg ggttacaact cctttatcag tcacatatca  65340
gaaatactgc ttatcacata tttacactat aattcataac agtagcaaaa ttactgttgt  65400
aaagtagcaa taaattaatt ttagggttga ggatcaccac agcatgaaga actggactac  65460
agggtcatag cattaggaag gttgaggact accagactag ataatgttcc tcaactctaa  65520
aaccatcgtc aaagtgctga tctttcctgg cattaagaat gatttattgt gttaggactg  65580
tactattttg tgctgaggtt ctttaatgaa ttttccaaga cttttttttt ctgggtttga  65640
tatatatatg tattctgtac acttgaacta atcagacaac agagatttct taatatacct  65700
ctaatgaaga atgtttaaaa gcctttcaag gcatttgaat atgaaatgta ttggtatata  65760
attaatatat atatatatat atatatatat atatatatat atacatttct tagtcttact  65820
agttattaga gattaaagat aacaatgggg aaaactaggt agacctgact tgcctacttc  65880
ttcaatggca ggaataaata ctgtacacta caattggtga ctgagcttta aatattagga  65940
tgctgtcatc tatactacca cctttagccc taagaaaact ttggtttcct tgtggaagaa  66000
cttgacagct gtcacaaaga ctgcagaaac tattacttac cctcttcatc agaaacatca  66060
agcacctccg tcatcgtttc aggaacattt agcttgtgtt tttccgtgat agtctggaaa  66120
aacaaaaagc attcattgca aagttaaaaa taaaatcaaa caaaacatga atgaagttac  66180
agaggtgcca atctacctta gcagcaagtt atgggacctc aaccatccca tcttatccat  66240
gcggaagctt tagaaactta ctctttcgtg aaatcccctt tgttctttct gaagataaaa  66300
gaccaatgaa cattgtacaa gagaaaattc attacagtta gttcccattt gaaaaatgaa  66360
gtttctggta atggcatgag taattagtca tattgaaaaa gtaaactaat gtcttcaaga  66420
cgtctttaac atgaactaag tgatgtttcc agaaaaaaaa aaaaaaaaac tttacaatga  66480
agtaattctc tcgcaatgta ctaaaaacaa agccaataaa aagatgctgt aaataatata  66540
ggtcacataa attatatgtg atatgttttg tcatgggtta gaggaccaga agtagagagt  66600
tagtcatctt tataatattc acagtctaca gttatggttt actgcttatt ggccttctcc  66660
agtgctccca aggggcaaaa tccaatgatt tcattcctga tagagtaaaa aggatgagag  66720
```

```
accaggctca tctggctgct tggcttataa ttctagactc atcttagctg caaggcctca 66780
gcaagtcctt gaacctagct atgcttcagt ttccttgttg aaacaccaca aactaatgtt 66840
tcataaaatt gttagggata ttaatacgag agctctgaga acagtccttg gaataggata 66900
ggactcagta agtttcggct ggaataactg atggtcgtaa ttgaaaatta cgttcatctt 66960
aggaaggagg ggcctcagga cttttttgaa tcacttgtac agaatggaac agcatgataa 67020
ttataccccca aatacaccac ggtgattttc aaaatgaaaa aaagtcagac acagagagac 67080
aaatatcata cgatttcact aatctgtgaa attgtttaaa agtccaaatc atacaaacag 67140
acagcaaaag catggttact agtggctgag ccaggcgagg gggaaatggt ctggttctca 67200
atggatacaa aatgtcagtc aaagggggaa gaagtgcaat aaatacatgg caccgtgatg 67260
atcacacaat atggcaggag attgtgcact tgaaactttc ttttctctgt tgtttttaag 67320
acagtgtcat ggaccccagg ctcatctcaa actcaaactt gctgtgcgca tggacagccc 67380
tgtacttcag cccttctgtc atcacctccc aagtgcctgg attccagctg tgcaccacca 67440
tagcttgttt aagaggtact ggaggttgag cccagggccc tgtgcatgct aagaaaggtc 67500
tgtattaact gacctgcacc cctagcccca gtatatttga cattttctag caaaagttag 67560
gtattctcat cacatccact cacaaatgaa aagtgcatga cgtggcggtg aattaattag 67620
ttcacttagc tatgttcaca atgtgtatgc atctcaaatc accacgctgc ccaccataaa 67680
tatgtaccat tgtatcaatt taaaaaatga aacacatgta caaataaaga aacctcatag 67740
ctttaaacat tacctaaagc tgattgagtt tcaaatttat aactctaatt cctacattta 67800
aagtgtattt agtgttccag ttggcagttg tgggaacatt aaaagactaa acttttgaca 67860
taagaggtaa atcttcaact agaataccaa agcaccatga gtaggttgtc cagagtgctg 67920
cgctttgctt tacagataat aaagacttat ttcaatgagt gcaatgacta tcacagactc 67980
tttcacaaag cagaagagat tttccacagg ttgccatata ccaagtagct ataaatggat 68040
ataatagatt tgtgctaaga gcaactagac tgattcagtc agagcatgga aatgcacaag 68100
tctttaacca acacttcttt agtggacttg ctttgcttat tttcagaaca aaattaaata 68160
aagtggctca gaagacctat tgtgaggtag caaacatgga caggcctgaa ggccttattg 68220
tcaggtccct gctaacctca tgctgggtgg tttgtttcaa tgtcacatgg gccctgcctc 68280
ttatgctgtg gagattttct acatagtcct atctctatca aaaacttttc tttggactat 68340
cagatgtgct ttccacagag aaatacttcc tgatgttcca acaataaatt tatttattta 68400
actgttgcat atattgcata caactctgta tggatcatct atttctctac ctcccacaga 68460
ggggtggagg ctgctgttcc agaggtagag tgttaccaca gaacctgaag aagagtaggt 68520
gcctcccaca tatatgccca atttacacag ggcatcgtta aatgcataac aaacagatct 68580
tcctactcac aaaggatgta attagataaa atacacaatt ctcttttaaa atgaaagaac 68640
attaagatat taggttacta aaacattttt tgaacaacta catttgaaca atatgtggag 68700
aactaagcta taattcaaag tgcatgctct tctctttctg ctgtagaatc taagatgtca 68760
tggtcaagat cagaaactac tttaaaagtt aaaataagga atatgcacac gattaatggg 68820
atataattaa gtcagacaat gagttattca tcatgatatg ggaaagcata gaaaattaaa 68880
tataagcttt tatcatgatg ttttagaaag agtggataat atctggtttt ccctgtatgt 68940
gggggactgt gtgcttaact gaccccactt agtcacacac accccagcca attgctccct 69000
ttattcacac acttcccaag ccatcatagc acagccaaat gatcttggcc atcctatcac 69060
```

```
ctttcaacac cctcaccctt tggtcaccag ggcagttgca ggctactctt gttttgtgtt  69120
tgttttttaa tgtccatcat atttgtcaat ataactttca tgactagata aatctttaaa  69180
tgtgtaattg tttttttttc ctgtaaaaac aaaggtaagt acccggaagt ttcaacaaag  69240
atatgtcccc ctcacacaca acatatatgg ctacccaatt aagcgtgagt gagacaatta  69300
taaatgattt gaaaaactat atatcagaaa aatttaaggg ttctgtactc catatgtttc  69360
tttaagaaaa cacacagaat gcatcaatgt tatatgaaac ttctttaaaa gtttgtttac  69420
aatgtgttag gaatgtttgc tttcgtgtac atatttacac tccatgcatg cctggagcct  69480
atgtaggcaa aaagagggtt tcagatccac tagaactggg actataggta attatgaatt  69540
gccatgtggg tagcaagtac taaccactag gctatctctt cagcccccagt aaggtttaac  69600
taggtgttat aaagcacatg cacacacagt gaatattgat ggtgcttgtt ccaagatgac  69660
aatttagcca tctgatcaca gaactatatt cacagaaaga aatgatggcc agacagtgtc  69720
aaatgaaatt atctgtattc attgcatttt catgttgatg attcctttaa cagacatggt  69780
atcaaatcaa atttaggact tagaatttac atttcccttt atgacttaaa aaaaaaacct  69840
tcctaatgag taaaggatag tatatctaaa atgatttgtg tatggtaatt ctgggtaatt  69900
tattaagtaa tttatgttct tcttagcaat gattatttgc tacataatac attacattat  69960
aattacacca ataataagaa attagctgat gacagcagat tgacaggtag aagaatgaat  70020
catttttcaa agtttgtcca atcttaggag agtagagcta taggctctta ctgttgggaa  70080
taagccccca gttctgtgat gtcgctctgg taagcacaga gacttcatct aagacaatgc  70140
tgaactgtct cgcctccctt gctgcatctc tcagtgtaaa attaggaaag ccaaggttaa  70200
ggaaacaagg catgatccca cagtgtgtgg gcaatctcag ctgcaccagc ctctctctcc  70260
cttactatct agatctgctc cttcacaatg ccttcattca cgctttgggg taaagaactt  70320
gggaaagaag tttcttttct tcaagagaac tcacgtggtt gcacaagtgg cacaccctgt  70380
aaatgcaatg atgggaaatg aatccctcac ttgtgtagct agaactcaaa gctgcgttta  70440
atggtaaact tcctcaggtg acatttattc cctttgcctc attataaaat gccttgctct  70500
gcttgctatc accatagcac tggcttttat ttgtttgttt tttgtttgtt tgttttggtt  70560
aatcagtaaa ctttagaaaa tgacattaaa taggacatac ccactgaaat caataaagta  70620
tactttcttg tgtggtattt tttgttgaaa cctaggcagg agtcattctt tcacaaaatt  70680
ctggttaagc tacttttcag caaagccaag attaattaca ttggtatggt taggaaagtg  70740
ggctttgcca tccagcagtt taaactgaat tccagatttg tcctccagag ccaacacttt  70800
actaagctta catatgaatt atttgagata tcacaaatag taccctatgg agaaaagaaa  70860
acatggggaa aaggaatgat tgaacatcac ttcccaaagg gaagcatact acatgaagac  70920
ttccatgctg aaagagaatg cagccatact ttttatcccc aaattccatg tctcaaaaca  70980
aactcacaac tctatgagga gccaattagg agaaccagaa aataaagata aagcagaatc  71040
aaaacatgta gccattgaga tagagaaatg gtccagtggt taagagcact ggctgctctt  71100
ccagagggtc tgggtccaat tcccagcacc cacgtaatgg acaactgtct gtaactccag  71160
ttccagggga tctgatgccc tttgtgagca cccagcatag acacatgcaa gcaaaatata  71220
aacaaaacaa caacaacccc tgacaccact atcactatcc ttgtggataa aggggattgt  71280
ggagggtggt ggtttattta ctgtgaatgt catactctag ctgaaatctg acattctatg  71340
tgttatttat ggcttatcag tttttcacct agaaatttga attctaaata tggtgattta  71400
tttttcaaat aatgttctgc tttaaaatga acataaataa caacatagca atgaataaat  71460
```

```
tataatgaaa tataaataat taaaaaaaca aagactcaca aaatgttctg aaacagttgt  71520
tctgtattag agctgtcagg gataagatct tccataccct acctgtatat ctggtttctg  71580
acaagtctct gcaatcttac ttaaagatgg caaataggat atttaaaaat ctctctctct  71640
ctctctctct ctctctctct ctgtgtgtgt gtgtgtgtgt gtgtgtgtgt gtgtgtgtgt  71700
ttcacctgtg tgaatgcaca acatacacag caagacatat gtgtgaaggt tggggaagag  71760
cctagggttg tcactctttc caccttgctt tgagatagca tcttattttt gctgctggga  71820
agtccatgct agctggccct ccagcttccg ggaattttcc tgctgccacc tccgatctta  71880
ccacaggatg accacaattg caaatgtgca gggttactgt cacgtggttc tgggggtcca  71940
aacttaggtt ctcacacttg ccttgcaaat atgttagccc ctaagccatt tccaagtcta  72000
gtaattagaa tgtttagaaa caaattaaga agtgctagtt gcctcggttt taaaatacag  72060
atctttgtgt ttaaaatcat ttgctctaat ccatatttat gcactggaag tcttagaaat  72120
gagatatgga agtttcacag tgctattgat gtacaaaaac agaatgagat ttcctgtggg  72180
ccgtaactct cttctcccgt accgatacgc ttatgcagaa gagctgtttg gaccagtgat  72240
gctctttggc atgtagcaca gaggcctcac acacctttcc ttcagtaaaa atgaacaaga  72300
ggaaagtagg gccaggagag gaaaggatcc acaagcatgc catctagtgg caattctata  72360
aaagtacaga tccatggttc ccagtgtgga aaaagtatta aagttaacaa aacccaagac  72420
agacaacaca caggctcaga gtcaatcttg tcactaaaac ctttgtttct ttgtgatgta  72480
catgctattc tgaggtggca tagctgtgta ggtcttcaca ctaaaacttt tcctgttaaa  72540
acaaaaatcc cactattttt tttaaagatt cagtcataca gaaagatttt caatattctg  72600
accacaggga aatgaaggtt tgaagggata gacacattta tcttcatttg agtaacatat  72660
aatggaaata tatgccatca aatctcaaga cattgcagac acatgggcac ttttcatgaa  72720
ttgattaaaa atatttaaat aaaatatagt tttacttttt cttttaaaaa aaggtcatga  72780
ccttatataa tgacctgtaa atagggtggt aaactttgac aagacctttt ctcatatata  72840
atttatcaaa tctatacttt atatctttaa atctactgtg tgtgctggct aaagaggatg  72900
gctctgctta gaaaaggagc tgtgcagctg gctcccatcg aaaagtgcag tcgatattgt  72960
gcagctcatt aattattcat actccactct atttaaaact gcatgtcaca tcaactgcac  73020
cccgtctacc tcaatggctg tcaacgggga ctttccacta gcccatgaaa caaaattcct  73080
ttcctttcga tcccctctat tgaaagaatc aagtgttccc aaatactgca tgtagcagtt  73140
ctagcttggg agaattcacc agaacctatc ttatttcgtg tactttattc gttggtttgt  73200
ggttttattg tttccataga acatctcagg ttttgttgtt tctctgcttt ataaagataa  73260
attttaaaag ccattgttcg gagaactcgt gcttaaatta aagtttaaag actcctccct  73320
ggagcctctg cagagattag aaagcctctg tcagagtttg ctcttgggac ctcctctggc  73380
aaagaccaat aactatcact ggtctctcct caagaataag caggcatttc aaagcagtag  73440
aaataaagga ctttaggcat acactgaaca cctgcgattt tctttttatt ctacaaaatc  73500
atcaaacata agaagggaaa gaaaatttta ggatgctctg ctgtctatag aagtgcattt  73560
gacttagcca ggggctcttt tgacaagctg cctggcctct aggccaagtt caggttggct  73620
gcagaatgtg gtacctttct gccagcagta ggtgtcacac acagctagag gacagaggca  73680
ggggagccag aaaagaaact cacaaggaaa aggtactttt ctatagctag aaggctgcat  73740
tcgtatattt tatttgggaa ttatactgag ttaaagacag aaaccctgtt tccattggta  73800
```

-continued

```
aacacattcg tagctgcata ttcctgagtc tgttctacaa tgcattcagc aaaagaagtt  73860
cacggaagct gcaaacactg agcgaaaagt atgtggcggg aaaaccaaga ggacaggagc  73920
aggtcagtca tcagtactca ccgtggtggt ggtggtgacc tcctccgtca caaccttcag  73980
ggtgtcaacc acagagatgt agcccagccg cttagcaatc gccaaggctg tgttaccatt  74040
ctgaagagag agaaagaagg aaagagtgag aaaggctagg gaggactgcc ttgcgagcca  74100
atgagctcac ccggggctcg gcatgagcca gcacttcctt ccaaaacaag gcacagctcg  74160
ggaaaatcac tagtttttac cattacatct aaatctgtct ttgtaacttc tttagactat  74220
agcccaggtc accatggtaa cacaacaagc ttgcatctgc ctgctctttt gaataagcac  74280
ttgatgcttt aaccctgagg ttgtcaagca gctccaaatg ctgccccagc cttctaaagc  74340
cacctctgga actgaggact ggtgtctgcc aaaactacta gggagaacct gctacattct  74400
ttgctcacca agggtcaggc catctgccgc aggtaaaatg ttaccatagg gacccagtga  74460
cagatttagc ttctgctctg caggagctcc agtactgcaa gaactacaca agccagcaat  74520
tccagccgcc tccagcccag gccactgggg accccgtttg tttaattaca ccgcttagtt  74580
tacatttcaa tggctccatg tcccaatgag gcagttctaa gccaacactc agaaaccggc  74640
tcccttaaga agacagggag ggaagggtga atatgcgctc acatctgaga gccagctgta  74700
agcaaagccc ttccagcagc ccaagtggag ggccccactc cccagagacc caactgactt  74760
ccttcccggc aagcactccc cagaaatcac agacttctag aaaggttttt ccagaaatct  74820
ggggctttcc actgtctggg agtttgttta aggaggatgt atcacacttc atctctgaca  74880
acaaacagga cagcagggca agtacaggga agggccacag gcctccttac cgcagtggtg  74940
gcatttggct tggccccgtg ctggagcagg acattaatga tgtgtgtgtg gccctgttgg  75000
gcagcttggt gcaaaggtgt gtagccattc tgtggatcat gatagcaccg atttgcagag  75060
ggaggagaaa attaggttag ccttcaactt tagttcactt gtcttagtta cagcaaaccc  75120
atcaagcacc tcattgttta tttggagcac aattttccca gcaacccatt tctcagcaac  75180
aaacactccc tcacacctta tggcggacta aacaaggaga gactagatta tgaaacaata  75240
aaataaacag actcaattta taactgttat tatattttaa ccaattgaca tttaaaatgt  75300
ttaaacggag agaagattaa aaatggaaaa gagacagagc tgtgatccat ttccttagga  75360
aagatgaagg gtaagttggt gtttaactga aggctgccga gggtcacagg ccactattag  75420
tcatgaccat cttaacaacc cttgaagcta gctttagatg atctataaag atgaaagaga  75480
atctcatcta tatttaatct catgcttaac tcaggagatg gctttggttc tagaaggctg  75540
tatgtgtaaa ctttagaata gcaaactaaa ttggaagttc aatgccctgc cccaagaaaa  75600
tgtgtcttta aaaactagaa ttttgacagt gtgatcaaaa ctttcatgga gaagaatgcc  75660
cctgacttgg gaggaattgc tgttaggatt agtttgaggc cagtcttgtg cagaactgta  75720
gtcaacaggg gtggcactaa ttagttacgt attcatatta actcaaaact tctactggaa  75780
cccttgacgg tggaacggga gtcattccct aagcattcat tctgtactgg atgctggacc  75840
ttagagtgtt gtctctttca attttcattg tcactcagaa atggcttaca gtgcctagtc  75900
taaaaagggt attttgtaaa taatacttga ctaaatgaat agtaaacaaa tgattcataa  75960
atgactattt ttctccccat ttcagaaatg atgccactga aaataacagg gttaacctat  76020
ttctccacaa tcactctagg tttagtttct atgcagaaga tcatggaaac cagtggctac  76080
ttcacaactg tctgcaaaaa aaaatattta tctctatcag agcccactgc atctagctgt  76140
aacttctggg tagtatatat gtatatatat catgattaaa agaatatgca tattattaaa  76200
```

```
gtgtgtacat ttcatgcagt gtcagagtag atgcatgacc aacaagcata tttggtcatt  76260
ttgactacaa aattgtctga ttatattcgt gagtgtcata agaccccttc tagacagtca  76320
caacggcctt tctgtgtatg ggaatgacat catgtatgga tatctttctg tccaggtgtt  76380
cctgactctg tcatgttagg agtctgacag ctgctataga ttctctacaa taaaataaat  76440
ctgatgccct gaaaatgcag tcgatttaaa aagactctta gaaacctata gttattataa  76500
gaccctgcct gctctcaaat caggcaatcc atagacattt aagaaggata aactaaatga  76560
tatttatttt cctaaaaatt cttcctttcc attttattta taataaaatt taccttactt  76620
ctttattatc actcaagcat tcactaacta tgctatgtgc taaatacttt agtatataaa  76680
taacattctg tacactaaac taatatatat taatatagtt taaaagataa attacctaca  76740
aaaatcatgc caaatataat tagtcatagt taattaaaag tctgacccca ctgtagacca  76800
tattaaatcg agctctcatg gactgacccc ctatggtctg gaaaatgacc ccaggtatga  76860
tttaatctaa catttacctg aagttgtgat gagtgagaat agtcaacaga agattgagca  76920
gggctataac tttacattga cattggcttg aggtttctgt gactttccag ctggctggca  76980
caccagcctc aatctacccc ttctactatg gatgagcaag gctccaaatc cctcacattt  77040
ccatttctct cattgtaaaa cagagatggc tgaaggtgta tgcttcaaga aggaccaaat  77100
acgttttcca tgaagatatg tatagttcat gtgtagctca tgttaattat gtgaaaatac  77160
tagcaagatg ccatttcatc gtagacaatc tgcacctttc attgtgtcta atcaaagaaa  77220
tttctatttt gtatagagtt taaatccttt tcacaagtcg attccctgta ggtccagttt  77280
gtttcaatct aatacgacag ggtttcacta taattctaaa caaaaaaaaa tgatttcatt  77340
ttttaaagtt tacatttctt aatttttatg tcaagtttta tgagtagcta aggagtagag  77400
gcgggacaca tgtttgcatt ctaaaagcag ttaaacaatt ctttagtaac catggttaca  77460
cataaaacat caggaagtaa ataataattc cttctgcaaa ggaaaaactc tgaagaactt  77520
actaacagat tgcctattaa gacatgcatc tgccttctgc cctgaaatat atggtcccaa  77580
aggtcacatt aaaattatat agttcaccta aaagaaatcc ctaaaatgtg gaaatgagat  77640
tctgtttttc ttgtaacaaa atgtacagat ctaattccac agaagcacaa acaacacaat  77700
acagtgttgg gcatctaagt gttaagacca tctcagtggg caaacactca ctgataccac  77760
gtaaaccttt gcttgtactg ccagtgtctc attgcatggt gcatttgtac atctcagttg  77820
gtcgtgacta tgtgtatgag ctggctcaac caaaagagtg ctaggaacta aataaaggtt  77880
gaggagccac agggaagctc ttccgtaagc accaaatgaa agtgtctcag aattgtgtag  77940
gtcagaaaat acacaacagc catcgtaggg caagctcaca agtttgaatc ttaagtgcta  78000
taatactatt gatagatcac aaaacaagtg tgtttcatat tatctttttg aacatgcttt  78060
tgcacaaaac tgatatcgtt tctgcttttt ggaaaacaga aaaagaaaca tttacaaaaa  78120
atcttgtaat catttctaat tagtgtcatc ttgaaatgat ggctctgaaa cccctgaatg  78180
tgcttgcgct gatgcatctg agctgtggca ggtcttcctg atgtgtgaac tcaaatacac  78240
taagcccaca attctttgta acagtgaaga gcaccagttc caccatgctt ttctcttgga  78300
cttggatcaa tctgtgtgct ctgagatggg tggtgatatt cagacctgct ttgtctaata  78360
ggacctttga ccttctttgt gcagaactgt tagggacgtg ccacctctga gttatccctg  78420
cggaactaca actcagtcat ttcacacttt tgttgataag cattaccact tgaggttccc  78480
aaagagatag tttatttaaa atgggatata tacagtgtgg gctgtgcaag tctgtttttc  78540
```

```
cagaggagga gatgtggagc tgggggacag ggccaagggc ctaaaacaca atagaggaag  78600
tctggcaggg cttcaggatg aactctgagg atcaactgtt tcctgcaata aattgctaag  78660
ccaaatctgt tttaacttta taacacatgc aattctgaag ctgacctcca tggccatcaa  78720
aggttatcag agtggaaagc cctaaacaat cagaaaacta cactgcttct tcaaagttag  78780
ttcagaagaa ctagaaagca aaattaaact taacccaaaa gcaacttgca gctacagtag  78840
tgtcctgact gtacccttgg caggataagt ttgattgtca agaaggaaaa tgagtatata  78900
ttttaccttg gtttttgcat tgacatttgc tccctgcttc agaagaaagt tgaccatttt  78960
cacattccca tagtgacagg ccacgattaa aggagtgtaa ccaagctgca acgacagatc  79020
ccaaagtaca agtgttatac ggctagtagt taatcaacaa aggtaaggtt tcaattattg  79080
cacatggcat ctttgggatg caaatatagg acaagcagtc cctaaccacg cagaacttta  79140
catcagcaag ggagataaga cacacaggtg acttaactta gctaaaagaa ctgagaattg  79200
caaaatgata ggacatgtca atgggaagga gaagactcta gtagaagcag gtgggatgag  79260
tgaaatgtgg aaggaagaag ggaaggatag gaagatgtgc agtaaagaga tgacatacac  79320
attggccatg atagacacat tgcactcata aactcactga ggctgcttaa gtggcacaaa  79380
acttgcacaa gattgggccc atcaatattt tatctgaacg agagagggag cccatgaggc  79440
tccgtccctc ccagaggggc tattagcaat taacacctgt ttggggagca atgtcactgt  79500
cttcagtagt gtagctatag aaaaactgcc ctcactccat ggaatgactt cccacctagg  79560
ttcagattag taaatctagt taaacccatt cgcccttaca taaaaagaag gcaggcaagc  79620
tggagggtgg gggagaggca tgttgagaag ggcgctggtg ggagagggaa gggatgagcc  79680
cgggaatgaa ggagcaaaaa caactcatta tataagtaat aagtgacact aaaacaatag  79740
caaaaagaat ggataagaaa acaatagcac agagagaacc aatccccctc aagatgatca  79800
aggacagagc cagaacagtg aggcagatgt aggagctaaa gcagaagtca gagggtgggc  79860
aacaacctgt agaactagag tcttagactg agtccagagg ccactttctc aactccagtc  79920
tgattctagc agacacgggg aagcatgcgg tttatacttg agaatgaact tttaagaaga  79980
gagtcctcgg gcatgagctg acctgaatga ggccaaccaa gaatcagcca aaccagaact  80040
ggtgacaaca ccgtcaagag atctgctgta cctttgtgta ggcatcctgg tcagccccgt  80100
gtttggtgag aatgtcagca acgttcactt tatcttcttg ggctgcaagg tgtaaggatg  80160
tgagcccact ctgtagcaag aatggaagca agggaacaca tcagagaggg aaacacacgg  80220
tcatctacag gatcgtgttt tgaagagtcg gaatgcatat ggcatctctc cagacatccc  80280
atcttctcac atttcagata aatccttgga gtaaacatga gttttcaacc aagatatagt  80340
ctctgcagaa aattatgttt tctgtatctg gtatttatga tttcagcttt taaaatagtt  80400
ttgttaataa ctttccagat aatattcatt tcaagcctac ctacacttcc tcatgactct  80460
acttatttac ttcaattaac agactaaaca aatattgctg caactttata accctggcaa  80520
taatcaatat tttcatcaat aaagtatcat attaatgttt aaaatacatt gagttactgg  80580
aagtaagctc agaatatttt ttccagcact cagtttactt tgcggggagg cggggagggt  80640
ttgtcttcca gatggtaaat tttttaaagt aaccctgtca cttatatagc actgtaaaac  80700
ttggccaatt ttatggggaa aaaagtttat gcactgggta tcaagtaata aatgtgttta  80760
tttgaataca tggcaaaggt acagtcatag attaataaaa aattaaggaa tagagagggg  80820
agaagctgtt tatccaacca atgccacacc ctaccagcct taatatatat aagtagctcc  80880
ctcaagaaaa actgagattt aagggtatca aatataattt tagcaggcaa tttttgagtg  80940
```

```
cttttgttat actaggaaga actcacatga tttggacata gctatgaacc aatttcctgc  81000
ctatgtacag ttcatagtct agcttagaat atatccatcc tatatcttac actcctccaa  81060
ataacactcc aatatcctta ctgttttccc tcttctacta ttttaggtat tggtgattga  81120
acttagggcc ttaggcaaag cacacaaata cttcactatt gactcgcaac cccagttctc  81180
tttttacctt ttattactaa ggggcccaga ctaatcatag acccatttaa tagctcaagc  81240
tggttttgag tttatgagtc tcctgattca gccagcctct cagtagctgg aaatacaagc  81300
ctatgccatc aaatctagca atgttgctac tttgctcaag gtcaggtagc atcctggcta  81360
actggccagc cctattgatc atggctggaa ggctcgtttc ccccccatta gcattgaggt  81420
cgagaaaact gaacatggcc ttcaagcccc attgcttcca gcatggcact ataccaagaa  81480
aataacagcc attctgacca ttgaaaacat ggggtggcac atatatagag aaaaacattc  81540
tatgactctt caggggggctt tcccttgagg gcttcgtgct ccttactcgt tgagtaatct  81600
cagatcagct gtgaacctgt gagtcaaaac aatgactagc ttgactagaa aggcccataa  81660
agcatcagcc tgagaaagaa atctgttttt gaattaaaat tctgtcattt ataaacaaat  81720
attatttaat cctacaacat aagaatctta atattaagac aaagcagagg atacatcctc  81780
aagttgaaat ttttttcttg tgatttcttg agagagagtc tctagcccaa gctggcctaa  81840
aagtcgggat cctccacaac tgaataattt tcttcatgac tgggtatgca agtcaaaaat  81900
ctctttaaag atctgctaag gagctgctta cactcttcaa aagcaaatag taatgcactg  81960
gaaaggacac catcaaggag aacagagtta atctgctcta tgttttgaaa attaaaagac  82020
atgctctcag aaacattgtg tgattagttt cacgtactgt ctagaatgtt tctctttgag  82080
ctgttggtca gagctgacct gaagacaccc taaacaatag agggtattta tcttgattga  82140
tcatcagaac ttggtggtaa gacactagca atcactgaaa acactacaca ttttggtcac  82200
agaacatgag aaaatcaagt tgctactggc caggaagcct ctcccagttt tggtaattac  82260
tgggagtgct atgcaggctg ctagaggagg gagaagtcat caaaaatctc agccagctgt  82320
aaagctgtga gccacaataa tgactggctt gactagaaat gcccataggt ataatagagg  82380
cacaagtgtt atggaggtca ccaatttctt tataactgga ttgaaagctc actccatagg  82440
ataaaacatg tatggttggt gttgaaaatc ctgctaagaa cctgtggctg agtggggtta  82500
actcataggt ccgaggagtg aatctattac tattatgttg ctaaatgggc acgatatcaa  82560
atttctacct atattataaa tgccactttc tgacctcacc agagaagttt ctttatgaaa  82620
taaatagtgg ttaacataga aaatcataac tgattaaagt gcagagatta attatctgtg  82680
gattgctcag ctataaacag gacattgata ttatccccat caccaagact ggggaccatc  82740
atggaagaag ggacaaaaag agtgttaaga gccagagatt ggacaggagc agagtaaaac  82800
aatgtcctct ggagatgaca gttctgttgc tctcgtgaac tgacagtagc tatggttgcc  82860
agcacaagac ctacacaaga tgtagccagc caacattcta gcatggaatg agaagagggg  82920
ctcatgagcc cctacctagt tagatatgga cagtttatag cttctgggtg tatttgagtc  82980
agatttcttt tctgtgtatg ctcactggta ggtcaactgt caccaatgga tggtgccaaa  83040
cctacaagac tctgggcaac acaaattgga cctcatgagt taattttttt ttttaagaag  83100
acaagagatt aagaggagtt ggaagatgga gaaataatgg gagaagaatg atgggtgaat  83160
gtgaccaaaa taaattgtat ggtattctca aaatattaat aaaatattac atataaaaat  83220
attttaatct gctcaagatg gcacttaatg tttaaaaata agtttctcct gattgttttc  83280
```

```
aaatgaatgt gcttttaggc aaacagtaaa tagatgtatg cccccctcctt tataaactga  83340
tattaaataa tatattttgt atctgagtgt caggatttcc ccacctattc aaatgattgc  83400
ctaaaaggtg ggcttcaaat gtgcatcaaa ccctccctac tgtctgggtg atattagttt  83460
tcattattat gtttttatgt tcattctttt aaaatgcaaa tctgggaaga ctattgcagc  83520
tccacgttgt ggcttaagca tatctgccaa attttcaagg caacactaaa tcttcaaatg  83580
ctacttgaag ttgggatcac tgggtagact tagaatactg ggagtccatg aggatgaagc  83640
acccatcttt catttgtgat gctctcccac tgcatcctta tgtaacaaaa aaccctcacc  83700
agatgtcaaa atgtgctcat gttatcctgt tggacttctc aacctctgga atcataagtc  83760
attttgaaac tcttatcttt ataaagttcc caatcttaag ttacttgtca tagcaagaga  83820
ctaaaacatt acactgtatg aaaggatctg ggaggagttt caacacaaag atgaggaatg  83880
caatgggaca cttctgagtg ataaagacag ggaccagagt tctaggtaca cgtgagacaa  83940
tctacctgaa tcacagttct tctaaagagt gcatattata tactccagtt aatgttagta  84000
agcaaattga tattccaaaa gtacaggtta atttactagt cacacattga aagcacagta  84060
tttttggaaa atcccaagaa gcttaatttt tatcttgccc aatcacgtgg tcaagagatt  84120
caaatggtca gttaataggc acagcctgta actttcagtt tctcagcagg tggctccagg  84180
ttgataagta agcaaatctg tagtaggcat acactttcat gtttgaatga ttttaccctt  84240
atattgttga ctactatatt ttaattaata tggtcatcta cagaggctat ttactgggag  84300
gggaagctta aattactgtg tggctttctc taaaagggat ttctaactag agtcactacc  84360
taaggtaggc tgaaggtggc ttaaaaatct gtatttcagt aagttctcag accacaatgc  84420
agagataaac gctgtcgttt ggcttgggtg gtagatacgg acctgctagc tcatattccc  84480
ctgtgaagcc caacctccag ttggaaccac tcttttgtct gtctctgtcc ctggctccct  84540
agccactttc ttactgcaat ttgcaattac aagcagcaga aactagggca ctgtggctgc  84600
tgaagagcag atcttaactc ccatgggcta gcttcttgag atgcccacac catgctgaga  84660
agctgagagt gcagggcagc acaaattgat aatggaactg gcttaagaag aaaagtgaag  84720
acccacaatg gggggttaagg aaggcaaagc tgtgggagca attgccatcc atcccctagt  84780
ttctagctga gcttcccttc cttctgtctt ggcatttttg acacagccct gcttcctttg  84840
cacacacaca cacacacaca cacacacaca cacacacaca cnnnnnnnnn nnnnnnnnat  84900
acacacgcac acatacatgc atgccatttt tgttccaaac aatcttcgct tggtttttg  84960
tttgaatttc tccaatacac tcgactgaag ccagagtcta taacacaata ccttggttga  85020
catgtggata ttggctcctt tttccagaag caaggtgacc atatctgtgt gcccctcttg  85080
tgaggccaga tgcagtggag tgacccccttg cttcgtcaca gtgttagtct cagctccata  85140
gttgagtagt gtggaagcta tttgcatctg attcttcttg gcagcaatgt gtaaaggagt  85200
ataaccattc tacaacagaa ataaaaatat ggatatgaca caagcgcaca cacacacaca  85260
cacacacaca cacacacaca tcacacacac atcacacaca cacatcacac acatagagaa  85320
cacctgttaa gtgctcacat atttatctcc aatggaaata ataaagtata atcaggcaga  85380
aaagataaat gtaagctgac agacagttaa ttcaaactct tagttatgaa atgtttctat  85440
ctaaccttag catctttgca agcaaatgaa aaatatcctc atcacactct agaacagaca  85500
caggcataaa aacatcaagt ctgaaagtcc cttcatcact agcttctctg ccaaacaaga  85560
aaagaaagta cggcggactc ctcttcatgt gatagtcctt gagaacctgg tggtagattt  85620
catctctgtc taatgatttc tctaggtctt ctctcttcca ggctaagcat ccattccttc  85680
```

```
agttattcct gaccctttgg tcatttctag tcctctctcg ccaaaagaca acctgctctg  85740
agctgattat gatctgttca taatgctctg gaatcgtgtg atttcacacc acagaattct  85800
atacatcaga tattacttta cccacacaga atcaaattga gtaacttcta tggtattttt  85860
ataacacttg tactcaaatg gttctaacta gagtattctc tccactccct gaacaaatgc  85920
tgttgaagtc ctagaataag ccaagttctg tgataggtaa aggtgggaac acaaagggag  85980
gtaagatttg tgttgttagg aatctaatgt aacattatta ttttccaatc atgataaata  86040
ttttaaaata tgatcttaaa tatgtttata aatgagttac tgaaatacac aacatctgtg  86100
tatattttca acataaaaac ctattcataa acagtataca ctaaaataac ctgtttatgg  86160
gtaacctggc ttggtaggag ctgtgtttga atataggtaa aagatataca ccaagaaggg  86220
attggtagtc aagagaccca cttaaaagta ttcacaactc agttgaccca gatgaacact  86280
taaaaagcaa agagacagga gagtcctttt aggggcagtg tgaaaatttt gatgttagaa  86340
ggaacgaggg tatgaaagtt atgttttata ggcaagaagg agaaacctac aacacctttg  86400
tcaagttaca cttctcagta tctaaaacac tgactgctag gaataagatt aatctccaca  86460
agctcatatg cactcgcaat tggtaattcc cagctccaaa aattgcagaa aggtttaaga  86520
caaagcaatt ggtagaaata gtttttaaaa gtcacaaaaa attattacta tatcaggaag  86580
ttatctaaaa gcaaggacca tgtgtactca gattacagct acatggcacc tgggaatcct  86640
aggctgtagt cctcaccttg gcagtggcat gaggggaagc acccttctcc agcagcagca  86700
gcgccacctt ctggttgtca taatgagcag caacatggag cggggtaagg ccattctgta  86760
aaggtggtgt ttaaatctca gcattagtac attattagcg ttagctgctc tgaaactatc  86820
aggatgcatg gacggcgcta tcaattaatt acaatgttaa ttaattaatg tggccaatgg  86880
aaagaagaaa aacagataca tgataatctt catatcagaa acaactaaga ttggaaatgt  86940
tggcgctgaa aattagcaaa cggaagcttt ctgatcacga caagcaaaag ttaagtttct  87000
gtatacgtca caaaaattct tcctgataca gagcagctgt gagccctcta ggataagatt  87060
tcatattaga ggcactgaaa ataatggttc taaattgcag ggtacagcca cagtcagggt  87120
catatacgtg tgtatttggt gtacttttgc ctggatcatt catcttcatt tcttatgagt  87180
gataaaaaca gtcaacagtc ggatggtaaa aacatactac agaaacctct taccttccct  87240
gctgagtctg cagctgcacg gcgctgcaag agaagttttg ccacatccat gcttccgtac  87300
ttggctgcta cgtgcagggg agtgaaaccc ttctatagtt tgacaaagaa atgtgacaat  87360
taggttgttt ttatttttta acttcagttc cttaaataaa aatttgttat aatccattaa  87420
gctaacacta ttggttctcc atttgtgaaa actgatggca tgatatctgt taatcatgaa  87480
tcagtaaaaa ggtaaggaat gcaatttaac cagaactggt aggacctttg ctaggcttga  87540
tggagtgaac aacaacaaat gtatttggag tcttagagac tgaaacttga tatgaacgga  87600
ttttagattc ataatatcca gtggtgttgg tatactgttc tgattcgtga atggaaaacg  87660
aagtaccaaa aagctcatct ttcatcttgt ctctaaaact aacacaacca agtgaacagc  87720
tgccttcaat ttcttacagt cccttttata gtatttttca tttcaaattt atttaaatta  87780
tagagtattt aaaaagcttg agttaaaata attatttgaa ttatttagca tattttctgc  87840
aaaactggcc agatagatga tatatatata tatatatata tatatatata tatactccta  87900
aaaatatcct tttaacactc agaaatttgt ccccatgctg tccagtcaca tgtgtctcca  87960
gtcacatcta tcatccttgt gtgccagcgg ctgactaata ctagatagtt aacaacactg  88020
```

```
aagcttcaac aatgtgcttt tagaagatgc ctatcccagt ctggacaaac atccagggag  88080
cctacatgag accattctag accctctgca tacatgtcac agttgtgtag cttgatctat  88140
ttgtgggact cctagcagtg ggaccacagg ctgtccctaa cactttggct gacttttggg  88200
aaccaatttc tcatgcttgg ttgccttgcc caaccttaat acaagaggag gagcttagtc  88260
ctaccaaaac ctgttaaatc atgctttatt gatacccatg agagatcttc ccctttccaa  88320
acagtaacag aggagaaatg tattgttagg gtgcagaggg gaggtgggga gggacttgga  88380
ggagaggaga gaggggaaaa tgcagttgaa atgtaaaata aatgaataca tttaattaat  88440
aataaaaaga tgcctgccct atatattttg tacggaaaca ctcactgtcc catgagccta  88500
accaacagca gttcaatgag cagaatgcta taaatagagt ctcagtcctg gtggcactat  88560
gatgtcaacc catcctccag gacagatgct tcagccacat gcttttctgg aacaatagtg  88620
ggagttggag aattctaaca ctgaccagga tctagaaaat caaccaagca attacttctg  88680
ctctgagaac tatttaagtc cctgtactgg ctgtctgtgt gtcagtgtga cacagctaga  88740
gtcatcagag aagaaagagc atccgttgaa gaaatgtctc catgagatcc agctataaag  88800
cattttctca attcgtgact gatatgagag agcccagtcg ctctcatatc cctgggctgg  88860
tggtcctggg gtctataaga gaccaggctg agaaagccag taagcagcac tccttcatgg  88920
cttctgtatc agctcctacg tccagggtcc tgcccagttt gagttcctgt cctgacttct  88980
ttcactaatg aacatcaata tggaagtgta agccaaagaa acccttgcct ccccaacttg  89040
ctttttggtc atggtgtttt gtccacagca atagaaaccc taactaagtc cccatcaaaa  89100
tcatcatcca gtgattcaaa tattcatctc cgaagaacca atactgccct ttcatagagt  89160
cacaagacaa attattttta attaaggttg cattttttttc tttcttttag aaaagaaaga  89220
aaatttggtt ttagtagttc ttggaaaaga gtgaatcttc tggccttttc ccgtgtggca  89280
caaacgtagg atgtaggatg attaaatcta aagctagcat ccatccacag aaattcaact  89340
gctgttgagg gtcttctctc tgttttccat gcacagaagg gttggatggt gctagcttgg  89400
gatgaagtag atttctctga cacaacatta tatggaggaa gaaaagcaaa ccccttatcc  89460
ttacaatgca gctgaagttg tgcccaccct ttatacagtt ggaaaccctt attagacaaa  89520
actgcatagt attttcactt cagaatgaca gggatagagg gcatctctcg agtcacaggg  89580
ccacttcttg cagtgttaat ctcatcagtc ataatctccc tctggtacct ctggtattta  89640
taaacactta aagttacaat gatgagtcac ccagcatcca gccagccttg ctcactaaac  89700
cattctgttt aacaagtgct tctattttat taccctattg aactgattat tttttcaatc  89760
ctaaaaatcc ttgaaaggca aaaggttatt ttctattcct ttacttgtac atgtattaat  89820
tctattcctc atccacaaaa atggctgtta aatttcttgg gttaccatta tcactgtata  89880
tttgttcctc ggcatctaag ctctgatttt tttctttttg aagaattttg aaaattcatt  89940
caccttttca gatgtcttca tttggaaaat tatcaatttc catgtcagaa cattttaaaa  90000
gatacattat tattttatgt ataagagtgt gtgccccact gggcagtggt ggcacacacc  90060
tttaatccta gcactcggga ggcagagaca gggggatctc tgtgagtttg agaccagcct  90120
ggtctacaag agctagttcc aggacagcct acgaagccac agagaaacct tgtctcaaaa  90180
tccacccccc caaaaaaagg agtgtgtgcc tgaacgtatg agtgtgtacc acatggtgct  90240
tcggaggcca gtagaaggtg tcaaaatccc tggaactgga gttagagatg gctgtacatt  90300
tctttgtggt tgccaggtcc tctgtaagag caacaggtgc tcttaactgc tgagctctct  90360
ctccagccca tgtcagaaca tctttggcag ccatgttcca gtaggcttgt gctgatggta  90420
```

```
actcgtgggc aaatctcact tctgagggct caggggccaa actattcact acttcattac  90480
acacttacta acttcttccc acccaggcat actatttact cctacttatt gaaagtcacc  90540
tgaaatggca ttttaattca tcgaactgct attgcacata tggaaagtac attgccctgg  90600
gacaagctca tgtatcctag gactctattt gccttgtttt tctgttcttc tgcactagct  90660
cagtctaatt tgctctagct ctttgggtgt gttcatgctt caatgtaact cgtctccacg  90720
tagtgaattt cttgtggaat atatccacga gaaggaaaag cagccctgca ccaccacagg  90780
atcttgagta caggataaga tattactctt ttattttgtg tgtgtgtgtt atataactca  90840
tgaactgatg tgcaaacctg ttctgtctag acactgcaaa taactgggag gaaagtaaag  90900
ctggtaaagg ttagtgtggt ggtttgaata agtggccccc attggatcag gcacctaaac  90960
acttggtccc cgctggtggc actctttgtg gtagctatgg aacctgtaat aggtacagtc  91020
ttgctggagg aagtatatca ttggagaaag cagatgaatg ttgacagcct tgccttactt  91080
ccctactttc tctccttcct ggtgtgctgg taaaatgtgc tcacccaggt ctcttctttg  91140
accacccatt gccacaccat ctctcccatt ataaacatct accctctgga accataagcc  91200
aaaataaact cactcttata taagatgctt ttggttatag tattttatgt tagcaacaaa  91260
aaagtaactg atacagttgg acactacaaa ggaaatgaga tagcaaatga gaagtgacgg  91320
agctagcact aggaaaggca ggatggagca aagggagctg ccactcaact ctgtcaccca  91380
gcattgccag tctaacacag tattttctac tttatcagtg atgccagttc aacatattag  91440
agaatctccc tccccacttt tttattcctc tagagaatat attttacagt aaaaaaagaa  91500
attaagagtg gcctttgctt cgtggtaata caatcatgac cattacattt cttgatgcct  91560
ataccagaag gaactagcac tttaattaga agatgggatg caagactcct tgaagatgct  91620
acaaaaaatt ttgcaatccc ttcccatcat tttgatcata atctagacta cttgagaaag  91680
aaacaagtca gaggtctgac agagattgtt cccttcctgg aactcttctg cagttgagca  91740
aagccttaac ttggcacttg cattctctta accgctcacc ccccttacc ttggtcgcta  91800
aggagtgtgc tgctcctgct tccaagagga cagaggccac atctacctgt ccttcccgag  91860
cagagatgtg cagtggtgtg tacccatttg tagtggctgc atctggatga gccatatgtt  91920
gtagaagcag ctggacaatc tctgtcttac ccagtcggga ggcaatatgt aaaggtgtct  91980
gttcctccta caactcaagg caagagatca gttaggtccc agcaaacccg atcttgcagg  92040
aatgtgtact tctcaaatac ttcatgatac cttctttgaa tctctaggaa tctctactca  92100
aaaacaaaaa tggttactac ccctgtcatg gtttatttgt atttgttata gaagtgatcc  92160
atttggtcac aaaatctccc ttaaattttt aaacagattt tatttattgc tttgtttata  92220
tgtatgagtg tcaacatgta tggaagggaa acatgcatgt gcagttcctt tggaagtcag  92280
aagaggcatc agatcccctg gatttggagt tacaggcacc aatgagtcac ttagttggtg  92340
tggaagccaa accccgtctt ctataagggc accatcgagt actcttaact acttagcccc  92400
tcccttagat ttttaagtag aaaatacatt cataaacttg gtcattgttt gatgaacaac  92460
caaaaaacat ctcttaatcc ttaagtcttc aaccctctct tgtgcttact tattggtgaa  92520
ctcacggttt tcaaggagaa agaaattcag tccagaaatc ctaagaccta gattcttctc  92580
caagagcttt tacggagagg caggatttat tctgggaacc gaatcaagag aaaagaccca  92640
aggaaactgg aaaatgctat tcctacttca ctcctgagcc aaggacacaa atgctggtca  92700
atttgttctg ggagaacttc ggataaagac tacattgtaa tatgatttaa agagagattg  92760
```

```
ttccaggaag ccctgcagat gggcctgtga tgcacatcta ggacttcaaa gatgaaatag  92820
aactctggca aaatgaaaat gaagtgaact ctctgccaag tgttttttgc tctaaaaaca  92880
gagaggatgg aactgagtag aaggggcagg aagaacaaca cattcagcaa ggctcagaag  92940
accacctgac tctaacgtgt ggtcacaaat aatgttctca gggttaaaag aactaggaag  93000
aaccactgtc tcttataaaa ataaaattga gagtaccctt aggaatgcaa aagagtgtat  93060
ctttataaac ttccccaggg taagtcatca taaaagcacg gaaggaaaag ctgggcaagc  93120
tgccagtgat aagaatgaaa agagaaaaaa atatactaaa tctgtccaaa taaatacaat  93180
actttaacat tatgtttttt taaaaaaaat tgtaggaaga gaagaagtag catcacatga  93240
atttcaaaaa gaaagtggtt aataagcaaa agcaacacaa ttattttacc aatagaattc  93300
aagttctata aaaatctata acttatacat tttttcatgc atgatatatt tatgacttgt  93360
ctgacttgtc ctggtaaaca acaaaagaaa gcataaactg tattattcag caattttttc  93420
cagataaagt gaacaagaat gtaatgaggt ctcaaaaact gttcaaggtc attaagctat  93480
taaaacagac actaaaggta gatacaataa gatggccaag aaggaaatga tcaggacaag  93540
gtgagcagga atgagcacaa gagtaaatgg ggagcaaagc aatcagcatc aagtcaggac  93600
ccttcaagag cctcacacta tctgcatctt ggttctccca tagacctctg ctggcagagc  93660
ccaaaggagg tgggtacaga aagccacaca ctgaaatatc aactatgaac tttttaaatt  93720
gttggttttc ttttatgtat atggggaaat tgtgaatttt aaagaggagg gggagattgg  93780
gggcaatggt aatctttgga gctcttatca actgaccatc tctaactggc agtaattcct  93840
gggttaggga tactggttaa tgaaccagta gttaaactac agttccctgg tcctcagacc  93900
ctaaagagat aagggcttgt ctgttcactt gttcgtctgt ttaaataaaa gttaataacg  93960
ttttacccaa ttttaatcat tttgctttat ttccatccaa aagtggaaaa gaaaataata  94020
taattttgct attataaaat tccttcagta tttacacagg tatgtaaggt cttttcatgt  94080
ctgagcaatt atttctttgt tgaaatggaa agtttgtatc tgctacccca ggataaagtt  94140
aaccgaaatc aaggcaaaga attgggaaag tgcagaagac tcatgagagt ggacaacatc  94200
atggaggagc tctggtcccc tgaccttgtc ctagaaggcc ttctcatgaa gcacaagcga  94260
ctgtgtcaca gcccagacag gaagtgaagg tctctgcttc actactgtct actttgctcc  94320
taggcagcca aaattaggga gacttgctga accccagctt ttacaaaaag acagaaagaa  94380
tagcagttgg accaaagttt aaaatgtgga tgtgattcct gctaataatg ctctccaaaa  94440
ccatgtttac tggcagctga gcaaaataag ttaagtttca aatcagatta agcctaagga  94500
tcctgccatt gctcaaacct aaaagcaaag ataaggccca caatggtacc aacagaacaa  94560
tccacagtgc agtgcacaag cattccagat ccaggggttt gaatgtagtt cttggtcacc  94620
tatctccgca agctttaggc ttggctttcc tggacagaga aatgagcaga accagatgct  94680
aaagtcacag cagcagtcct agccatggtg tttagaagtt taaaggctca tgcagtcaaa  94740
atagacaaaa agataggcag taaaagaggt ccagatggaa aaaaaaaaaa aacctctaaa  94800
taggttacag tgtgtttaaa ggtatccata gccttaagaa agaaaataaa aagagtatag  94860
acaattatag aaaaaagttt aaaatgacaa cataaatata taaaaatgaa taagccatgt  94920
agagatggga aatacacagg gagtctggat cctatacagc attgtgttga ttttgaattt  94980
tttgattgct gataagtaaa tgacagctgc taagagacat gggattttcg aacaggactg  95040
ataaattgaa ccaacctaga cactttagga ctatcttaac ttttaaaaag aagtttgaaa  95100
aatgtatttg tcaaatggaa atcaaagatg ctttggggaa gaggttttgc ttttgttttg  95160
```

atgtgaaaca agaggctgtg gattccttcc aggttaatat ggatcagggt tgactgggta 95220
agacctcctg aatcttgata ggtaacatat atcaacaaag gttacagctc atttccccag 95280
gtcttggcca ttatctcaat tttctcaggg actcctaaag atgccttcat ccacagaaaa 95340
caggaaatag tcctgagaac agggtaccca cattcccaag ggatgcagtg ggtggttgtt 95400
ggttatttgg taggttatgg atgtttgtta tcatataagg gaatatagga gtataggata 95460
aaaagacaat tattaatctc ggatattttg tattggcatg gattttagta tattgataca 95520
aattttaagt tatttttgtt gtactacata tagtttcgac ttttgtttag ggtattgtgc 95580
ttatgcagct catttaaaaa tgcagtatat aattaagaaa ggagtatcta atctataatc 95640
aaacttgtag tcatattagg tatgttttaa aggctacatg ggaatacatt agagagatag 95700
atgattttca aacagaatat ggcatttaag atgtttaata acctaaggtt tttcatgaca 95760
atgagacata tctgctcctg gaagcaccaa attactttat aaaaggatga tgggcatcaa 95820
agaacctcaa tatggagttt gctttcagtg tggcaagctt agtcatttag gcaagaaact 95880
gttcttgcct tgactgttga catatgctaa tcagactgga caagtaggac acaggaaaaa 95940
gactgttgga ctttgtcaaa acaaaacagg acagtccttc agaattcctg attcacagaa 96000
gagtctgtca ggtattctgc aggccacagg caaaagcaac agtcgaactt tgtcaataca 96060
aaacaagata gcccttcaaa tttcctattt cactgtaaag tctgccagat attacagtcc 96120
tgtaggtgga agatggatgc cccaacattg cagaggaact ttgtgtgact gtctaggcag 96180
ccatatgtct ctgttgttag gtaatattaa agccctctgg ggtctttgat ggacttaaag 96240
actaaataga gttatagttt ttccacagtt ttggtagaaa ttaaattatg tataaaaatt 96300
tggatcagta ggaaaagata gataatgtac tattttctct gaatttgcta aatacaaatg 96360
tactgaatat tgtaaatata attcttattt gataactatt ttgttgtata tagttttact 96420
ttcaaaacct ttcattttct tttagacaat atggaaaagg aaatagaaaa tacagtaggg 96480
caaggaaaca tggctgcatt taggaaagaa agaatgcaac acaaagggaa ggggattaca 96540
ttttaaaaag agaaaggaaa agcaaactaa cttgaaacag acaattgtga tcaggtgacc 96600
tccagtgcct attattctga gataataaat acacagaata tttaactata taagcaccag 96660
agtagagaga aaagtagaca tcataacaaa aagggagaaa taaaacaggg aaagcttcag 96720
aacttttaag acatttttga ttttaggtaa cttggaaaga gtcagtatgc aaatctgatt 96780
accttgggta ataagaaatt atgtttagta tatatggcac tatatagtac aggcaaaact 96840
ataaatttac agaacaggta aatgtgtaag tgatttttga agattaaaga ctgataaaaa 96900
ctaaagtcaa gtctatactt cttgtttact aaatttacta aataaagcca aactccattc 96960
aaatgttcct atatcttcag tgtttttca ctccatacac ttatatagta tgtcttttt 97020
ctaaagtact attgacctga tgctcttaat ttaacatcct atggaaactc ttattgactg 97080
tcaatttgag agattgagaa aaacacatag gacattggtt gagcacactt ttgagtgttt 97140
gtgacagcat ttccagagat gattaactaa tggatgagga gtaaaacttc tctaattgtg 97200
agaagactgg ggtcccagat gaagcacact agcaaagcat gcaccctctt tgcgttctag 97260
ccactgtgat gtgtgtagct ttgctttgct gtgctattta tcctcatacc aagcacagaa 97320
atatagagcc atccactcat atcctgagac ccctaaacca gtgagcccaa aaaattctct 97380
ccttccttta agttattttc tccagtattt atcacagtaa tgaaaagttc attgatatgt 97440
acactgtgga cattcaaaat caaggaatta aagaagatac cccatcttag aaagggggtc 97500

```
acatactgca atagaagaat gttactgagt tagcacctac cctggctctg gcatccacaa  97560
gagcaccatt cctcaagaga catcggacac ctgtgtcagc acctcccctg gctctggcat  97620
ccacaagagc accattcctc aagagacatc ggacaacttc cacctgccca gcccgggctg  97680
ccatgtgaag tgcagtttca ccacgctgcc agaaaacaaa gattgcccaa tcgtaaataa  97740
tcccactgct ctgtgtagca aagaataaag atgtcctttt tggtgaaatt cagcaagata  97800
tccaagtgta taaatgatct acaaagaggc ataattgttc agttcagaaa aacatagttt  97860
tgcatcttct gtatctttag aagggcaaat gtttgtaaat attttctgtc gatgacaaac  97920
cagtgaactt acccaaatat ccagactact ctatggttta accacatgat cagtcttggt  97980
aacttacatg ggtgaagatg tgatctttca tcctacaaac ctacatgatc tgtcattgat  98040
cccattcaat gagaaactcc agatgtcaga gatcaagtca acacattgca aaatataaat  98100
cacatcaatt atatcataaa taaatttctt ctcaaattgc aaaccttgct tctgaacaaa  98160
atcttatgtc tgatgtcttt ttttgtgaaa ttagaccaca acttatcata ggataaatct  98220
aatttttcca gtagttatcc tgatcatttt aataattgta tttgattaca gatggtgatg  98280
gagatgggta ctgagagata gtagtagctg ttaacagttt catttgtcac tccttggttg  98340
tctatgtaat actaaggtct aatactcatc gtgaggcaat gaagaagatg gttagagaca  98400
agagattatg ctcataggga aacctgttat caccaaaggg agcagggacg ttgtcattca  98460
agtaatctca tagttagagc acaatattag actaaaacaa gttgactcag cacaaccttt  98520
tcagaggata agttggcaat aaccaagcag aggaacacat tccacaggat ctaattcacc  98580
ttcaaacttg cctatgttgg aatgggatgt ttctgaaaaa ctcctgtgaa catcttctga  98640
ttctttgagc aaaataccct tgaatgtaaa agatttaaca tgaaataagt ggggttcatt  98700
gctcacagtt cccttttctc accatgatgg tgtccattgc ttcgggagtt acgggaaatt  98760
tgggtcaaac aatgtcatta gaaagcattg acctggatgt tgacttgaat gttctcttct  98820
tacaggtagc taacttgtct tctggtggcc ttattttctg atggcaaatt ttgactttgt  98880
aaagtaaatg tatatgaaac atgttttata aaatgacatt agtcaagctt gtctttaagt  98940
ctccatatgt atggtgagag atttcctctt tgggaaacta tggttttatc ctttttttctt  99000
ctgtaattca catgtctcta aataactgag actggtatct tacaattaca gaaaaaaaag  99060
aaaaactaga aatttaattt ctaggtctga tgaagatttg ctatttcatt aattttgtag  99120
aaataaaggc aagataatac tttttagaaa ttaagtcaaa gatgcctcta tgtgtttcta  99180
tgtaatgttg aatttacgtg tttattttaa gccccacttt attattaagt tttcaaaata  99240
taacaatttt ctctaatact agtcttaata tttaaaaaac tgttacttta cacctatatt  99300
aaattaccct ctggcttcta cacatttgaa gtgatgcata tatatatata tatatatata  99360
tatatatata tatatatatt gtttaagtct cattttaatg tctctggagt tcctggcatt  99420
tgctgtaaac tatgattacc tttttatatt tacattccta ttgtttatgc agaaatataa  99480
ggaaaagaaa gtcaccaaat attgcatatt gccttactta ggaccttctg tttcctgatt  99540
gtcaggaata gcctgatacc ctatttaaac aacttaactt tagacactgg tagagaaaag  99600
actttaaata taatataaag tgggaacttg accatgaatc tgctaattgg ttataagaag  99660
ataaaaattc ttaatgtcct gtgctgtgct ctcaagaccc cttgagtgct tgccattcta  99720
ctctaacaat gaattgtcag tgaatatgtt agaggtgtat aatagaacac aggtcagcag  99780
ttaaagttca cctataagtt ttctgggaaa ggaagttata aggaaaaaaa tgtgtctaca  99840
aatgttcttg gtgcatctta cactgggtat gaattttcag acaaaaacga aactggcagg  99900
```

agaatgcgca tgtgagtgtt caaagcgagt accaagagtc atgcccctct tacacagctt 99960
taaaagtggc tccgcagaca gctacattga ctctcacttc ggttgcatct agttggaaag 100020
catcaaagca caaaagacag aattgcattc acaatgcaac acgatgccag caacacagag 100080
gtgccaaggg tgggtgcatg gaggtgggga catgactgac actgtcacag caagcaggca 100140
gtccgtgtcc acacagcttt gtaatcaaat cccaaggttc tagatccagt agcaatgtcc 100200
taatgtctcg agaacacaca agttcacagg caccacctgc tagagaaagt tatattcctc 100260
taaatgtaga gttgccagat tcagcaaata aatagttcaa gtgtccattt ctattttaat 100320
tccagacaat cgggtgatta ttttaccatg ttttagtggt tgcatgacat ctacttagac 100380
tcaaaggagt tcagtgtttt atctggaatg aaaattgaat agggagttct gtgtcctgac 100440
cagcagctct acactgtctc ctatctgaag gatatagctt taaaaataaa atgaacaaac 100500
aaaaaacatc caaggatcct gctaagaagg ggtgggttga ctgaagttcc caagtgcttg 100560
tttggagggg gctgcaggga aacaatttaa agacaaacag atgaaaccaa tgaagaaatt 100620
taggacaact gccatgtggg agctaaagac tagcacagac attgccaaat ctaagatttg 100680
tccaaagcct gaaaggattg gaatacaaga aatctatgtg caggtctaaa tctctccatg 100740
tcccttctga gaccacacaa cagctaagga agcaacaaaa ttttggaatt gatcacttaa 100800
gtggtagttt gtggattatt ttttgaagga ttttcaaagg tctctactac atgaaatttc 100860
agctgggtgt ggtggagcag aactttaatc ccagcactca ggggtcagag acaagtatat 100920
ctctgagttc aaggctagcc tggtctacag agtgagtttc aagacagcca gggttacata 100980
gagaaactct gcctttaaaa accaaaaagg aaagagaaaa agaaatttca gctaagctcc 101040
ccatttaata taattgcata tatcattgtg gtaatatgat gatatatttt aacatatcac 101100
tattacttct ttaactcctg tgggtgttgt gaggcaaatg aggaaagtgg taaaatatag 101160
gggagaataa aaagaaaata gcattagtgg gtcagcacac aggagtactt ttcttgaaat 101220
cactgtcctg tgtgcaagaa tattcaggtt caatttcttc ttttgtttgt tttttgttaa 101280
gacaaaataa aattaaacaa aaatttaaaa attgtaggag ttaataaatc catgtcatat 101340
aatataaaaa ggggagaatc tggatattga gtaaataatt cctatgactg atctgtctct 101400
gttaatcttt tgataagagt ttatgatagc aaaagattaa taagtaaaac aatgaatcct 101460
tctctctctc tctctctctc tctctctctc tctctctctc tctctctgtg tgtgtgtgtg 101520
tgtgtgtgtg tgtgtttata aggcagggat tcagatgact tcctcaattg ctctccatct 101580
atttttttga agtaggatct ctcagcaacc tgaagcccat cagtttggct agactagcta 101640
gtcataatcc ccaggggtcc tcttttctgt ctccaaagcc agcactggga ttgcagaaac 101700
acccagtact ttttacagtg agtgacaggg atggaactca gagcctcata cttacatggc 101760
actcacttta atgactgtgc catctctctg gccccatgac ttctttaggc attcaaaaaa 101820
gaaaaaaagt ttaaactcaa gttggcacac taggaaatgg ctcccatact tggtgattaa 101880
aaattctcat gcaatgttac attaaggcca atatgctgtg actaaggaaa cctaaataca 101940
gacctgaaat tctttaatgg ttttatgctc tcacttttga ataatatgaa gagtgtatca 102000
aataaattgg cttcccctat ggactctgtc ccagcaccag agccttcaga cactacataa 102060
agagcagaga aatgagaatg tctgaagggc acaggtgaaa gagcaccttg gcattctgct 102120
tcacaactta aacggggaaa gctaatcccc aaattagcac atgatacact caacagctac 102180
aagtatgagc actttaataa atgaccatta atgtttatgt agggcgaaat atttaaaaaa 102240
attcaatccc cctgtggtcc caggagtgtc tactatctga ataaacacat atagtgggtt 102300
ctccttccct ggggaaaatt tgcatcatta tttgcaatga aacagtgaaa gattgtaaag 102360
ggtagttcaa gacaatgaga gaaacacatg aatcagctga aaatactagt ttaggccaga 102420
cagaattctg gaacacccag tacttaatgg cagaaagaaa ggtgcccaga gaccagcatt 102480
catctcataa tattgttgat aactacttcg ggctcgagaa aactccactg cacatataaa 102540
caagatggaa gttaaactca gtaggacatg gcaaatgtaa tgtagaatag aggatacttt 102600
gatatcacaa acaatcaccc tcactgaggc caatatctgg ttagtctttg ccaacattga 102660
ttatggagct cattttaatg gaaattacct ggaatacaat gcattcaagc aaactagggt 102720
gagccctgaa aactattttg ccatccatcg ttcattcact ttcaaaggtg tgtgtttctc 102780
tgaagcacac cgaaggctga ctcagactca caagtcacct gccttagttt cccaacagct 102840
agggactgca gatgtgtatg accacacagc ctcggggagt tttaaaaaca caccctgttt 102900
tactacatgc attagatgaa tgtttcatcc atccgcacca ggaagcctaa gctgtgtgga 102960
tccctacctt ccatttgttt tctgacacct gattctgcat tcagcaaagt tccaaacgtt 103020
acattacaaa acgttatttc agaggccctt ctcggcgctc tgatgacaca cacatacaag 103080
cccacacacg cccactctga ttcgtttgtt ttctaacacc tgattctgca ttcagcaaag 103140
ttccaaacgt tacatcacaa aacgttattt cagaggccct tcttggcgct ctgatgacac 103200
acacatacaa gcccacacac gcccactctg attctctcac tctttctccc tgtggttatt 103260
ctgacccaag ccatactcac aatgttagtg acatctggag aggctccgtt ctgcagcaga 103320
aggaggacaa tgttcaagtg gcccatgaaa gcagccacat gtattggtgt gaggccagac 103380
tgcgaaacaa agcaacagta gttttactcc tctgcaccgt gggctttggg gcttcttcag 103440
ataaataaga caagcgaaaa ggacagaaga tggatgagag gaagagggag gcataagagg 103500
aaatgtttgg tgagaagctg aaacactttt ctacctctgt tatagcttgg attgaagccc 103560
catatttcac cagcagttcc atgactttga tgcggttttt cttgcaggca atgtgcagtg 103620
gagtaaaacc attctgtgca aaagacaatc gagttagttg aaaacatgca gaaacaggtc 103680
tcacacagct ccatgctggc acatcacagg cgataatgtt gcatcgtcac ataatgtcac 103740
cgtctcttcc gaccctatag aggtggaaat ttgggatgag aagtggtggg gtgtgtgtgc 103800
ttttgggaag cgaattttgc ttctgtcatt gtgagtgcat acagagaaga caaaagcaga 103860
ggaaggtatg tgagcttact tttcagggga gaaaaaaaat ggagggcaat tatgtattag 103920
atgggctaaa gtgttttagg ctgtcttgac cggtcaggtg atggagaaaa agatggagtg 103980
agcagaggta cattttgatg agggagggcc agtttctcag agcataagaa tcgttcatct 104040
acttcaaaaa gctagcaata gcaatatgat ggctttataa aaagtgtttc agctttgcta 104100
ttattttctt agggagagtt tcaaattagc agaaatcatt tggctgacag tatttataaa 104160
agaagttaag ttttatatta aaacatgtgt accaatcaga tatatttggt tttataaaaa 104220
aattaacttc ccagatatat tttattttag gtggaaatga ttgcattcct gaatattttc 104280
aagaaagata tggtgaactt ctggatgcct gacagatgac acctctgaga gctaaagtta 104340
agtggggctt ctggaaggta atctaggtta ctattcagga attggagaaa tcacataaaa 104400
atttacctag ccccatgcta aattgttatg ttttatatct gttgtctttt tatttgaata 104460
attgttcttt tacagagtga tctctaactt gtcaattaac agtttcaaat gtcccagtgg 104520
ggactgactg tcatttgata ttttggtatg ttaccagttc tcaggaaaac atggtttcat 104580
ttagtcagtg acaatgtatc ctttttagtg gagtggtgga cctaatttgt tgagtcgtgt 104640
tccctgttta taaactatgt caccagccag agataagtag taacaagtac atgtggcttt 104700
aaaatgcatg caactaatca cctgtcgtag attacaaact ggttcttcac tatctaaaga 104760
aaagtgtttt caacttctta tgagaaaatt cagttcttca catatttgaa catgaccctg 104820
gaagtttaat cattttctaa gtaaatagta atagatggat tccaccgaaa tttttcaaat 104880
aaattagtat gctcaatatt taataattta atttatttat tactttactt attgatcaaa 104940
tggttgattg acttttgaga tagtgtgagc tcatttatcc caggctggca ccataggatg 105000
acctcctacc gctacctcct gaaagctaag attataggca tgtgccatca tgtgtcatct 105060
gtgtggtgct ggagatcaaa cctaggatct catagatgtt aggccagtat tctaccaatt 105120
cagctactac cctagcccaa tatttaatca ttttaacaag agactcccaa aactgaagtg 105180
aattttagtt gacataaatc atgtaaacat ataggaaaac aaagcaatgt gatcttaaag 105240
tgagaattag aaaatgaatg gcataaatta gtacctgccc aacatactaa ttggttagtc 105300
tataagtgaa gcaagaaaga tttgttccat attattagac catgggagac acaaagctac 105360
tgtgagatgg cttcctacat tttctcttga gcaggccatg gaatgctttc ttcaaaatgt 105420
tttgcagggc agtaatacac tgagaatcac caagcccatg gttatgtagt cagtccataa 105480
agaaaatatc caagtgaact ctcaaaagct tctgtcttag accttcttaa agagtcaaat 105540
atattcacca tttttaaatc tttgttttcc ctaggagatt cataaagatg aaacttttca 105600
tacctgtgtc ctaaatccag ctagtatttt gaagtgccta gaattgattt tgttatttct 105660
ttttccctct gagacagggt ttctctcttt agacctggct gtcctggaac tagctctcta 105720
gaccaggttg gcctcgaatt cagagatcag cctgcctttg cctcctgagt gctgggattt 105780
aaggaatgca ccaccacatc ctgttatttc ttattttata acatctagct tctattttaa 105840
aacactcacc atcccagagt ttcctactgt ttgtaactca caggtttcag aaataataat 105900
ctggtgttct cctaaatctg ctcatgttca ctaccactta ggaaactatg gaagcatgaa 105960
ttaggctgtc agctttcacg gggtgacaag cttggcagct attaagtgtg gatttataaa 106020
catgcatggg tgcatgtgcc attggccaat caatgtgatt ttcctttctc aggctgtatt 106080
tggtgaatgt ggattgggcc aggtttacca gggctctcgc attcgggttg gctctcttgt 106140
ccagaaggag tttggtgaca cggtagtgac cacaatgtgc agcaacatga agggcagtca 106200
ggtaatccag ggtgacatca tctacaggtg ccttgtgctg tagcaggtgc ttcacacatt 106260
ccacatggtc cccctgtgca gccatgtgaa gaggagacag cccattctgc acaccaaaac 106320
aaagaaaaac caagtccatg ttttgttttt attactctca tgtttggggc cctaataaag 106380
ttaatcttta tcagcaacac agctggaggc aggagaaata actcttcctt aatatccaga 106440
tgcagaacag attatgttaa gtaaatagag aaggaaaggg tatatttaat tttataacca 106500
taagaatctt tagcaaaaga cattacatgt ttttcatagt gtcaattcaa cttgagtttt 106560
aaaaattatg agaatagtat tagatatata gaaatgctgg cgcatgcata aatcatttgt 106620
atctaatact acacatagca atctccatta gattatctct ctacttgcat ttcttttccc 106680
ataatcagag aaggacttgg gtaaaggagg gaaaagtgtg ttcatgggtg aagcagatag 106740
gaaaaaattc accatgtctt aggttcaggc ttcagaaaaa ttctgagatg cttttttcca 106800
atagtaatac aagacttacc ttaaagtagg aggaaagaga caggtaagtg ctagaagaac 106860
aggaaaacag tgcaggtcat atatcaatga cctcatggct ctcaaacttg aggacagcct 106920
agatttctga ttactaatat agacacaaac agctttcacc ttaactctga aggcaatcaa 106980
tagtaaaact taaaagatag agtaagccat tcttcatggt cagtctaagt taaaaacaac 107040
tccctatttt gtggagttgg ttctctcctt ccacctttac ataggttcta gaagttttgc 107100
ttgataggtg ctttatagcc tgctgagcca tcttgtcgaa tctccaacca ccaccccctt 107160
ttttaagggt agccaaataa acttcaagga agtactcaca aaattttagg aagaaattgg 107220
aatattgttg tgctaactag ccacacaggt accatcaaat atagttcgtt gataaaaaaa 107280
aaaaaaaaag ctattttggt aaccatgata tcgattcaaa gaagtagaaa tcatgtatgc 107340
aaaaaattac aaaaaaaggc tcacagccca atattctcat caggaaaggc aacttcaaga 107400
atgagaaaca gccacaacct aatatatgaa aatcctaatt gtggttgttt tcgggtggaa 107460
gagttcaagg gaattaaaaa tgatgttatt tgtttctgaa atgaactgca ttaagaattg 107520
ttgctttgat atttagaaat atgttaaatg gactttgaaa acaagagcag gttgataaga 107580
aagtatgcac tggaggggaa gataatgtcc aggtacagaa aaaacaacat ggccattgac 107640
aatgttcaga ctggagtggt aaattctcat ctgaaatttc tgtcattcac tgatgctgct 107700
ttatccattt gaaggttatg tgtaaaacta gtcaccattt caatctttgt ttaacccagg 107760
gtcccccagt aatttccaac tgtccttttc atccttctct tctaaaatat ctccatttcc 107820
ttttagccac caccctcaga aacacttcct actagggacc accagtggct acactacgcc 107880
aagtaacagg cgattttcac tatccttctt gtcttccact tcaggactct cctgaattac 107940
ttattcctgc agaagcccct catccaaccc tgcctctact ccctgggaca caggtccctc 108000
tagtattttc ctgctgctcc tctcagcctt tcttcctagt aatctccact cctttgtgtc 108060
actcaccaac ctgcagaaac agtctttacc aaggacccca tgcacaccac acttgcctag 108120
gatacagagt aggcaacagg aactaataaa cacaacatgc agccaacaaa gataagacca 108180
gatatctaca ccaagaaaca acttaaacat cattacacca gatgactaga tcccagcaaa 108240
aaaacacaaa cattaacgac caagacaaca accccctcta aaagcaataa tccccccccca 108300 aaaaatgtaa tttaactgaa gcacaaggac ttcaaaataa caattaggaa tatattcaaa 108360
gaccttaaag atatatgaat aagtgcctta atgaagaccc tgaaaacaca aacagttgaa 108420
tgaaataatg aaaacatctc aagaaataaa aataaaatca ctagagaaaa tccaaactga 108480
aataaaactg gaaatgaaaa cttgaggata tcaaacaaaa acctcagaga taagccccac 108540
cagaaattac aagccatgaa aacgagaatt ccagatcttg ttttaaaacc ttttattaaa 108600
gatttattta tttattttgt atagagtgtt ctgactgcat gtatgcctgc acaccagtag 108660
tgggcacaag atctcattat agatagttgt gagccaatgt gtggttgctg agaattcagg 108720
acctctgaag atcagccagt gttcttaacc tctgaaccaa ctcttcagcc ctaagaattc 108780
cagatcttga agccaaggta gaagaaatgg atatctcagt ccaagaagat gtgagatcaa 108840
aaaaaaaaaa aaaaacccac ccaggaaatc tgggacacca tgaaaagacc aaacccataa 108900
ataaataata catatgtagg aataagaaga aaaccaggac aaaggcatag aaaatatttt 108960
aataagatga tagaagaaaa tttctccagt ctaaagaaag atatgcctat caaggtacaa 109020
gaagcatata gaataccaaa cagacagaac aagaaaagaa actgctcgtg acacataata 109080
attaaggcac taaatgttca gaacaaagga aggatattaa aaaacttcat gggagaaaaa 109140
ccaagtcaca tttaaagtca gactcgttac aataacaccc aacttttcaa tgtagactgt 109200
gaaagccagg cgtgcctgga gttgtgttat acaatctcta agagacaaca gatgctatcc 109260
aagattacta tatacctgag gatttggaga aagagtcgtg tgcatactct ataagacaga 109320
agaaaaacaa atgcaagcac tttatgttgg gaccacactt gaaagacctc aatagtaagg 109380
aagacctcaa cagtaaggaa gcaaatgtgt catcaggtaa gtagattggg agggtgaata 109440
aggagaggag ttcagcggca taagagactt tgtgagagag gtcaggcgtg gttggaaggg 109500
ctgagacaac aggatttgcc ttgggtaata tgttcagcat agctgggttg cagaaaaaag 109560
aactgaaaac aggggcctct tgcaaccatc caagtgcaac gcatggtggc aatgaggctg 109620
ttcaacaatt tctgatttag tgatgtatat agaaggaaaa agtaacagaa tctggagtga 109680
gaaaaggagg agcccagcat agtatgaggt atctgagaaa tttaaagaat gagatgccca 109740
tgaatgaata tacaaaattc agagaaggct atatttaggg gtaggcaatg tatcacaacc 109800
ttgttttgaa ctgcccagta aatatccaag aagtcaagag aagctgtcat gaacatgtag 109860
aattctagaa atatccacat gggtgttagc agagtacagg tactgtttaa agatgaactt 109920
cagaggacgt gaataggaga gacagagcca acacaaaatg tggcctctaa cacagaattg 109980
gtaacatcca gagaacaggg agataaagag gaaatagtca cagagactgg ggagcagatg 110040
ctggagatgc agaaggaatc caaagaaatg tcgtgtccta gaaggcaaat gagaaaagcg 110100
tttggaaaag gaaggactgg gaagctgtgc caggtgatag aaataggata gaacacgggc 110160
tccacgggct ctgattcatg cacctagata gctgtgaaag tgggagtttg tggacattgt 110220
ctcctgcttg cttcagtttt tctcagtgtt gtatgaagaa aaaagagatg tctaagcaat 110280
atagagaaga attgtcgctt ggttagatag cagggagcaa gatgagtcac tatggaaatt 110340
gcactgtaat ttgtcagcca atacactggg ctaaactaag gttagtgata atgagtctga 110400
agggacttcg tgattggggc cacactcagg tacaagaatg tgacatggac ttagtcacca 110460
gaggctgtag ggagttgttc aagggagtga tggaaatgga acttcattgt tcagaggtaa 110520
gggcccaggg tgaagatgga aacagtacaa ctgcctggga ttagagactc agagtgagcg 110580
agctgagacc taggaggggt ggttggagaa tgtgaggtta gagacaggaa ctacacagac 110640
cttacagtca gtaagtacag ttgagaattc ataatcatgg attatggtga agattcattt 110700
tgctgagagc tatagctttc aaagaatgag gagaagttgc tttgaggagg aagactgggt 110760
aactcaaaac tgagagctgt agtggggaca caatgccacg catgtgctag tggcatggtc 110820
ctactccaac cccgtcaggt catctgctcc aagtccatta ccctcacaga gctctgcttt 110880
tcataatctt ctcctgtctc tcctgccctg gagattctaa gtttcttcat gatactttct 110940
gtttagtatt catcttgcta gttcctgggt aaccagaaca gtgcctggca cattgtattt 111000
tctccataca tgacatagat ggatgtggga ctcaaggggt gtcaccatgc ggttaccaac 111060
actctatgct gaacccttaa atttaaatga ctcctgatta gacaggaaag tcatctcaaa 111120
aatcacactt tgatcatcca tactcttgct ggttatgaat ctattttaac caaagggtaa 111180
aggtcacttg aaaatttctt ggaagaccat gtaggcctca attttataag tattttaaaa 111240
ttttgggtgt aacatgattg gactgaaatt ttgtttccgt ttaaattgca ctctacttcc 111300
tcaacaagct ctccaccatt acctctgcct aacccagtct aaagtgttgc atattttaaa 111360
atatgttttt gcaacattca tagtacagaa tgataatgaa aacaatgcag atagcttact 111420
tcactttatg tatttcttgt acgaagctag tttttttttt tttttttttt taatggctgg 111480
tggaacatat cttagagaat gactgagttc tctatatatg ttaagtgtgt gtactggttc 111540
gctccaaatg atatcaatga aattatcaat taaaaaagaa attgagccag gcatgaaggc 111600
acatgccttt aatctcggca catgccttta atcttaggag gcaaaggcag gctgatttct 111660
gagttggagg acaaaccagt ctacagagga agtttaagga tggccagggc tatacagaga 111720
aactgtttca aaacaccaat tcaatattta tgatgtacaa aattatctat caaggcaata 111780
ccattaacat tggaagataa agctttgagc ttctctaatc tttttctctt tggggtaata 111840
ataatgagaa caatcactat tacttaatag tggagtcggt tgtggatgct gcaggtgtgt 111900
gtgtgtgtgt gtgtgtgtgt gtgtactttta tgagaggcca gtgtcttggt tttcttcatc 111960
ttgccctatt tctaacatta gggaatacca gcattattaa ggtgtgggac tggagtggaa 112020
tctggagaaa aatgtaagag gttcacatca gaatttttgt tatatttaag gatctaaaaa 112080
ttgtttcata tcccattaaa taatgctggg tgattaaatg tcaacttatg tttcatagta 112140
ttttctgata aacattagag aaacaagcaa cagtaagtgt acagatatca acaatgaaaa 112200
cctccaaaca attcatttac tgtgtggttt ttattcacat gtaaatgggt tttcttgctt 112260
gaacacttaa agtgagggga aaaaagttca gtgtataatg ccatacagaa cagaatgctt 112320
gatttagctt gctttgtggt tctttatagg tggctaatct taaggtatgc tgttcctatc 112380
acctttataa gtccctaata tagccaatca actctactat taactaatta ttctaactat 112440
tattatgaaa aagaaaaaga ttaaatatgt tcaaagcttg atctactagt gttcacatgt 112500
ttcatagagt catcttagaa agtcatataa tatgttagct catgcaatgt aattgtctca 112560
tatatattaa tatatctaat tttcttattc tttttgtttt ggtttttcta gtcagggttt 112620
ctctgtggtt ttggaggctg tcctggaact agctcttgta gaccaggctg gcctcgaact 112680
cacagagatc tgcctgcctc tgcctcccga gtgctgggtt taaaggcatg tgccaccaac 112740
acccagctaa tattcttatt ctgatacaat atggttagtc aagttttaat ctacaataaa 112800
aatagcttta aaagacagga ggaacctaga ggtattcatc tagcatatct tcatgcatgc 112860
atttgctcat tttaatagtt ttgcaagttt ggtattattt cttatttcta gcatatagaa 112920
taagtaaaaa actttaactg gtgctttagt tttaagagga gagattatag aaaatgcctt 112980
aagtgtcctt ggatgccgtc ttactcataa tgactcacct tggtccttgc cagcaaggga 113040
gcaccccgtt ccagcagcag cgccaccact tggtcatgcc cacttcgtgc agcacagtga 113100
agtggagtca acccatcctg acaagagaat taagataata aatctgagtt gtcactcatt 113160
tacaaacaat attatgtcta ttgccactga caggagagag gctctggtga cctaataaaa 113220
tcacaacaaa atggcagtac ttgcctaaca catgcacaca acacatacac acagagggag 113280
ggaaggggaa ggaggaagag gaagagaaaa gggtgaatga aagaaagaaa agagaaagga 113340
ttatgacata cagaactagg aagggaaaac tttggctccc cccaactctg tcctgataca 113400
ggtggactga ctggattaga acaggctgac ttctggtcaa atgtttgcaa acccagatga 113460
aaaggcacag agcacattga cggttgtatc atcctactta cttggagcca aagctgtggt 113520
tgtactgtta tgccctttga ttttagcttt cctttgcatc attttgattt aaaacttctt 113580
ctttctctaa tttgtccaag aatattcttt tatgaacagt aactactttc tcatattttc 113640
caaaagtatc ttgtggtgcc ctgaactttt catactcttt taagaatttt cagcatttaa 113700
caaaaatcat acaactattt caaagatgaa attcattagt aacaaataca actaaaacta 113760
tgaattttat agctagttaa aatgaaagga gactatcagt gctgccacca tacctgactt 113820
tgtcctttga gttgtgacaa tcaaactcag gtcttgaggt tttgtagcaa gcactttacc 113880
aaaggagctg tctccccagc cccaaataca gactctttaa gacttctgat tacctaatta 113940
aatttgagtg tcccacttat ttttgattag gattttgagt aataatgact ctttgcttta 114000
ttgcatctta ttagccactg aagaattaaa accaatgttg cagtttcgga gtgttagaat 114060
tagcatgaaa agacaacatt ttaaagaaag catttagcca cagctgttga gggctgccaa 114120
attattttca agattttcca gcaggaacag aaagagagat tgtggtgagg aaaatgataa 114180
tgattttctg tcttgataca agcaccctgt agtagtagta gtagtataag ctgtgtagta 114240
aatgacatag cctggtttct caaatgcatg cttggtggaa cttcatcttt ctttagtttg 114300
aggaatgtca gtcagatatc agaggactct gtgccctaga cacagtgaga acagaagaag 114360
atcaaaagcc tttgaccatt ctctatgagg tgaggctcca cactatgcac agagaggacc 114420
tatcatctgt cctacagcct tgagaaaatg acaagatgag acatgctggc ttacatggct 114480
ccaagtaaag ggagatacat cattttgcat gaactgcctg aaatactctc tctgtaatca 114540
tggtaaagcc acaaaaatac cttccacaca gtaggaactt tgtggagaac ttctggcata 114600
cccacaagag catcaaagaa tgagtgagga ccaagttctc agtctcatgg ttaatgaggc 114660
aatgcacctg cccttatgaa agaccaggga ctactgatgc taaattcatt gtctgacaag 114720
ctcagcctgg ctggaatttg aatctttact acaaagcaca ccatcaaatt actgccaatt 114780
cttgttgggg ttttatattc ctctaagtta tactttgaaa gctaaatttc actaccatcc 114840
aaagttccct tctccatgtg cctttccttc ttcactaaaa tcagacagac agacaggcag 114900
acagacagac agacagacag acagacagac annnnnnnnn nnnnnnnnnn nnnnnnnnnn 114960
nnnnnnnnnn nnnnnnnnnn nnnnnnnnnn nnnnnnnnnn nnnnnnnnnn nnnnnnnnnn 115020
nnnnnnnnnn nnnnnnnnnn nnnnnnnnnn nnnnnnnnnn nnnnnnnnnn nnnnnnnnnn 115080
nnnnnnnnnn nnnnnnnnnn nnnnnnnnnn nnnnnnnnnn nnnnnnnnnn nnnnnnnnnn 115140
nnnnnnnnnn nnnnnnnnnn nnnnnnnnnn nnnnnnnnnn nnnnnnnnnn nnnnnnnnnn 115200
nnnnnnnnnn nnnnnnnnnn nnnnnnnnnn nnnnnnnnnn nnnnnnnnnn nnnnnnnnnn 115260
nnnnnnnnnn nnnnnnnnnn nnnnnnnnnn nnnnnnnnnn nnnnnnnnnn nnnnnnnnnn 115320
nnnnnnnnnn nnnnnnnnnn nnnnnnnnnn nnnnnnnnnn nnnnnnnnnn nnnnnnnnnn 115380
nnnnnnnnnn nnnnnnnnnn nnnnnnnnnn nnnnnnnnnn nnnnnnnnnn nnnnnnnnnn 115440
nnnnnnnnnn nnnnnnnnnn nnnnnnnnnn nnnnnnnnnn nnnnnnnnnn nnnnnnnnnn 115500
nnnnnnnnnn nnnnnnnnnn nnnnnnnnnn nnnnnnnnnn nnnnnnnnnn nnnnnnnnnn 115560
nnnnnnnnnn nnnnnnnnnn nnnnnnnnnn nnnnnnnnnn nnnnnnnnnn nnnnnnnnnn 115620
nnnnnnnnnn nnnnnnnnnn nnnnnnnnnn nnnnnnnnnn nnnnnnnnnn nnnnnnnnnn 115680
nnnnnnnnnn nnnnnnnnnn nnnnnnnnnn nnnnnnnnnn nnnnnnnnnn nnnnnnnnnn 115740
nnnnnnnnnn nnnnnnnnnn nnnnnnnnnn nnnnnnnnnn nnnnnnnnnn nnnnnnnnnn 115800
nnnnnnnnnn nnnnnnnnnn nnnnnnnnnn nnnnnnnnnn nnnnnnnnnn nnnnnnnnnn 115860
nnnnnnnnnn nnnnnnnnnn nnnnnnnnnn nnnnnnnnnn nnnnnnnnnn nnnnnnnnnn 115920
nnnnnnnnnn nnnnnnnnnn nnnnnnnnnn nnnnnnnnnn nnnnnnnnnn nnnnnnnnnn 115980
nnnnnnnnnn nnnnnnnnnn nnnnnnnnnn nnnnnnnnnn nnnnnnnnnn nnnnnnnnnn 116040
nnnnnnnnnn nnnnnnnnnn nnnnnnnnnn nnnnnnnnnn nnnnnnnnnn nnnnnnnnnn 116100
nnnnnnnnnn nnnnnnnnnn nnnnnnnnnn nnnnnnnnnn nnnnnnnnnn nnnnnnnnnn 116160
nnnnnnnnnn nnnnnnnnnn nnnnnnnnnn nnnnnnnnnn nnnnnnnnnn nnnnnnnnnn 116220
nnnnnnnnnn nnnnnnnnnn nnnnnnnnnn nnnnnnnnnn nnnnnnnnnn nnnnnnnnnn 116280
nnnnnnnnnn nnnnnnnnnn nnnnnnnnnn nnnnnnnnnn nnnnnnnggt gtgtgtgtgt 116340
gtgtgtgtgt gtgtgtgtgt gtgtgtgtgt gtgtgtgtgt gtgtgtgtct gtccctgact 116400
ctttcccaca cctgctctct cttccaccct ctccacagtc cacagtactg agcatcaagt 116460
gtgggtggac tcagatatgc tgggcaagtg ttcttttact gagcaattcc accagcatct 116520
gactttttat ggaaagatgg agagctgatc tggcttgtgc tgtgttgggt ctcctgaatt 116580
cgtggtacaa gaaggaactc agagcactgt ggaggggatg aaagaacaga atgtccacac 116640
tctacacaga actaaagaat ctcctctttg catcttaatg cttgattaaa attcaattta 116700
ctttctctat ccaaaggcta cacaggaaca cagaatgtgg ccctgaattc ctttcccaat 116760
gcttccactt gataacttcg ctaagaacaa ttagttaaag gcaagacaag tgtaagagtc 116820
catatctctc tatttctgag tatgctttca tttttgaaaa caatgctatt agtgtttgta 116880
tgtgctatgc atgtgaccca tgaagacaag aacatctttg aagaaatcaa gaactactat 116940
agtgacaaat acaagcaaaa tcaattgctc actaatgaat acatgctcca gaacagcgtt 117000
aacaaaagca gtgaacaacc gtaagacacc agccaagatt gttaaaagtt attgcactaa 117060
gctttaaaaa cagggaagaa taatgacagc aatgcaggca gcagacaaag cctgagcatc 117120
ctcaggttct cagattgccc ccagtttcct acccacatca cagcaggaga aggtcccggg 117180
ttacaaggca aaggttgaag ccaggcaaaa ctacacaagg aaaaggtaca acactctgga 117240
cagacagaaa aacaattccc aaactcccat atggcatgat actgctgccc tggaacagtg 117300
ttataagaga aatgaggtgg gggttttgct tgtttgttat ggttggtttc agcaccattt 117360
ctggagctaa tgaaagaaaa caacttgtag tgttcgactg gtacagattc taaaagctaa 117420
acaattgcta gcttcaaggc gggtaagtgg cctggatttg acccttactg tttagtctgg 117480
agaatatgga gtcctaaaat gtaaaaatgc atggagcaaa tacatgttct atctaccctt 117540
ttcaatagac tttgttgttc acacataatt taccagggat ttctttcttt tcttttcttt 117600
tcttttcttt tcttttcttt ctttcttttt tttttcttgc ttgcttgttt agttgacagg 117660
gttttttgtt ttgttttaaa gagtttttag cttgactttt tttgacaatt tcctaaatgc 117720
ctgctatatt tcagcccacc ccttttgcca cttcaactct tcctgtgacc actccctcac 117780
actcatgacc tcgtctttat tattgctaca cacacacaca cacacacaca cacacacaca 117840
cacacacaca cacacacaca ccactgctga atctgtttgg aatagttcat gtgcgtctgt 117900
gttgagggct tacctcttgg gattggatat taccaggggc ttgtctctgg ggaaggctta 117960
ttgcccctct tccaacagca attaattgcc tgcagttttt cacctacatg tagcacccat 118020
ccagattccc ccaactgtac tggcatgtca cctgatgttg ttgttacacg ggccttgttt 118080
ccatgaccat agtcttagat ttcataaggt tgtatgaggc ttaactcata gctatgttat 118140
tttcctctca tatatagaag attccttctc atatatagaa gattctatct ctaaatgaaa 118200
tagggttttt tgtaggaggt tcttctgttt gttgttgaga cagggtctct ctacataatc 118260
caggctgacc tcaaactcac actgtggccc aggctgacct cagaattaca atccttttac 118320
tctcttctgt cagagtacta ggattacagg tgtacataat catattggga atacaggtgt 118380
acaagactat gcctggctca attttgtatt tcaaaactac tcaaaattct tgtgaagtct 118440
cttagtaccc aaatctactc cagaaagcca atattacaat acaacactct atatagatac 118500
atatatatgt ataatgtatg tttgagcaaa aagggcatat aatatcagca ttattacaaa 118560
aaatatgagt ggctaagtaa ttgatttaca ccttttcctt cctttcttct ttctttttaa 118620
agataattta atgcagccag gtggtgatgg ctcatgcctt taatcccagc actcgggagg 118680
cagaggcagg cagttcaagg ccaaccaggt ctaccaagcg agttccagga caaccaggac 118740
tgttacacag agaaaccctg tctcgagaga caaacaaaac cctaaaaaag agataatttc 118800
atgcatctga ggctagctaa ggataaaatt aaacttctga tctgtctgac tataccttct 118860
gaatgttgga tgttagtatt ttaagtgtgc tacaggtgtg taccaccata ctcatttgtg 118920
gtgctgggca tctagctgag ggctttatgc aagataggca ttcactgcac taactgagct 118980
gtatttccac tttgttaagg aaaataacat agctattagt taagcttcat gtaaccttat 119040
gaagttaggg ggtactggta gctaaattct gagatcagaa aatgccaaca ctatctagct 119100
taatgaatga cacaaacagg atttgagatc agacagcttg tctttttaac atagtttatt 119160
cactatatgt gcattaagat gttaggatat aattccactt tagaaatttg aaatgaatga 119220
agggctccac ttctactgag atgaaggttt accttgccaa ctgtctgctg actttctgtc 119280
agtgtgacaa tgaatatagc acaactaatt aaggagcaca aaaactgtca atatgcatga 119340
aaccagtttt gcataagtca cagtctcaag acttaaatgt gccaatcaat ctgccttctt 119400
gatgactacc caaaggagaa ctgtggatat gcaatctttg atctttattc ccagaaactg 119460
agcaagaaaa actatcacaa cgaggggcta gtagtctgtg tctctgggca tctatgagca 119520
aatattaatt tcattttatt agttgaaatc tgtgagtatt gtgtgagact caaatcaaac 119580
cccagagcaa tctccttgaa aatacactgc ttgtgtttgc tggctagtgt tgcaatgtat 119640
ggaatgaaag acagcagggc ttaagaactg taggaaattc aaagtgcaaa gatactcacc 119700
ctagttttgg catcaatctg accacctcga tccagtagga gcttcaccat gttggtattt 119760
cctcttttag aagctacgtg caggggagta attccattct atatcatggg aagaccaaac 119820
aataggttag atatgacaca gtatgagggc gtgacttcct agtaaagagt accaagggat 119880
tgggacctgc gtgacccatt gtatctaggg ttcaataggt ttgatcataa gtaataaaga 119940
agcccataaa ccatgggatg ctaattgtta gaaaatgaaa agttaaacaa aaattcatgt 120000
tggtcaaaaa aatacaatat tcacattgaa tgtaaaacaa gataagacac agaaggagga 120060
cgtctgtgtg gcagaagcta agcctcaaat tctaatattg agcccagtga aatatgttta 120120
taacactcat gtactgtaga gtttgagatc tcaaagtttt atatgtttaa aaatggaaaa 120180
atatgcatat taatatcagg ggtaattatt ctttaaagcc ccctcagaat aattcacaga 120240
gaaaaataac tggaaaatag tacatcatag tttcagaaca aaaaatttct tttccaaaca 120300
ggattttaat acaatagctc agactagcct agaacttgcg cataacatag gttagcctta 120360
aactagaact ccttctggct gatctgcaga gtcctaggat tatagatata tgccaccaca 120420
caagggttgt acaaagaatt ccaagaactg taatagtgca cacaagacta ctttgtctta 120480
taaggtatca ggtgtcatca ttatggcatg tatatgtgtc tgaaaatttt gtgtgtcaca 120540
gtttaccaaa tatgtaaaag actgtatcaa catgaatcat gcttaaaaaa tccattccat 120600
atgtgaattt tatactatca tgtaaatgaa tttttctaat ggaagcagaa tattacatgc 120660
ataattccat gcgctgtctt cctatgtatt ttaggaagac atcagaataa attttcaatt 120720
cgttaaccca tccacttgtg tatccactta agaaacactc cctacagagt gtgtgctatt 120780
tcatcactgt catctactga ctagaagctg atcattcatg ttttttttt tgcattattt 120840 tataatacag cagtagcagt caatgccatg ccaaaagtag cctcctcaac tactaatgca 120900
gacttactta ttttctatgt gtttgagtgt tctgccctca gggtccaaaa gaggacactg 120960
agtccctgga tctggaacta taggtggtga gcaactcaac aagggtggga gtcaaactca 121020
cacccaccag aaaaacaaaa ggctcacccc tgagtcatct ctccagcttc cagagtcttg 121080
ttttatttat tgggttatga tactatcctg tgattaagac agtgaaaact acagaatctt 121140
taggatggta aaagagggtt aaatataaga ccttaatgga agatttactt tcttaaaata 121200

```
cacgtgttta ccacataccc tggctgtgaa gtccactgca gctccccggt ttagaagaag 121260
agtcgccaca ttgacgtttc cataatgagc agctatgtgc aaaggggtga agccgctcta 121320
gagaaaagga gaaatggtgg gtagggatgg gcctcaccct gtggaaagcc accactgact 121380
aaccagaaaa cttactgggt aaccgactgc caagtacatg agcaacgcaa ctcatgtaag 121440
aaacgctgta atacaattct atggcttagt gttataagag agaaataaat accctacact 121500
ggctggaaat ttcattttta atttatgaga tgagttgtct atttaagcta tgtgtcttga 121560
aatctttagc ttatcagaga aactcagaat atgatgaaac cacataaagc ttcaaacaca 121620
ggattaacat ttactaatag atgttttcat ccagacattt taaaagcagc ctttttgttt 121680
tcatttcttt ttctatctcc atgtgtgggg gtggaggtat gaatagttgt atgtgtgtgc 121740
cagaggaggt gtgctacgtc tcctcctcaa gccctttctg gcttattccc ttgtgacagg 121800
gtctctcaaa acttggagta gctggcgagc agtaggaatg agcaatcaca tttccaccct 121860
cttagaagaa gggttataga tttgcacgtg gcacacccag ccttttttact tgggctcagg 121920
aaactggaac tggggggtcc ttatgtttgc acagcaagtg gtgcatccct gctgagtcat 121980
cttcccccac cgattaatct tatttataaa agagcattgg ttggcatttt atctgcagga 122040
ctgtgaaaat ttctcaggaa aaatgtctag ttcattctac agcatccaca gtgattttct 122100
atccttttca caactgcata gactgtgaca tatcatgaaa aagatttaga aaccaatatt 122160
aaacaacttt tcttcctatt agattgtctt gcccagcctt gttatgaggg aatttgcctt 122220
gtcttagtgt acattgtttt gtcatgttgg gttgttgtct cttgaaggtt gtggtctctg 122280
gctctttttt gaagggaaac ggagcagaag tgggaacatg ggagaggaga agtggggaaa 122340
attggcagaa gtggagagag gggaaactgt agtcagaatg tattgtacaa gagaagaaac 122400
tatttttttgg agcagaagtg ggtacatggg agaggaaaag tggggaaaat tggcagaagt 122460
ggagggaggg gaaactgtag tcagaatgta ttgtacaaga gaagaaacta tttttaatga 122520
aaaatacttg ggatcggtat gaatatgaaa taaaaatggt tcaattgaat ctaatttcaa 122580
atatgaacta aatataattt tatcactaaa ataaaatatg attaaaataa ccacattaag 122640
gaaatgatgt ggatatcaga aagatacctc atttcccaaa tgcttcaaaa acaaaatctg 122700
agaatcaaat gaagaaatca tttcattttc tgatgaagat atagttagat atttttgctg 122760
tttttcccaa tagatgtata ttagctggtt ccttattgag ttgctcaagg agctggtaat 122820
tttcattatg ctctatagtt ttcataactt aattaaaata tttgaaagga aacagcattc 122880
agtggctagt acatcctctc tgcagtttgc aggttatttc ttattttctt ttacttataa 122940
atggatttca atgtgtactc tattgcttta agaaatattc tataagccac aaccagtttt 123000
tattgacttt gtgtatagga tttggtgata ctgtgttcaa aatgctaaga taaacattta 123060
ggtggcttag gtaattgaag gctgcagatg aattcagcaa cataagttgc caataatttt 123120
taactgtaaa gcagcaatag gaatagcaac tgtgaattca gtctccacaa ttgtgatcaa 123180
gatcatttta ctctacatgt aggtggtgta ttcatgccaa aactaagggg gagatcagta 123240
tacaacccat aattatttta taaaatgtca aatctttttt ctattttcac cttgatattt 123300
cctgtcaccc agacatattc tgagtatatg tctattactg ttgtaacatg gggactgaaa 123360
catttcagcc tgcaggagag ctccttaaga gcaggattta aacaaaaaaa acaaaaaaca 123420
aaaaaaaaca aaaaaaacaa agcttcagga agtccctgaa catgactaga tccactaggt 123480
cccttcctgc cagagtaagc aatacaagac gagggtccct ctcaaataaa ccaagctgca 123540
aagaagacca gaccagaggc ctggaagaca caaaaaccag ctgagcttac tggaagaggt 123600
```

atagaccaga gtcacttgta aaggacactc tccagtctat tgattgctct gatgcctgca 123660
ggctgtgcaa tatgctccag tttctcaggt tttgtgagtt gtcacccatg ttggggtagg 123720
ctttggtgat gcagctgtct ttgagtcatt tctgctcctg ttaagtatac ccttgagaga 123780
gacaaggagc caaaacaatg ccatgacaag ttcctgatag cttgccaggc agcgggcctc 123840
agtttccatt tactggatct gaacaagcag ttcttggaaa gacaactcat gggcaaccaa 123900
gctgtaagca ccccacaacc ttatgcatgc ttgaaatagc taaagatagc ttctcccacc 123960
ctgaccagta agccagccac caaccaatcc tatagcaatc cttaaacttt gtgtttaaat 124020
ccaccaatca gcactcaaga ctaacctcac ctccctggaa tcccctaatc ttacttaaaa 124080
ggagcctgcc aagcttctct tggggtcagc attttgccac ccttacatgc aggtattttt 124140
gctttcaaat taaatgatct tgatggttgc atatgtgttt ggtggtcgtt ttgtggtact 124200
tctcatagac actaacaccc ctcatccata ttcttgtaag taacccctat aaaactcatt 124260
ggttcaccaa gctgtacttt tggtggtatc tgtgctttgg tttgttgtgg actcttgtct 124320
ggagtgcgta gacatgtgtg ctgtgtctcc ccaagaaaat tttcgctata caacaattat 124380
tcaagttaca atttagaaaa gaatttccca attattcaag tataatgttt tatcattaat 124440
tattaattga tgctttttca ttggccttga tgatcataat gcctcaggct ctgagttgtt 124500
gtacaactct ctgctggttt acaccctcca cgaggagtat ctaagaaatt aaagttacta 124560
aaattagtaa ttaagatcaa cttgtatgat tccagtcctg aacaatttca ccaagcaggt 124620
gagttgaagt atcctcaccc ccaaagtcat gcacaaaaaa agaacaaaca aaaagaaagg 124680
agtgcaaata agtcaagtaa attgcatctc agcggatgaa tgtgttaata aagatttgag 124740
aaatatgaca ttttctgtga atgctcatga atgctcacag gtctgcaatt tatccaagtt 124800
cccagctcag tgaggaataa aaattattct agagacacac cccacccaaa caagtcaacc 124860
ttcatacaca atcacttgct ttaagtgtag attaattttt atagcatact ttcaataatg 124920
tttattttgt gacaaaggag agaaaacaca cgcaaactag aggcttctgg acttaatgtc 124980
cttatttaca atgacctatt ttatgtgagg aaaatgattt aatggcaggc attttaagac 125040
ttacaggaaa aaagcaattg ctttgctcat gatgtgcaga gccattattg attataaaca 125100
atgtggtaaa gaaaaaagca gaaaaagtct tctactaaat aacagagaaa cctcctcaat 125160
ttttgcttcc ctacactcaa atctgtgcct tctcattaag aggaaaaatt catatctctt 125220
tgaaaaagtt tcagaataag gctcactcac taaaacataa gcaatgtagt gttttatttc 125280
atgctggact taaactattt aaatagttgg tttaataata tatgctatat caaatatatt 125340
tgaattatca atctttctta attacaggat ttttctctaa cagtttccca ctaatagaac 125400
cttaaccatt agtataaatt agtgagcatt tattttaaca ggataaaaac taaaaataaa 125460
taaaaataag gtaaatgttg gtataatggc aatactgtac ctctgttgtc ctattcacca 125520
tcatctgaag cagtgttttg tgggaaaaag agggaagatg ttaaacaatg caagattaaa 125580
gaaacagtag atctgttcgc tgcaactgag tatgctattc caacaagaca gagtgagaaa 125640
agccagctcc atcccacaac agtcattctt gctgactctc tctaattaat ggagtaaaca 125700
ggaagtctaa ctaaatgtct caacatggaa actggtcttc tgaagaaatc atttagcctg 125760
aatttttgtc actgtctccc aacggatact ccccttccat ctgaaatacc catggaaatg 125820
aattatgtgt cttcctgtcc agaattctgc attatcagca gagagtggtc cttggtcatc 125880
acccaggaga atactgcagt cggaggggac ctctccacag acatatcagc tcttaccttg 125940
gattgcacgt cagcattatg atcattctga agcaggaggg cggcagactt ggtgtcatct 126000
ttccgagccg caatgtgcag agccggcagc ctcaccttcc ctttagtgtc attctccaag 126060
aggatggcca ctgcctggtt gtgtccctgc tggagtgcca ccgctagagg agtaaagcca 126120
tcctagaata taatttacat gagtgggtga gactgacaac atactccaat gacaccaaag 126180
atgggatttc ctgacagagc cttagagcat cagctattca tccctgcaat agtattattt 126240
gttacataat gaagtgggtg atactgacaa ccaggacagg aaaatcactg tgaggagcag 126300
aagcagaatg gactctgcat ttgccctatg gtgcaatggc ttcattagat ggctctcttg 126360
atttccattc tgtatcctaa caagcctgct gattacagga gtgggccaaa tgggtgtttg 126420
taagaggaaa ataaaaatta gaacgaacac ttagctataa cataaaggga aaagaataga 126480
aaccaaatct aactgggagt ggaaaatatg ataatctata gagaaaattg agtgtctaat 126540
caacaatgca agagggatga atgtttttc attgtctgag agaaggtaat aatgactgtg 126600
gatagagtga ttgaaatcat ttatgttacg atgcttcaga cttaatgact ttaagctgta 126660
aattagatta gccattaatt ttgcaattac ttgtatttta gattgctaag atcatttcag 126720
tataaatttg tatatgctag ataacattta aaacccaact tctcttgtca acatgagaca 126780
gagagagaga gagagagaga gagagagaga gagagagaga gctcaataaa tgacagcaca 126840
gacaatacaa agttagaatg atctccagaa tcagatagaa aaccatgcaa cagaatttgg 126900
aaagtcatct ttgcatcttc agaagcaaat tgtttagctc ttggaaagat ggaaagtgtg 126960
tcactcctta attccatgag gcttccaagc aaatgttaga agtcttcctc atacagcagt 127020
aatgagggtg gtaggttgta caattgaaga tgtcatttca gggttgagag taattcaccc 127080
aaatctaact actcaatttg ttttcaacat taattgctta agtggtaact gtggcctttt 127140
aaggaaaaat atttctcatg ctacatacat cataccatgt atgtagcatg aactgtagta 127200
atatgttgac tgctcttttg attaagtttg agttttaaat acagcaaaaa gagtggagga 127260
gtagagtgca gtacctcttt ttttgttttt gttttgtttt gttttgtttt tcgaggcaga 127320
gtttccctgt gggaaacagc agtcctggct gtccgagaac tcactttgta gaccaggctg 127380
actcaaactc actgagatcc gtctgcctct gccttttgag tgctgtggtt atgtatacac 127440
caccactgcc tggcctagag tacagtctct taaggtcgag aatagcaaac agctgcagta 127500
tatgggagtg ttaagaacgg ggtagtttat gaatgaagaa cacatccatt atcttgagca 127560
tatttggatt tatttttcct tgcattctgc agcagtctgt attaatggca tgtggacttt 127620
gtttttgttc tgttttgttt ttccttagag acacagccta caaaatagaa ccccagtaaa 127680
aggattgtag ccttaaattt tggcagaatt ctggaggaag gaaaggagaa gaactctatt 127740
taaaaaatgc tgctggccag acagggatct cccttcggag gtctaaaagc tggattccaa 127800
ccatgcagaa ttcattctca tctgtatttc atggaagaag gctaagaaaa tgtgtaacta 127860
tttgttaaaa tacctcaatg aactctgtag gggaacaaac agctaagttc agcagttttg 127920
atttcatcat ttatatacta attctcctta tgagaaattt aaaactaagt atttcttcat 127980
gtgcatatac ttccctgcca tgtggaagga ttttgtaatc acctgatttt tttctaatgt 128040
gggtatagca cttggttcat aattaacttt ttcacattat tgctacacat gagcacagaa 128100
gtgctcttta cgtgtatctc acatactcca atgacaccaa agatgggatt tcctgacaga 128160
gcattagagc atcagctatt catccctgca atagtattat ttgttacata atggtacagt 128220
taaaagggag tgtgcacggt ttgtccatgt gaaccctggt aactatcaga gtaggtggta 128280
tggttcagga tatcaagttt ataaattttc caatcttata agaatttgcc ttagttatgc 128340

```
aatgatattg ttttaaaatg aaatgtaagg catactcatg gctaggcttc aacccccatc 128400
ccactttgtt tcctttgaaa gtgttgtatt ttgttagata accagagttc tgcaggcagg 128460
ccactgtaca tcctggcctc tgctggtgca gtgatcacta agggctattt ttggaaatac 128520
actgcaatat aagatatttg aagcataaac tctatataac atatttttgt aacattctct 128580
ttatacgtac atacatacat ataatagtat ctgtgaaata tcttctctat cattcatttg 128640
ctcaattact tactgagtgc acgaactctc agaaaccaat tggcttgttt ctaatgtcaa 128700
atgctcttga caggagttgc catgatcaca gtcacacacc tgtgtcatga tttgcatttt 128760
gtcataaata acattgttgt gacacagtcc ttagaaaatt gtactaacac aaatagctgt 128820
aagttatttc tgatagtcag aaatttttcc ttcaaggagt tgctttgaat cttaaaataa 128880
aatattgaaa aaaagcaaca aggataacat aattctaatt caatctttga ctgctataaa 128940
ccccaaaatc aagtcaggtc acatcgacag aagtgcgatt ttgtggtgtg gattcctaaa 129000
accccaggag aactgcaaat ttagggctga tttaggctcc acctatagca agataaaaaa 129060
aatcaagctt aatggtgatg gaagtaagaa tgtctgatca tgatcatgaa tctaaaatga 129120
agttataagt tcatgatgat gtgcacaagc ccaagtaact cactggccat tacagtgggt 129180
tacaaaatag taatatgaac attcccagca tgctttagac aaaacagtgg agagcctttg 129240
caactagtat aatcaatatg gaccttaaaa caaaagaacc agaaactgag actcacctct 129300
gtagcagtgc tctgattagc tccattttct agcaaatatt ttacaacatc aatgtgattc 129360
tcctgggcag ccatatacaa aggagtgaag ccattctgag gacagacaac aaaaacagaa 129420
tctcaatcat ttgtaaagtt tcagcaaaac cgaagtgaca tcataaggag agaatcacac 129480
actatgaaat gatgcccatg taatagcttc tgtatttatc aattcataaa tgaagtaaac 129540
aatatgaact attcaaactg ctagagatat ttgaagcata aactctatat aacatatttt 129600
ataacattct ctttatacgt acatacatac atataatagt agctgtgaaa tatcttctct 129660
atcattcatt tgctcaatta cttactgagt gcagctaaca gtagctgaac catccctagg 129720
atatagtgat aagcaggaca aacacatgtg cccttgtgga atacacatca taataatatt 129780
cattattatg ttcttatcaa aaaactcaac agaaatgtta caccatgagt taaaaattaa 129840
gtttgttaca tctttttatc tctgtatgat taagaatata ccaaccttgt tgagggggaa 129900
aaacacattt tttaaaagct gtactcaaat cctcaaagca attgggcaat tcttatatca 129960
gattattaaa gacagatgtt tacactttcc ttatattaat gagaatgagt aaaagtaaga 130020
tgaacacttg gagattatta accaaaccca gagagtagca aaaataggtt ttaaactact 130080
ttgttgaaat gaaattcttt tgcatgcact gtaaaagtgg aaacattatt caaagtgacc 130140
aataaccagc aaaatataaa tacaaattat gcaagtacaa taagtaaaga aatttaaatt 130200
ttgtttaaga aataaaatat acagggtcca aatagtgaaa ataattttaa tctaaaatag 130260
aaatcatcta agaagaataa attaacaata gtgttatgat ttgtgaataa ctactgctag 130320
ctggagagta tattttccaa ggcttatcaa gcaggtgaaa tacgttgtat tttaagaaca 130380
ctgaaggggt ggcggaagga tggaattaga tatttgaagg aagggaaagc caaggaagac 130440
tgttcaaaac aatgagtggg tgtggaatga ggatctttcg agacaagaaa gaggtagtga 130500
tgcagtaaga gaaaaagaac tttaacagag cacagacatt gctaacaatt ttcctctgat 130560
aaaattctct aggtagatca aaatgtcttc tgtatttatc agttcacaga ccatttcagc 130620
aaaccactat tgtccggaat gcatacaact tactcagcat tcttactgct tcagattatt 130680
```

```
aggtctaaca tatgaggcta ggagggacca tacacctgag tgaaaacaaa aaggttcaac 130740
agaaccagga gcccaatatc tccttcatgt ccaaactatg gtgcagatga cctgaccaca 130800
agactctacc tagtgttccc aagtacagtg ccagtccttg ctcagactct gtggtcgtct 130860
gttgtaggat attcctttac cctgcgtaaa gatgtgtcac tgtaattggt ttaatagaga 130920
ccagaatggc cattagcaag gcaggaagaa gcacagatga ggacttgtgg acagagagag 130980
ctctgagaaa aagaaaggcg gagtcaccag caaacacaga ataaccagaa tgagcataat 131040
ggagataaga taacaagctc atggaagaac acagattaaa atttatgggt taatttaagt 131100
tattagagct aattagaagc cagcataagc taagaccaag ctttcttaag taatgtaagt 131160
ctcttgtcat ttttgtgagt gggcagccca aagaaaagcc caactgcagt tgtcctctca 131220
tacatccttt ggccagcaga gtgatggtct tacatatatc catatctttc tgtagtattt 131280
atttcttgct gaccaaatac atgacgaaat aacttaagag agaaatgttt attagggttc 131340
aggatttttg gggaatttca tccaaccatg atgggaaaaa catggcagca cgagcagtca 131400
tgtcgaaggc agtgggagta tgaggtattg ggggttggca tgcctgtgga ccaggaagga 131460
gaaagaaagc tgcttcacaa ccagggggcag ggataacttc acagatctgc ccctagcact 131520
ccacttcttt cacataaagg tacttcctaa ggactctata aaagagtgtc acaacagagc 131580
agcaagtttt caaaatatga ccctttgggg tacactgcag attgaaatca tgacatcatt 131640
ctagtcactg ggatctgtaa attgtacaga ataggaatag aataaatgaa taggaaactg 131700
tccatcttca ctcaaatatt gcttaacaca gcattcctgg tctcctcata catatgtaaa 131760
agtactatta aatatatcat gttcctatgg ttttttacaa gggtttaaat ggaaaccatt 131820
aggaaaacat atataatttc tccttgctga tataaaaaaa ggttttggct tgagcctgaa 131880
agcaacctag atgccactca actaatgaat ggataaagaa aatgtggttc atatacacaa 131940
tggagtatta ttcagtggta aaaacaaatg acatattgaa atttgcaggc aaatggatgg 132000
aactagaaga aaccatcctg agtgatgtaa cccagtcaca gaaagacaaa tacagtatgt 132060
actcactcat aagtggatat tagacataaa acaaaggata accagccgat agtccataac 132120
tccagagaag ctaggaaaca aggaggaccc taagagagac atacatggac cccaaagaag 132180
gggaaaggga catgatctcc tgagtaaatt ggaagcatgg gggaggaagg aaggagcgaa 132240
gttggagaaa gaaaagggag gagggggagg ggaggagagc ttgaggaatc gggaaggtgg 132300
agctggggga agaacaaaga agaagagcaa ggaaagtgat accttggtag agggagtctt 132360
tatgggctta gcaagaaacc tggcactagg gaaattccca ggaatccaca aggatgaccc 132420
caactaagct aagcaatagt gaagaagcta ccttaaatgc ccttttccct ccaaacagat 132480
tgatgactac cttaatccag tagcagaagc agagattcac agctaagcac tgggccaaac 132540
tcccggaatc cagttgtaga gagggaggag tgatgagcaa aggggtcaag accacgctga 132600
ggaaacccac agaaacagcg gacttgagca agtgggagca cggggactcc agactgacag 132660
ctggggaacc tgcataagac caaaccaggc cctctcaaca tggctgtcag ttgagggact 132720
tgggcagtct ataggtccac tgacagcgga atcagtattt atccctagca catgaactga 132780
ctttttggag ctcattcccc atggagggat actctttcag cctagataca gggcagggcg 132840
gggggtgggg gggcgctcag tcctgcccca agtgatatga cagacttcga tgattccccc 132900
atgggaggcc tcaccctctc tgaggaatgg ctggggaagt ggggagatgc tatgaggaat 132960
gggagggcaa aagggagagg gaactgggat tggtatctat ttacaataat aattaaagca 133020
attttaaaag aaaaatattt atcaactgga aataaaagat tttggcttat cctaggtgca 133080
```

agcaaggaga gtagtataca ataattctgg aataatgtgt tcatatccct agactacaaa 133140
tggtttcaac catattattt actaatcatt gttcatgctt ctcagattag ttataactgt 133200
ctttcagacc cagaaatcat gctcaacttt ggagaattca acatcaaata ggaccctcat 133260
ctagaagctg tagaaaagcc tcacacaggg atgagcaatg ggtagagtgc ttgctgtgtg 133320
agcatgagga cctcagttca catccccagc agtgatgcaa atgtggggcc cacctgtgtg 133380
cttctgctta ttaaatacta tatacagtac ctctgtctac aggaaaatat caattatcta 133440
tcattcattt atatttattt agccaaaaca aaaatgtgct tggtagatag gtactgtcta 133500
acattgtact cagagagtga ctctgagaca aacacaaaaa ctctttgaca cacccagcac 133560
agtcaggtta gtaaagaggg actaaagaac agacagacac atagaaacgc ttacagaaga 133620
gtggcaatca tctggttcat gcttgctctg atggagcagc accacctaca ccagcaaccc 133680
agaatctctg tgggtttttg atgtacactc aatatccaca cacagaccag aggaaggctt 133740
tacctactcc cttatcctgg cctgaggaag gctttaccaa ctcccatggg tctaagtcac 133800
agtactggcc cttgataata gtatgcattc actgggaatt catctacctc ttacaccttc 133860
actcaaggtt tcctctgctc tccacacact ttccatagga acacccagtc caaagctcag 133920
ataaccaagc ttaaactatt ctagacagat tgggggacac acctaactac tctttttta 133980 ttacatgtta tataaggaga atacagatga aggacacaga actcaatggt gtgagaaaca 134040
ttctgccagc aggatgtcac tagagtgact cagtgtaaag agtagggaaa ccacggaagt 134100
gcagaagcag aaaaagcttt ttagatggag ttgagaaaag agaggacaaa cgggtcttag 134160
gcatcactca gtgacagatg gtgaggggat tgggttcacc aggacttagc cctatctgcc 134220
tcactaagga cttggggctt tgttttaaat ggcttgagag tcatttgggt ttttcaaatg 134280
gggatttggt gtgaatacat ctgaatttta ggagattagg ttgccaagaa tagagaggaa 134340
gaaatgtaaa acactctgac tatagttact gagaatgaac agaaggtttc tgtaacaatc 134400
ttgatgagag ttgaaaaggg aaactattga gataatttgt tttaatcaaa gataagctat 134460
tattgagaca tttatactac acttggtgac tagaaggagt acaagtggtt ttaatccata 134520
tatttattag tcaatttgaa tagttcttaa ttagttataa ctcttttcca gatccagaaa 134580
tcatgctgag ctttggggac tccaaatatc aagtaggact cgcatcaaaa atattttatg 134640
cttataaaaa tgccttgcac agggatgggc agatggctca gtgtagtaaa gagcttgctg 134700
tgtgagcttg agaacctgag ttcagatcct cagcagtgat ataaaagtga ggttcaccct 134760
aggtgtgggc agagacagac agatccttgg accccaccag tcagtcagtc tagccagggg 134820
agagatctgt gttcagtgag agaccctgtc tcaaatatca tgatgattat gatgaggagg 134880
agatcaatag atgaagacac caatgtccac ctctgggccc aaacacatgt acatattccc 134940
acccacaatg cttagcccac agcaggaata aaattaacaa tctgaattgt ttttatgtct 135000
gtgatagttt caatttatct ctaaattatt ctcaaacaca taagtctggt cccttgtttt 135060
taaatgcaga atgtcttaat agtttgctct taaagcatca gttatagagg gtttgatggt 135120
gggtggcttc taagtctagt gattaaaagt tgttgctctc tagctttaca ccctctttta 135180
ggtcaccttc tttagggaga aggaatcttt gtcatgatat cattcaagca gccacatgag 135240
agccatggga gaaggaaatg aaatttccca ccagggctat cttgctaacc atttgaaaag 135300
tacccagaga ctatgtgctc tacacaagaa attccttcag tgactgtggc tctgggggtc 135360
ctcactatga cctcatgagg gacactgaag cacaactagc caagctaagg ccctgatcag 135420
aaactgtgac aataacacat gtatgttgtt tgaagttgct aagtttagtt agaaaactat 135480
ttagtgccaa tgtttaataa gcacaaaacc cagtgagaga tgccccccaca tgctcagacc 135540
tgtatctctc ttgccagtta tacatgcctc ttgcctttct tacttcatag tccttccttt 135600
ctaccgagga aggaaattat ctaaaacagt taccttcaaa tgttttagac atgtaattct 135660
tcaaatgcta aaaataaaaa tctaaacaca ctgttcttct tgaggatgaa tgatgtataa 135720
gtggccctca gtgttcatca atcccctaac aaccaggaaa atggtactta actgtgctgg 135780
attccaaaaa ggcacatgag ggatacttcc tgtagaatcc tgggacctgg gttacctatg 135840
agttaaagca ctatgaccca acagccattg tatcctgtga ctatctattg aagtcagaaa 135900
agactagacc tctgcattga taagaaagaa tatatgaaac agatgactac tgtttatttg 135960
tctaggtcaa accacacata gtctgaagca gtattaaaaa aaaatttcaa tgtaatcttt 136020
gggttttctt acaggaagac tcagtgaata aatcttataa ccatacgtaa taatagaaaa 136080
tgagaatgga cacatatagt ctggagatag taagagtcaa atctcccctc tgaagaagtc 136140
acctgtcatt tttaagaagg ttaatgtcaa gactgagggt ttggttgtac tttttgcacg 136200
gggcagaatt cttcagcagc ccgacagtcg agcggttgac ccacattagg accaattggt 136260
tgttactact gtggtcatca ttctcactgc ctcacacatt cttcttctat taaagcagct 136320
tatgagatgg ggtaggaaag agtcctaaaa ttatcagcaa gcttgaaggt caggatgatt 136380
caaaccctgt ccctaaatac accatgaaca cccagctgtg aaggatggag gaaaccaatc 136440
tggactaatt gtagccatga aaataaagca gatgttggat attctggggg tgtgcttagg 136500
gaacaagaag gaaaaatagg attgtaaaat agtaaagctc aactgctctc ctgtctcatc 136560
ttctagattc aaatgactta cagatgcctg aagtcaatca cctcaggaca ttatctagga 136620
gaaagtggct tcgaatttgt acaacacagt gagcacctct ctcaaccaaa ttcgggattc 136680
ttcttttaga gaattgggac agaggaacaa cattgtctct tcttctaaac tatagccaac 136740
agatgtgtag ccgccatcat aggtctccag tgaaatacag tccagaataa atcagatgtt 136800
acagaaacca caggagcaac agagaaagac tctgagcctt tggttatgga ggaatcattt 136860
gatggtgggg ctatcctgaa gctcaccaac ctatctaaat tttattcaag aaggtcaaga 136920
aagttttctt tttcttttt tattcaagga caaggtgatc tattttctta tttgcaaatg 136980
gaaacatcct aattagtatg gcatctaaac aaaaatgcag ttttcaatat caccattagt 137040
ttaaaattaa acaccctagc ctggatatat ggctccgcaa ttaaagagca ctttttgcta 137100
ttcaagagga cctatgtttc atatgcagcc tccacatggt ggctcacagc catctgtaat 137160
ctctagttcc aggggatcca gttctcactt ctggactcta agagtaccag acatttacat 137220
agtgcataga catacatgag tatagcaaaa tacccataca cataaaatga aaataaatat 137280
ctctattttt taagtaaaat aaagcactct acccaggaaa tttgaagaat acataaagtg 137340
caataaatca gctgtgcaag caatgaaatt ttattattat tatttctttt agtttttgag 137400
atcaaaatat aattacatca tttttgcctt tcctatccac cctccaaact atcctatgta 137460
gtcctcctcc tttttccaat caaattcata gtccttttca ttaattgtta tgtgtgtgca 137520
catttatata ttttttccta aatacataat gacaacttgc tcagtcttta atgttacata 137580
tgttttcaag actgatgatt tggtaatgga taaccaattg gtgtgctgct tcctggggaa 137640
gactattctc ctcatagtat cccttagttg cctgtacaaa acctggaaag ttcaaagggg 137700
ccattgcagg agtaggggaa caacagagag gacaattgca gggtacaagt actctgaatg 137760
gggaaatgga aaaaaatagg aggctctaat tagggtaagg agggagataa aaaaaaaaag 137820

```
aagggagaag ggtaaaacaa cagtaaggaa gcctgggaaa gtcatgaaga atcacactat 137880
taactatcta tctaaaagta cctataatat acatagcatt tcatataaat atatgtatat 137940
agtttaatgc ttgtatttat aaacaaatat tattatatat aaatatacat atatagtgaa 138000
agtttcccat ctgtcctgga aatgctttct ccaagaacca agaaagacca cctaacaaaa 138060
gccaatacca gacattgaaa gccctctttt gagttgttgg gcctagctgt ccaagagact 138120
cccagaacat tacaggctat tgctattgcc cttggtttct ccacagagat gaaaggtaag 138180
tattgctgaa gacaccatgc acttcagaca cagggtcccg aggcccctga gctggaacta 138240
acatgaaagc ctcctaactg aggactagct ctaatgatac cagaaggagc catgaaagct 138300
tccaaaagag tgaagcaata atcggttcta ctagctatga tgtcaatacc gcagcaacaa 138360
ccatcatgtc aggataccct taagagtgca gtagaggcac tcataccttg acagacacca 138420
aaagcttttt aaatgaactc aagacacact caacaagaag gaaatcaaat tcctggtact 138480
tgaaacctag ccaactacca aaaactagaa aagtcacaga tcttggcaga cccccaaaga 138540
atcaaagagt aaaagagaaa aaacaaacaa acaacacata cacactgagt aaatttcttt 138600
aaagaaatgt tacattcatc gtggagtaaa ttcctctcct gatatctcat tcatctttat 138660
aaccacatgt ataaattctt ttgtaatgtg tatagaatga gtagttttaa agatagaaac 138720
tagaattata tcttgcagat gttgaaacct gagaaacaat tagaggagta atgaaaatgt 138780
ttgcgcagga gaaataaaat attttaataa agttactaaa tatttgaata ttgaaactga 138840
atggtcattt atcccctggc acattttctg gatttccaaa taaacattat agattataag 138900
atacaggttt tttgttttgt tttgttttgg gtttgtttgg ttgattggtt ttgcaagcag 138960
tgtgctctgc ctggcactgt aacaagagct ttaatatatc tgtttttgag cgacatcata 139020
cgtgacccag taacttatac aagaaagtat gttacattca aaaagcaaaa tattgactgt 139080
tcttcatatg aaatgagaga tttagtcaac agcaaccact gtaggatact ttaatttctc 139140
ctaccagaac aaaaatccca ttagcctgga gtccttatct tgaattaaat gactatgcta 139200
atttcatcag ttatcacttt caggacaacg agctcagatt agcatgggaa gtagcaaggc 139260
tgacccatgt tatttatgat aactgtagag catgctgcag ccttccagac acaggctgtt 139320
tcattccaag gaggaggtac ttacagcaac ctcttccttt agaaagtgct ttatttactc 139380
aaaataaaaa ataaatctgg atacatagaa tcctcaatcc cactataaaa gctacagttt 139440
ggacccaaag tctaaggaat tatattcacc ttcaaagttc atccatgaaa ggatattttt 139500
atatcttttc ctaaatagtc agaatttaaa gtctaacaaa aatctatttt gattgtcctg 139560
ccactagcca aagaagttca gggggagatt cctaacagac actcaaaata ggacatacag 139620
aaaaataatg ataatggtca actcagacag tagtgtcctg tcccgaagga ccaggtcaga 139680
gccacagaac tgtgtcaaac cagcttgagg actttctgtc aagggaacag agagcattgt 139740
cacccttct cctagagaat ttttaacttt aaggttctta aactcctata catattcttg 139800
catctcatac atctaattat aacaaaagga attcaaggta aaatgggctt ccaagaaaag 139860
catgccctgt tcctgagagg gatggaagga ataacacagc cagaaaagat agggtcctgc 139920
ctgctagaat gtggttgctg ctgcttggct cagcctactc tttttctgaa gagtcttttc 139980
aaattcttct tttgggaagc acaaaaaata aataaataaa caaacaaaaa acaagaatgc 140040
tccggaggag aaaaccagaa gaaactagtg attttccata acactgccta gatgtaccaa 140100
tttcaaaatg tagctgcccc cagacacaga cacacacaca cacacacaca cacacacaca 140160
```

cacacacact aatatattta gatatatttt ctggaacatg accatctaaa tcaatagttg 140220
tcaaagccaa tgagatggta attattacgc ttatacagga ccagttgttc acaaggcatt 140280
gccattgttg ttttgcaggg ctttcatcat ggactatgta aataccacgc acaccagttc 140340
tcctaaggaa tgactctgtt ttgatgtaag cacttccaca aagtcaatag ttggaatttg 140400
atctgttaat aaataattct ttcctgtccc aatggcatca acagtgcacg tgctctcttg 140460
ggaaaaacat tcagtgtctg agatagtggc agaatcctgc aacacagcca cagacagatt 140520
ctgccacaga accgggggt gggggggtag acaataagaa atgattttca gagatttaca 140580
gcatttaagt cattttctca ataaactaac agattatgaa gattaataat aattaccaga 140640
aataattaga aataattacc agaaaatgtt tgcgtatcac atgaggaggt atagggattg 140700
ggattaagaa ttgaaacgta tctagatttt ttttctgggc taataattga gagggaaaaa 140760
aaggagggaa aggattttcc tccataagga acccttgatt tacatttaaa tgtacattca 140820
tgtggaagag accaggaatg tctttactcc cattgccaca cataagcagt ttggctccat 140880
acatacgagg attaaaaact atgtgaccag atcataaaac aaatatatat ggcttgaaaa 140940
taggaggggg gccaggcggt ggtggcgcac gcctttaatc ccagcactcg ggaggcagag 141000
gcaggcgatc tctgtgagtt cgagaccagt ctggactaca agagctagtt ccaggatagg 141060
ttccaaagct atacagggag accctgtctc aaaaaaacaa aaagaaacag gaaaaaaaga 141120
aagatagaaa gaaaagaaaa agggaaagga aaccatacct gctgcaaaga catggccagg 141180
aggggggcca tagaggaagt aagtggagca acagaagaag ggagggcaat ggggtgaata 141240
tgagcaaaat gcaagatgaa atcatgtgtg aagatgtcat aatgaaaccc attattttgt 141300
gtgataattt tttaaatcat gataatattt aacaaataaa aacacaggtc ttgataaagt 141360
gatagaaaat ttaaaaatta gttattagcg gtaacaaaat aaaaagttag catttgggga 141420
cttgttggtt taattaataa aggggctaga gagattgtct ggtggaagag aatttgctat 141480
gcatgaaaat gaaggctagg ttcaaatctt caataactat gcataaagct gggtattgct 141540
gtacatatac ctgtgaccca gtactgtagg ggctggggac aggaaggtta ttagtgctac 141600
ctatctatca gccaggttta ataagagacc ctctctcaag agaatacagt aaagaatggc 141660
acagaaggac acctactgct ccccactaat ttccacatgt acagaagttc acacacccac 141720
atgtatggca tacatgcaca catactaaca cacacacaca cacacagaga gagagagaga 141780
gagacagaga gagagacaga gagagagaga gaaggaagga aggagagaac taaaataaaa 141840
taaaaattta ataaacagag attgtgtgtt gttcttcaat agtgcaatgg ttctgggcac 141900
ctggtgcaca cagtgcagtg tgttcaaact ctctacctgt ttctaacaag cctttttttcc 141960
ccctacagct tatgacccct gtttccaagc tgttatggca aggaaagttc cacactccca 142020
attactaaaa atgaacttct aaagagcttt gtccatctta ccccagaaaa gaacaatctt 142080
ttaacttcaa aggacaatta gtaaaaaatt acagatggca ttgtctacaa ccccaagccg 142140
ctgattatct cttttcaata atggagatag ataacatgac atgcctaata attagacctg 142200
cagacttcat ttattctata tttactgtgg gccaggactt tgcatctatc tcacatttgt 142260
agcaactcta cataataagt attactccca tagattagag gtgagataca gagctaagga 142320
gaggttaagt taacaggctc aacctcagaa tacaagcagg tgaaaccgag gttctcagct 142380
ggtggaccac aggcacttgc gtggagtctc catctctagt gccacactcc tggaatttgc 142440
cttgccactg tgtttctctc ccctttgtga ggttacgttt agctattctc tgaaaaatgc 142500
accccactcc ctttgatgct gtggttgtgc atgtgtttct ttccgttctt gtctctgctg 142560
gagataaacc ataacagctc atgcctgcta gcctagtact ctccctctga gctacacatt 142620
atggctaatt acttacccag gcattctatt ttacttgaac caagggttta tgctttaaaa 142680
gattgacttg tttcatcact ttcattaaac agttctttta tcattcctta ttatctggat 142740
aaaatcttga caggggcctt ctttaaatct tcaaaaagga gcctcacttg ggtgtaccac 142800
tgtttaaaat tcaaattcct ggtgcccaat acaataaaaa ataaatcttc ctactatgaa 142860
atagaaagga attctgttta ggtccaacca attgggttat tctattgata taataaatta 142920
aaggctttgg gaacactgtg gcacacccag ccttgtgctc ttcctggaat gaaattggct 142980
ccactgtctc ttgctactga tagtgaaaag ttttgaatta attcttttta tccaaatcat 143040
acataatcag tgtccaatga taagagtcat tgtattttta acagtctaat gctataattg 143100
gtaaagggca ggtaagtgta aagttcaggt tcatgaagac ataccttacc aggggactca 143160
tgttcaaaac caggacataa agaaacaaat actacttagg aacagttagg gatcttgtaa 143220
cctaagagac ctcaaaagct gtattccctg gttaagagtc atcaaagtgt cccatagtac 143280
agttagccag gattagaaca atactaaaca atgcccatgt ttttgtcaat gtacagaaga 143340
ctggcaatgt tacaaaatag ttcttgttag ccttccagtt tctttccact tctaaaagaa 143400
agaaggaagg aagaaaggaa ggaaggaagg aaggaaggaa ggaaggaagg aagaagggag 143460
ggagggaggg atggaaggag aaagggatgg aagaatggat ggagggaggg agggaagttt 143520
ggttttgatt ggttaaaata tctatttttt ttccaagaca gggtttttct atgttggcct 143580
ggctgtcctg gaacttgatg tgtagaccag gttggccttg aactcagaga tcagcctgtc 143640
tcagcctccc aagtgctagg tttaaaggca tatgccatca ccacctggcc taaaatatct 143700
attttaactt tagggaaatg attgttttaa ctttagggga aatatgttta ttatatgtcc 143760
atgtaaatgt tatataaaag tcagagggag gaaaactaaa gcagaatgag actcagattg 143820
gtttggttag gaacactggg atgacccagg catttctcct ttaaaacaga caattggctt 143880
tactaagcca gggtgtctga acactacttc cctggcctct ctgcctcacc tttattagat 143940
cctagggatg agcctttata ggacatcaga acataaagca atatttgacc ttgttgtgcc 144000
caaaatgtga tgcctgaccg actggagaaa ctgtaaagta agattcctcg gcacctacca 144060
ccccataaaa gccacacctg gattaaagat gctatgaaac caaatgaata gttagatcct 144120
ttaattgtgt gatattagaa tactgtagat caagagacaa attatatggg gctatcttta 144180
tttcgctatc aagtgaagta ttgaaaatta attctgagca agctactagc ttccaccaac 144240
tgagaaccta gggatgacac caagtctgtt tcattaaaat gcatatatac ctgcaggcag 144300
aactagatgg aatcagctga gtattaaatt ttacaaataa taataatatg aataatagca 144360
cttgaaatgg gcggggaaag cagtggtgga catagggaag aactagaggg gaagcaacag 144420
gggccgggtg gatcaaagca ttatttgtat gaacaaagat taagcaagta tttttaaaat 144480
aaaattaatg aactatagaa atgatccatt cttctgtaag gcaaaggaca cagtcagcta 144540
gacaaaacgg cagcccacag actgggaaaa gatattcacc aaccccacat ctgacagagg 144600
gctaatttcc aaaatataca aagaactcaa aaagctagtc tccaaaacac caaacaatcc 144660
aattaaaaag tggggtacag aactaaatag acaattctca atagaggaat ctaaaatggc 144720
tgaaagtcac ataagcaagc actctacatc cttagccatc agggaaatgc aaataaaaac 144780
aactctgaga taccatttta cacctgtcag aatggctaaa atcaaaaaca ccaatgacag 144840
tttgtgctgg gtaggatggg aagaaagggg aacactcctc cactgttggt gggagtgcca 144900

-continued acttgcacag ccactttaga aatcagtatg gtggttcctc aggaaaatgg gaatcagtct 144960
accacaagat ccagcaattc cacttttagg tatatatcca aaagaagcac attcatgcaa 145020
gaaggacatc tgttcaacaa cgttcatagc aacattattt gtaatagcca gaacctggaa 145080
gcaacctaga taccccctcaa ctgaagaatg gatagagaaa atgtgataca tagatttaca 145140
caatggagta ctactcagct ggggggggaaa agccaggggg ggggtcttga aatttgcagg 145200
caaatggatg gaactagaag aaaccattct gagtgaggta acccagtcac aagaagacaa 145260
aaatggtatg tactcattca tatatggatt ttagacatag agcaaaggag taccagccta 145320
aaatccacac ggccagagaa gctaggaaac aaggagggcc taagagaaaa atacatggtc 145380
tcccggagaa ggggaaaggg acaagatcta ctgaactaat tggagcatgg agggagggga 145440
gagggagata ggagaatgag agggggatga ggagggcagg agggagcagg aaggttgagt 145500
caggggaaga atagaggaga gcaagataag agataccata atagagagag agattatagg 145560
tttaaagaga aatcaggcac tagggaaatg tctggagatc tacaaagatg acaccaacta 145620
acaatctaat caacagagga gaggctacct taaatgccct cccctgataa tgaggttgat 145680
gattgactta tataccatcc tagagccttc atccagtaac tgatggaagc agaggcagac 145740
acccacagca aaacactgag gggaactctg gaatccagtt gcacagagga aggagtgatg 145800
agcaaagagg tcaagactag gctgaagaat cccacggaaa tagctgacct gaacaagggg 145860
gagctcatgg accccagact gatagctgag acactagtat aggactgttc cagactccct 145920
gatagagaat gtcagtttgg aggtctgggc aatctatgag gaccctggca gtggatcagt 145980
atttatccct atgatacaaa tggactttgg aagccctccc cacatggagg gatactctct 146040
cagcctagac acactggaga gagtctagac cctgctccaa attatatgac agactttgaa 146100
gattccccca tggaagacca caccctccct ggggagcaga aaggggttgg gataagggat 146160
ggggggtcag gggaggacgg gaggaaaagg gaattggaat tgccatgtaa gagaagcttg 146220
tttctaattt taaaaaaatt aaaaaaattc aaagtcaaca aagcaccata caggaaacag 146280
atatcttgtg tatttcccat ctttacatat actactttac tctctcttta aagattttac 146340
tattttaaac tatttttatc tatgacgttc tatatccatt ttcttttctt tttttttcag 146400
tatctaagca aatttttaaa catactgtac ttttttacaa gttttctgtg tctggaccca 146460
gctttactaa gtgcctgcag aattctctga ctgcatgagg taaatcttaa attgtcatgt 146520
cagctgcaat gtggcccagc ttagcgcatg gcactggcac atggcattga cagctgattc 146580
cagaggcagt tgtccatagc tgcacctctg tctgctgcct agcaccagct gacagagaga 146640
ctaaaggtct aggcatccat atccacctcc ttgtccaaaa cttttctgag ctttctcaga 146700
ctctatgttt ggatattcaa gccccacatt aggtgccata cacagttaaa ttttctatgg 146760
gccaccagct ctctcccaga taatgacaca gtgactgctt attaattatg aaagctcagc 146820
ctatagctta gggttgtgcc taactagctc ttataactta ttaacctatg tttatgttat 146880
taacctatgt ttaatcatgt ggtgttactt ctccccccatc ttgcacctcc tgtttcctct 146940
atgtgtctcc tggcatctcc tgtgcaccta cattcctcct cctcttcctt tgtctaccca 147000
gaaatcccac ctatacctcc tgcctagcta ttgaccatgt agctttttat tacacaatca 147060
cagcaacaca ccttcacaca acacacaaat atccccaaac acccatctgt gaaccacctt 147120
ggaaaatcca gttttaccaa agacccctgt aaaccattcc agttgaaact cccatctttg 147180
atatctcatc tcactcagta aacaaagagg ttattcaccc accatatccc cacactttgg 147240
aggccctggc ttccttcagg aagaagcatg ctagtcagtt tagccaacct gtcctccaca 147300

```
catgatgttc ctacttagta attatacatc tacaaaccac atactccttg actgtaaatt 147360
ctcacttgtc aactgattta ttcagagtca agccatttct ctcttccgtt atagaactgc 147420
attgctgcaa tccccaagag ttttctttac catccattac cataatgcac atggaggtgt 147480
catgggaacc ccagtttaca tgattaatgc agaaaatccc acaaatgcat acttctccat 147540
aacttaaaac ctgcaggaat ttaccaaata tcgattactt ggagcttgtt tcccttcata 147600
tttcaaaagt aattttatta atctactttc aaagaattca gatgtttgtc tcctgaatat 147660
cagactgctc ttcatttctg tattttggat taagttttta gaaagatata gaaaagagta 147720
gaattttaat ataaaattta ggatttgtgc tatgaatctt gcatttctac atctttttca 147780
tggttcttaa aaggaaagag tggttctatt tccctgagta tgccctccaa ttcatctaac 147840
accaaatgct ggatacataa atgccaagag taaaacagga atgggggggg agtgaaggag 147900
ggttcctatc agcatctatc agcttaaacc aatatctttt caaatttgct aagaggcatc 147960
agcaagatag ttagcttgcc tgtataaaca tctattttta aatcaaaatc tgagtcaact 148020
gataatggca cccatctaaa ttcatcaacg catcaacctt attgaatgac tgaggcattt 148080
agaaaaacaa ctttaaattt gattaagtgt tcccactcat aaattttctt acagtataat 148140
aaaaccattt gaaactattt accaggattc cctgccatgt gactcttaca ctgagttaac 148200
agtgtgctgt gcaaataagg attattttaa tctcacagtg atgacatcaa ttttccccta 148260
agatatgtta taagatgata tgattagggc cagaaagaaa agcttcaggg aatctgaaaa 148320
caaatgaatg atgaaatggt tttagcttat tatccttgag ttgtctccaa agcatataaa 148380
ccaccatgta ataactaata tcagagcttc taacaagcat ttactttgca acatttgcca 148440
catgtcaacg tctatcacat cactgggctc aatgaatcct ttggagaaat acaacactgt 148500
tctttttata aactgaaatg tgagcatcgc aggttagtgt cctgtcatcc taagggaacc 148560
ccccatcgcc tgttcaaaca caatttgctt tcagctccat gttttctaca tccactactg 148620
attgagacac agtctgggct acatgacaca cagggcttct cttgtgccct ctgaagcaag 148680
tgtggctgcc agactggcag cccttacatc atctgaggaa tttctactcc agagcaccca 148740
gaaacatatt tagaaagctc tgcaggtgac cacaattcag gagaatgttt gatacctcct 148800
gctctagagt aaaagcatgt tatattgcta taaacaaaat tgtctttcag ggctacggaa 148860
agagcgcaga gctgcctgcc tgcaggacaa ctgtttagcc actaacgtga cacccctgga 148920
tcacacccaa aagttgtatt ggagtagtaa aattttatag caccctgtgt ttccaagcct 148980
aagatgctac tgtacctaat ggaaaacatt gatgcttttt acaatggtac caatctttat 149040
ttaaaaaaaa aattgttaaa gttttacact aaagtatgtt tcaattctta tcaaaacatt 149100
gatgcaaaat tagctgaaaa tttgagttgc aagcaaaact gaaagtgatt aactaaaact 149160
tcataccatt acacagccaa aactggatgc cttatctgtc ataaatagat ttattaatct 149220
ctataatcaa aatgaaagaa cactaagctg attcaattat ttttttagt gtttcctagt 149280
ctggaatgtg tgtcatctat acattcatat ctcttagaca tgatgaggaa tgaataacac 149340
agggaataga tcctgctaca caaaggcaag ccactgggga tgtcccagag aatggattaa 149400
aatgagctag ctatatcttc tatagtaacc cagtgtggtt agcatgctaa aaagaaagcc 149460
tggggggaaa aatgcttgtt ttgtttgttt gtttgtttgt ttattgtttt taatgtagta 149520
tcaaccccag ggcttcccat ttgtgaaagg aataaatttt attagaaaaa tacacagtaa 149580
ttcctacaca gagatgtcat aaataccaag agtaaagtgg ggagcaaaat atcatgcatt 149640
```

```
ttttctatca aaaaataaag aaatcaggtt tattgtgcta ttcatattgt ttctttttc 149700
ttaatttcaa taggatgata acttcctttt tatgatttaa tatatacatc ataaatgcag 149760
gattataatc tgccagtttt actcagtatt ttaataaagc cacagttggg taactaaaca 149820
aagtataggg agtcctgtat tattatagca gagccctccc atttggaatg ctggcttttt 149880
tataaagttt taaattttta ggaagaacag ccatcacata gcagcacaga gcgtccatga 149940
accacgtttc atggatatca ctgccatcgg ttcctcttct ctttgaaggt catcagacaa 150000
tgatgaacta gcatttacca agtgtttgaa aataagaaac taaaatacat gatttcgtag 150060
aatgctttgg ataaaataag taaaagaatt ttgggggaaa agtaaacaca ctatatcaat 150120
atgacaaaag catcctataa acttactcag agcagagaaa acccaaatgt gattaatacc 150180
tgtgactgtg cgttgatatt ggctccttct ttaactagaa ctttgacaac ttccgcttgt 150240
ccggccagtg atgcaatgtg aagagcagta tttcccttct gttttgataa aacagaaaga 150300
ataaaaaaca ttacagtttt ccaaattgtg tagaaaccaa catgtacaag aattttcaag 150360
ttcattcata gttcaaatta ttaaaatctg gtattttgtc aaggtaaaca ttcactttta 150420
tcaagcccac ctcgtaaagg atttgctgac atctaaaagt tggtaatctc ctgcagcatc 150480
tcacttcact gtcttttgta atacttagta ccatgatggg aacatcagag gactagatgt 150540
taacaaaacc acagcttgtg gacatgtgtg catgtgacag tccctgtaga attcaaggga 150600
tttgggggtg gggaatagta ctattgaaaa aaataccaat gtccttgaaa cattgcttat 150660
ttaactgtgc aaaagtaagt agggaggctg aagaaatggc tccatagtta acagcatatg 150720
cacacagacc ccatcaccca cattaggttg tttacaacca ctgtaatcgc agctccacat 150780
attggatgtc ctgttctgtc cccctcaggc acctgtacat atgtgcagat atgcacaaga 150840
tgcacgcgca cacacacaca cacacacaca cacacacaca cacacaattt ataaaacaaa 150900
tctttcaaaa aatcaactgg ggactctcag tgagtggaca aacttgtgca agagttatgt 150960
ttctacctac aaggaaacat gtttttgatg aaaatatttc agaaattaaa aagtaaattc 151020
tatatcaacc ataaattact tacgatttct accacttgct acatcaaaat ttatgataag 151080
agtcaacaca gatgaaagaa aatgaaaatg tgattaagat aaataatgaa aatagaaaaa 151140
tcaaaacaga aacataaatt tttgaaccat aaagtttaat tctatttctc tttctgatac 151200
catataattg tagacccacc atccactaag catttgttgg actccatctc atcttataaa 151260
acatttttc tccagaaaat tctacagttt taatctaggc ttaaaagtaa acctcaaaaa 151320
aaaaaaaaaa gtaaatctct gccaggtggt ggtagcacac acctttaatc ccagcacttg 151380
ggaggcaggg gcaggtggat cgctgtgaat cccaggctag cctggtctac agagggagtt 151440
ccaggacagc caggactaca cagagaaacc ctgtctcaaa aatcaaaaca acaacaacaa 151500
aagtaaatca gaactgtgca tggtggagca cacctaaaat ccttacacta atgagggtga 151560
gtcatgtaca cccagaatcc cacagcacct ggatccacag ttgagatcct tgtttcaaaa 151620
aggcatgagc agaggcagag gcaggcggat ctctgtgagt tcgagaccag cctggtctac 151680
aaaagcgagt accaggacag cctccaaagc cacacagaaa ccttgtctca aaaaaccaaa 151740
aaaaaaaaaa aaaaaaaaaa aaaggacaag agctgcaggt tagtggtagt gcagcttcct 151800
gatgatgtaa gaccttggac tgatcacaaa aacttctttc ccccaccacga aacacacaca 151860
cacacacaca cacacacaca cacacatgaa aaaggaagag aaggtagtgg aggggaagga 151920
agaagagaat aacctataat tttaaaatac caataagctt tagaaggaaa aataagagta 151980
ataacaaaca tttaagcaac caaaaagtgt tggatttaat gaacatgtta tgctaccatg 152040
```

gacaattcaa gggagggaaa tcctttgatc tatattaaaa tcaatattct aataattcta 152100
ggaattgaat tcatgtccca aaagttcttt tacagtagag cataaagggt ctgatatatt 152160
caaatcaaac agaatgaata ctagaaaagt cacatcaatt taaccacagc ataaaaatgc 152220
tctgctcatt tcaattgaga agacagtcct atcagttgag ttgttggctt gtttttaata 152280
aatggacttt aggaaaacag atgcaaatgt ctacagggga tcatgctgat ctaggcttct 152340
ttgtgaatcc aaggaggaat gatagtacat taagatctag atctgggctt ccagaattct 152400
tgagtctcac ctctaagtcc taaaacaaaa tgatccaaat gctggaggtt aaggaagaag 152460
gtgtcagtta tactcccgag tgctcaataa tccccagaaa acttgtgaat aactggaaaa 152520
ggctttcaac ctcttcctct tcaaaaacta aacagattac tataaattaa aaacaaacaa 152580
aaaaaaccct ctttctcatt gttaagaaac aaattctatg ggcaggagcg gtaccttagt 152640
ggcagaatcc acggaggacc ctcttcccag cagctcctgc accaggccca cgtggccttc 152700
cttggctgcc agatggagag cattgagtcc attctgagag aagaataagt gaggcttaga 152760

<210> SEQ ID NO 10
<211> LENGTH: 1219
<212> TYPE: DNA
<213> ORGANISM: Cricetulus griseus
<220> FEATURE:
<223> OTHER INFORMATION: Ankyrin 2 gene
<308> DATABASE ACCESSION NUMBER: GenBank NCBI No. NW_003635654.1
<309> DATABASE ENTRY DATE: 2011-10-27

<400> SEQUENCE: 10
taaaaaccct aggatgcaca atggctcatc ccaacacatg tctgcacagt ctagactata 60
tggattttca gatgaccttc aagcctgtat ctcatactgc ccatggattt ttctggttaa 120
ctttggtaac tttttagcct gacagataaa caaaagcttt ttctagtatt caactaggac 180
agtaacttga catggtagtt tggggcaaag aaaaacttca ctcactgaat gaccatattc 240
tttaaggatt tcctatgatg aaatctgggc tcacagggca acagctaaca ctgaacctgt 300
gtactccttt ctctagattt acaagagctc agactgtcaa agcttagggg tttcttatgt 360
tccagtcttt ctagtttgaa agtaaaaata taagaataaa aaaatgaaag aaccatcaat 420
agaaacaaaa ccacagaaag ctgtgtagct ttggcacggt tgaggaagta tacactgggg 480
aagcctgacc ttttgaaaag ctgtgtcact gtccagtcct tccaagacct gaggctggtc 540
atctgctgac tccactatca ccaggctggt tttccttgga gacttctcct cattgggctc 600
aggagcttcc tcgggttctt gcacgatggg agaaccacgc tcgctagtca ctggggtctg 660
gagacaagac tttgcttcct ctgcaggggt actgatgtcc tcaggagtct tacagagaga 720
gtcaggaact tctgtggctt tttgagtctc tgccccttct gcccctggtg ttgtcacact 780
gcaacagaaa agtaatttgc cactcaagaa cactggaagg aaaaataata tttctcttca 840
tggtagccaa gacaatatgc actcacgcat aaacacacac actaaacatg ggaaaaatga 900
gttttagaca acaaatattt atagataatg cttttagaag aaagcaagaa attttagcag 960
aataaaataa acccatatta atgtagttag tataattata aacataatgg agcataattg 1020
catatcatta tttaatggaa ggaactgttg acactgacac tctggcagtt tggagtgact 1080
ctcatgcagc cttttaaaac ctcagtttgt aagtaagaac atcatttccc ctttttttgct 1140 tcttgctttg tatccaacag ttttctgtcc caaaggtaca ttttactctc tctgtctttc 1200
ttttccttcg cttttctgt 1219

<210> SEQ ID NO 11
<211> LENGTH: 2001
<212> TYPE: DNA
<213> ORGANISM: Cricetulus griseus
<220> FEATURE:
<223> OTHER INFORMATION: Cpsf4 Gene
<308> DATABASE ACCESSION NUMBER: GenBank NCBI No. NW_003614125.1
<309> DATABASE ENTRY DATE: 2011-10-27

<400> SEQUENCE: 11

```
aaaaacggtt ctgaaaattg gaatgatacg gtaatttact gagaatatat tatttcttgg     60
gtctttccat tctttgttca tcatagatta aattaaattc atgtgaagag acagccccaa    120
gaacaagtcc agactcatca aaactttaag aatatgggcc ggtttcacca ctcagtggaa    180
aaaccatttg tggttcctac agaggatctg ggttatgtcc caacatccta tagcagcagc    240
ttacaatcct tcttacctct agttccagga ctttgatcac cgcttacatt acatatgcac    300
aattgacata catacatgtg gacaaaacac tcatacacat aaaatcaaaa taatgcatct    360
tttgaagaaa gcataaaaac caatatacag aattgtgata tgacccggca tccctttttgg    420
gacggcagtg actgcaggcg agaaggaggg gatggcagag agcagtgtga agtggggagg    480
gcagctaaga gacctgaggg ggagccaggt cttaggcctc tgccgccgct gccatgcata    540
aaatcatcgc cagcgtggac cctatcaagt tcgacttgga gatcgccatg gagcaacagc    600
tccaggccct tccctggata agtcgggggc tgctgtctga gaattcattt tgaaagctgc    660
ctgtggcaaa tgtggcatgt gtccattccg ccacattagt ggtgagaaga cagttgtgtg    720
caaacactgg ctaagagcac tctgcaagaa aggggaccag tgtgagttct tacatgagta    780
cgacatgacc aagatgcccg agtactactt ttactccaag ttcgggaaat gcaacaacaa    840
ggagtgcccc ttcctgtaca tcgaccctga gtctaagatt aaggactgcc cttggtatga    900
ccacggcttc tgtaagcatg gcccccctgtg caggcatcgg cacactcgga gagtcatttg    960
tgtgaattac ctggtaggat tctgccctga ggaaccctag ggtagattca tgcaccctcc   1020
atttgaactg cccatgggaa ccactgagca acctccacta ccacaacaga tacagcctcc   1080
aacaaagatc attgggttca tgcagagtca aaatagcagt gcagggaacc tgggaccctg   1140
gacattggag caagtcactt actataagtg tggtaaaaaa ggacactatg ccaacagatg   1200
caccaaaggg ccaattggca tttctcagtg gacagtgaca atagctgggc tctgtggagc   1260
agcctaagag acctgctgtt ggtaacaagc acttagctgc tcaatgtagt gctggcagga   1320
ctggctagag cctcaggcac acttgccagg gctcattttg aggggccatg tctgtcctat   1380
cattttgctg taatcttttt tctttaaaga aggaacatgt gcttcagttg ggtcccttga   1440
gccagcttgc ttggacatca gtgcctcatt ttttggacta tgtgctctct tccctcttgg   1500
agagagagaa gttgggaagg gctgtgtttc ttggtcctgt ttggaagatg actagcagtt   1560
cctttcaggg cctcattaaa caccagcacc gggataggat gggtggatca tgtgggactg   1620
tggccaggtc accctgcttt ctccaggtcc agccgaagcc tcgaggtgtg tctatgaatg   1680
tgacgtgaac aagggagcgc ttctagacaa acttggagca tttactgcct ggcctggccc   1740
tggctcttta gagaggtgtc aggatcccag gctgagctgc ttttctgggc ttgctttctt   1800
gtggatactt gcctgacagt gcttcgggca caccttcagt cagtgctgca ggccaccttt   1860
aaatagctga cccagttgaa ctgcacctac ctcctgccaa gcaaactctg tgctgtcatt   1920
cagaccccca tggcatgcag aggccaccca tccttgagcc tagaaaatgt gaatccatca   1980
tctgcaacct gctgggcaaa t                                              2001
```

<210> SEQ ID NO 12
<211> LENGTH: 2001
<212> TYPE: DNA
<213> ORGANISM: Cricetulus griseus
<220> FEATURE:
<223> OTHER INFORMATION: C-Mos gene
<308> DATABASE ACCESSION NUMBER: GenBank NCBI No. NW_003614707.1
<309> DATABASE ENTRY DATE: 2011-10-27

<400> SEQUENCE: 12

```
aaaaaaagca cagtgaactt gtgcactttt caggctataa tgattgttag tgctagtcct     60
cctcagctgc gttaaatcac tccaagcagc tattggatgc aagagttgca atacaaatag    120
caggcatttg tcgaaccact tgccaagatt attaggtgca accttcataa gaattaaaaa    180
ttgtaacttt aatgtcatta atcaaaatag aatcagtgat acaaaaacatg cacacctcct   240
aagttcatca gaagggggat tctgatggat ttgatttcta cagcaagaag acttcttagc    300
aacaccccga cttcctacca gtccttcctt tccaggcaag tcaggtcacc cagattctag    360
accacagcca acaagttact ggaacttaac acagacttgg agggagagaa aaaggaacaa    420
agtgagtgtg atggccatag ctgtaaataa gcacaggaaa accaggagga acagacatgg    480
cacagaatca ctggaatcct tctatagtac agaaaagcag gcactaaaca taaattcagg    540
gcctggccac caaaccagac tcatcatttc caattttcat aatacagtgc tcattttcat    600
gccatatttt tgggggaaaa gaagagagca acaatcttac tctgtcattt aaacagtccc    660
tgaaagtgct caggagctac acttttcagc acttggtaaa gctttttttt tttttttttt    720
ctttttgct tacatgtgat aagtgaccac tttttatgtg acagctatgt gcttctgatt    780
ttagaactac aggttttgag aaggcaagtt aataaagaga gccgtttcta tcaacaactc    840
aaaattcata taacttcaaa tttctacttg atgttaataa tatggttcag tctgtcacct    900
tgggcataat ctttttattt tatttatatt ggaaacaagc ttcttttaca tgtcaatcta    960
agttctctct ccctcccttc ctcccctgcc cctgaccgac ccctttatac caatcccttt   1020
ctgctcccca gggaaggtga ggccttccat gggggatctt caaagtctgt catatcattt   1080
ggagcagggc ctagaccctc cccagtgtgt ctaggctgag aaagaatccc tctatgtgga   1140
gagggctcct tgggcataat atttaattgt ttgaacctca atgctttatt aagaaattag   1200
gataataatt attaaaaaaa ttttttgggg ggagaatgaa agttgggtat ttctgaacag   1260
attaacggga caaactatta aaaaatgtaa actatagagc attttagtat aatccccatt   1320
ctgtgccatt gtaccaaatg ccaaataaaa aggcatggca aaatataaaa gtgctgaaat   1380
taggtggtta gtggtggcac acacaccttc gatcccagca ttcgggaagc agaagcaggc   1440
ggatctctct gagttcaatg tcagcctggt ctacagagcg agttccagga cagccaaaga   1500
tacacagaga aaccctgtct tgaaatacct tcccccaaaa agagtactgg aatcacacta   1560
taaatttgct tgatatctat catatagata aaattacagc tctggactca gaactgtggg   1620
ctttaagggg gtaagagtaa tagggtgcct taaaactctg ggtatcacac aaaatacatt   1680
acaatgtgat tcattatttt gtgtgttcca gttttaagac aacctcataa ataattcatt   1740
tctaaagccc aatttagaat ataaggtatt agtgaaggaa tgattcacaa cttacacaca   1800
tctcaagttc actcttccat cactggccta tctactcaag tttaacagaa tgtccattat   1860
tcactacttg tttactttta tagatatttt aaattacaaa tgggttacat cctaataagc   1920
ccatcaaagg ttgaaagtac taataggtgg aaaatgcatt cattaaatgc tttacctaca   1980
```

-continued

```
aaatgtcaga gatggttatc a                                                2001


<210> SEQ ID NO 13
<211> LENGTH: 1001
<212> TYPE: DNA
<213> ORGANISM: Cricetulus griseus
<220> FEATURE:
<221> NAME/KEY: misc_feature
<222> LOCATION: (310)..(348)
<223> OTHER INFORMATION: n is a, c, g, or t
<220> FEATURE:
<223> OTHER INFORMATION: Nephrocystin-1/Mal Gene
<308> DATABASE ACCESSION NUMBER: GenBank NCBI No. NW_003613665.1
<309> DATABASE ENTRY DATE: 2011-10-27

<400> SEQUENCE: 13

gaagccaaat cgcgagtctc acaaatgcca caggaaagct ctcgtagcta tggagtttac      60

catgcttaaa ctatttcaaa gtttagtttc ccggaacagg cgtcggaaag ctgcatagaa     120

cagagcaacg catggtacga ggtcgtgata gtgacgagac gcacagtctg aggactcccg     180

ggttacgtcc ccatccttag gaatccacag tagttgttct taggccgttt agcgaatccg     240

gtggcgctgg gtggcggcgc ccgctgatag cgtcatcttg ctgagctccc gttttggttt     300

ccctggcaan nnnnnnnnnn nnnnnnnnnn nnnnnnnnnn nnnnnnnngc tcaggcgccg     360

cgggcaggag cttaagcttc aggtaggtgc atgggagggg gccccacatc ccagcccctc     420

gccaggaccc gagcgctggg ccgcagcgtt ctaacctcga tccccgccgt agacaaaacc     480

tccagaaagc cttgctagtc agctaacacc tcagtcctta acccctctca cccctcccgc     540

gcatgtctag actagtcaga tccaccccag tcctttgcca ctctgctttg aaagtcatcg     600

ctttctcaaa aatcaagtgt aacaggtgtc aagtgtagca agaatagtgt taatacctga     660

gatccgataa acgagccaag gacaggagat tagtaactta agttaatttc aaaggtagtc     720

aagcacctgc aaaagaggta agatcgtagc gattttaagt cataaccctc agtgctgagg     780

aagactcgat gaaacaggcg atgccctggt atatagtcta catttctgga cagcagtttg     840

acaacatata gcgagcattg atcctcctag gctggttgat tacattctca gcaatctccc     900

acttacaata acttaaaagt gtgacagaga tggatattta aatgtgttca ccacattttt     960

tgcttataat agaaaagctg aatatgaata aatgataggt a                         1001
```